(12) United States Patent
Benner et al.

(10) Patent No.: US 8,212,020 B2
(45) Date of Patent: Jul. 3, 2012

(54) REAGENTS FOR REVERSIBLY TERMINATING PRIMER EXTENSION

(76) Inventors: Steven Albert Benner, Gainesville, FL (US); Daniel Hutter, Gainesville, FL (US); Nicole Aurora Leal, Gainesville, FL (US); Fei Chen, Beijing (CN)

(*) Notice: Subject to any disclaimer, the term of this patent is extended or adjusted under 35 U.S.C. 154(b) by 355 days.

(21) Appl. No.: 12/383,306

(22) Filed: Mar. 23, 2009

(65) Prior Publication Data
US 2011/0275124 A1    Nov. 10, 2011

Related U.S. Application Data

(63) Continuation-in-part of application No. 11/373,415, filed on Mar. 11, 2006, now Pat. No. 7,544,794.

(60) Provisional application No. 60/661,142, filed on Mar. 11, 2005.

(51) Int. Cl.
*C07H 17/02* (2006.01)
*C07H 19/04* (2006.01)
*C07H 19/10* (2006.01)
*C07H 19/20* (2006.01)
*C07H 21/04* (2006.01)

(52) U.S. Cl. .......... 536/25.31; 536/25.32; 536/25.33; 536/26.26; 536/17.9

(58) Field of Classification Search .......... None
See application file for complete search history.

(56) References Cited

U.S. PATENT DOCUMENTS 6,686,461 B1 * 2/2004 Schwartz et al. .......... 536/26.26
2003/0113769 A1 * 6/2003 Manoharan et al. .......... 435/6

OTHER PUBLICATIONS

U.S. Appl. No. 11/513,916, filed Aug. 2006, Benner, Steven Albert.*

* cited by examiner

*Primary Examiner* — Eric S Olson

(57) ABSTRACT

This invention relates to the field of nucleic acid chemistry, more specifically to the field of compositions of matter that comprise triphosphates of modified 2'-deoxynucleosides and oligonucleotides that are formed when these are appended to the 3'-end of a primer, wherein said modifications comprise $NH_2$ moiety attached to their 3'-hydroxyl group and a fluorescent species in a form of a tag affixed to the nucleobase via a linker that can be cleaved. Such compositions and their associated processes enable and improve the sequencing of oligonucleotides using a strategy of cyclic reversible termination, as outlined in U.S. Pat. No. 6,664,079. Most specifically, the invention concerns compositions of matter that are 5'-triphosphates of ribo- and 2'-deoxyribonucleosides carrying detectable tags and oligonucleotides that might be derived from them. The invention also concerns processes wherein a DNA polymerase, RNA polymerase, or reverse transcriptase synthesizes said oligonucleotides via addition of said triphosphates to a primer.

13 Claims, 22 Drawing Sheets

1b                      thymidine

6-FAM

US 8,212,020 B2

REAGENTS FOR REVERSIBLY TERMINATING PRIMER EXTENSION

This application claims in part priority of the provisional application 60/765,520, filed Feb. 6, 2006, and U.S. patent application Ser. No. 11/373,415, filed Mar. 11, 2006.

FIELD

This invention relates to the field of nucleic acid chemistry, more specifically to the field of compositions and processes that can be used to determine the sequences of nucleic acids. More specifically, this invention relates to compositions that allow the sequencing of oligonucleotides by a process that adds a fluorescently tagged nucleotide to a primer where the 3'-hydroxyl group of the product oligonucleotide is blocked by a group that can be removed.

BACKGROUND

"Sequencing-by-synthesis" of the type known as "sequencing using cycle reversible termination" (SuCRT) is a strategy that extends a primer by template-directed addition of one nucleotide at a time, using a nucleoside triphosphate or thiotriphosphate as a source of the added building block. Polymerization is stopped for a time after each nucleotide incorporated. In that time, the extended primer is examined to determine what nucleotide is incorporated, and to infer the nucleotide in the template that directed the incorporation.

One mechanism to cause polymerization to stop is to have its 3'-hydroxyl group blocked by a removable protecting (or blocking) group. This blocking group prevents the polymerase from adding additional nucleotides until the blocking group is removed. In practice, this provides an arbitrarily long time to determine the nature of the added nucleotide.

One strategy to determine the identity of the nucleotide added is to have each nucleotide carry a fluorescent tag, where the color of the fluorescence emission is distinctive for the type of nucleotide. After extension, but before removing the blocking group, the nature of the nucleotide incorporated is determined by reading the fluorescence from the tag. After this is done, the tag and the 3'-protecting group are removed, and the next cycle of sequencing is initiated. In this architecture, template-directed polymerization is done using a DNA polymerase or, a reverse transcriptase.

When the output is fluorescence, this implementation of the strategy requires:
(a) Four analogues of dATP, dTTP, dGTP, and dCTP, each carrying a fluorescent dye with a' different color, with the 3'-end blocked so that immediate elongation is not possible.
(b) The four analogues must be incorporated to allow the elongation reaction to be completed before undesired reactions occur and avoid ragged ends from incomplete incorporation.
(c) The incorporation must be substantially faithful. Mismatched incorporation, if not corrected by proofreading, will lead to the loss of strands if the polymerase does not extend efficiently a terminal mismatch. This will gradually erode the intensity of the signal, and may generate "out of phase" signals that confuse the reading of the output downstream.
(d) The dye and the group blocking the 3'-OH group must be cleaved with high yield to allow the incorporation of the next nucleotide of the next nucleotide to proceed. Incomplete cleavage will erode the intensity of the signal or generate "out of phase" signals that confuse downstream reading. For single molecule sequencing, failure to cleave the 3'-OH blocking group may lose a cycle of sequence data collection.
(e) The growing strand of DNA should survive the washing, detecting and cleaving processes. While reannealing is possible, conditions that allow the DNA primer and template to remain annealed are preferable.

In their most ambitious forms, sequencing-by-synthesis architectures would use the same nucleoside modification to block the 3'-end of the DNA and to introduce the fluorescent tag [We199]. For example, if a fluorescent tag is attached to the 3'-position via an ester linkage, replacing the hydrogen atom of the 3'-OH group of the nucleoside triphosphate, extension following incorporation would not be possible (there is no free 3'-OH group). This would give time to read the color of the fluorescent label, determining the nature of the nucleotide added. Then, the 3'-O acyl group could be removed by treatment with a mild nucleophile (such as hydroxylamine) under mild conditions (pH<10) to regenerate a free 3'-hydroxyl group, preparing the DNA for the next cycle.

The difficulty in implementing this elegant approach is the polymerases themselves. Any tag that fluoresces in a useful region of the electromagnetic spectrum must be large, on the order of 1 nm. Crystal structures of polymerases show that the 3'-position in the deoxyribose unit is close to amino acid residues in the active site of the polymerase, and do not offer the incoming triphosphate the space to accommodate a tag of that size. The polymerase, therefore, is not likely to be able to handle substituents having a tag of this size at the 3'-position. Indeed, polymerases do not work well with any modification of the 3'-OH group of the incoming triphosphate. For example, to accept even 2',3'-dideoxynucleoside analogues (where the 3'-moiety is smaller than in the natural nucleoside), mutated polymerases are often beneficial.

Ju et al., in U.S. Pat. No. 6,664,079, noted these problems as they outlined a proposal for SuCRT based on various 3'-OH blocking groups. They suggested that a fluorescent or mass tag could be attached via a cleavable linker to a point on the nucleoside triphosphate other than on the 3'-OH unit (FIG. 1). This linker could be attached (without limitation) to the 5-position of the pyrimidines (T and C) and the 7-position of the purines (G and A). According to U.S. Pat. No. 6,664,079, tags at this position should, in principle, allow the 3'-OH group to be blocked by a cleavable moiety that is small enough to be accepted by DNA polymerases. In this architecture, multiple cleavage steps might be required to remove both the tag (to make the system clean for the addition of the next tag) and the 3'-blocking group, to permit the next cycle of extension to occur [Mit03][Seo04].

U.S. Pat. No. 6,664,079 struggled to find a small chemical group that might be accepted by polymerases, and could be removed under conditions that were not so harsh as to destroy the DNA being sequences. U.S. Pat. No. 6,664,079 cited a literature report that 3'-O-methoxy-deoxynucleotides are good substrates for several polymerases [Axe78]. It noted, correctly, that the conditions for removing a 3'-O methyl group were too stringent to permit this blocking group from being removed under any conditions that were likely to leave the DNA being sequenced, or the primer that was being used, largely intact.

An ester group was also discussed as a way to cap the 3'-OH group of the nucleotide. U.S. Pat. No. 6,664,079 discarded this blocking group based on a report that esters are cleaved in the active site in DNA polymerase [Can95]. It should be noted that this report is questionable, and considers only a single polymerase. Nevertheless, ester linkages are susceptible to spontaneous hydrolysis in water, especially if they are small (such as the formyl group).

Chemical groups with electrophiles such as ketone groups were also considered and discarded by U.S. Pat. No. 6,664,079 as not being suitable for protecting the 3'-OH of the nucleotide in enzymatic reactions. Polymerases have nucleophilic centers (such as amino groups) in the polymerase that were proposed to react with the amino groups of proteins. In fact, this is unlikely (cyclopentanone, for example, does not form appreciable amounts of imine with protein side chains). However, a 3'-keto 2'-deoxyribose unit in a nucleoside is not stable to decomposition via beta elimination reactions, as is well known in the literature studying the mechanism of ribonucleotide reductases.

U.S. Pat. No. 6,664,079 then cited a literature report that 3'-O-allyl-dATP is incorporated by Vent (exo-) DNA polymerase in the growing strand of DNA [Met94]. U.S. Pat. No. 6,664,079 noted that this group, and the methoxymethyl MOM group, having a similar size, might be used to cap the 3'-OH group in a sequencing-by-synthesis format. This patent noted that these groups can be cleaved chemically using transition metal reagents [Ire86][Kam99], or through acidic reagents (for the MOM group).

These suggestions therefore define the invention proposed in U.S. Pat. No. 6,664,079. Briefly, the essence of this invention is an architecture where the triphosphates of four nucleotide analogues, each labeled with a distinctive cleavable tag attached to the nucleobase, and each having the hydrogen of the 3'-OH group capped replaced by an allyl group or a MOM group, are used as the triphosphates in the sequencing by synthesis architecture, and the products are oligonucleotides prepared by polymerase incorporation that have this replacement.

Unfortunately, various other aspects of a practical tool for sequencing using cyclic reversible termination were not anticipated by U.S. Pat. No. 6,664,079, and are not enabled in the prior art. In particular, the cleavage reaction that removes the fluorescent tag may not restore the nucleobase to its natural structure, leaving behind what is known in the literature as a "scar". It is a question open to experimentation as to whether a primer whose 3'-nucleotide carries a scar will be extended in a template-directed polymerization reaction by an incoming triphosphate that carries both a 3'-O blocking group and a fluorescently tagged nucleobase. While architectures are easily conceived that use mixtures of fluorescently tagged and untagged triphosphates to implement a sequencing using cyclic reversible termination strategy, it would be preferable to identify polymerases that will add a 3'-blocked fluorescently tagged nucleotide to a scarred primer.

DETAILED DESCRIPTION OF THE INVENTION

Figure 1:
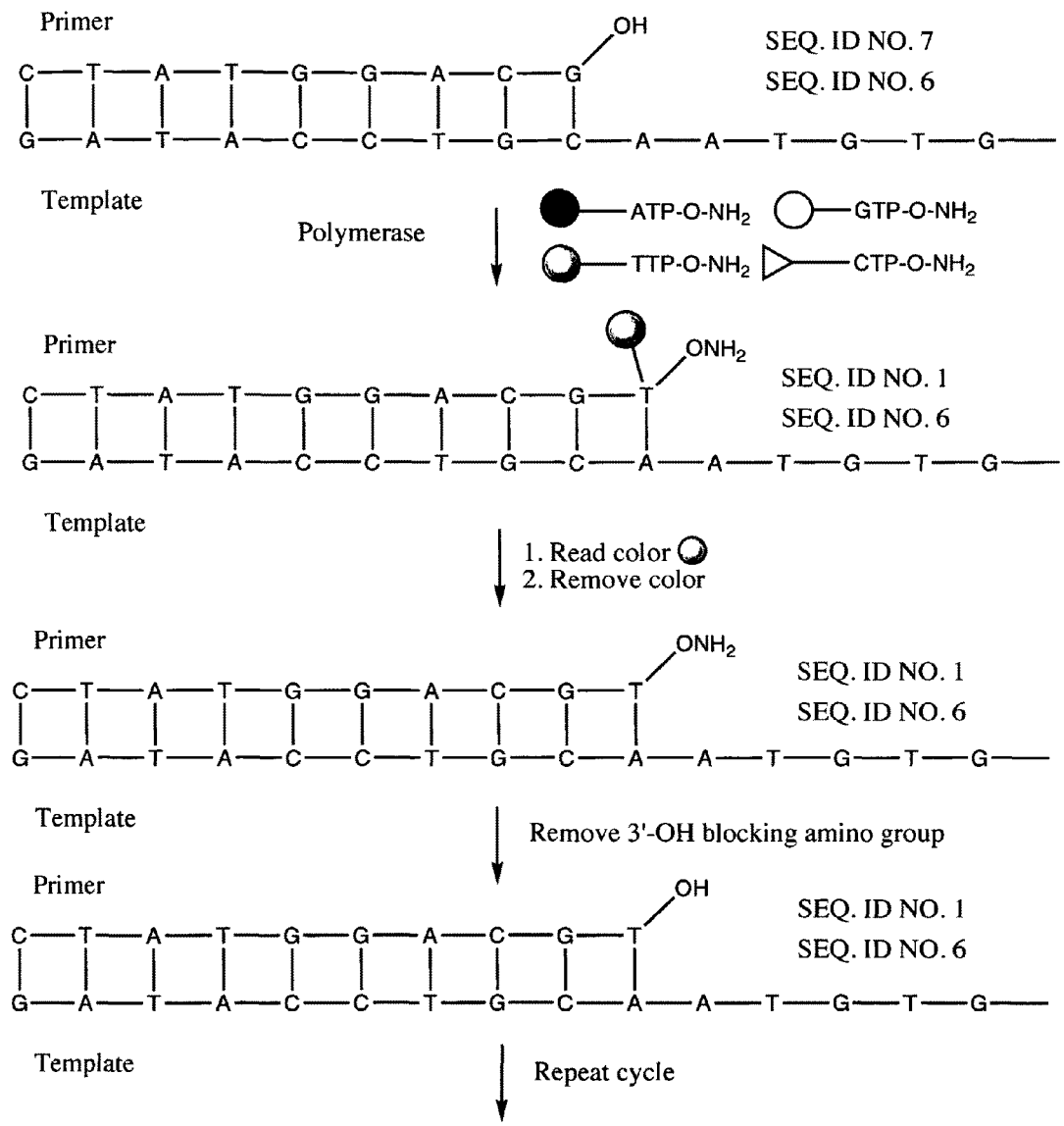
FIG. 1. Schematic for sequencing-by-synthesis using the 3'-ONH$_2$ group as a small, removable 3'-blocking group. The circles and triangles represent fluorescent groups having different colors. The 3'-blocked fluorescently tagged nucleotide is incorporated by a DNA polymerase. Chain termination then stops, because of the 3'-blocking group. The fluorescence color is read (determining which nucleotide was added), the fluorescent group is removed, and the 3'-OH is deblocked. The cycle can then be repeated.

U.S. patent Ser. No. 11/373,415, which is incorporated herein by citation, suggested that a 3'-O-NH$_2$ group might be a useful reversible terminator for an architecture involving sequencing using a cyclic reversible termination (SuCRT) architecture (FIG. 1). This group is incorporated within the compounds of the instant invention. These are nucleoside triphosphates that carry a 3'-O-NH$_2$ group as well as a nucleobase to which is attached a tag, which may be fluorescent, via a linker that contains a functional group that can be cleaved through the addition of the reagent. In this case, the cleavable functional group is a 1,2-diol unit that is cleaved by addition of a salt of periodate, preferably in aqueous solution near neutral pH.

Also novel to the compositions of the instant invention is a derivative of these where the 3'-O—NH$_2$ group is protected in the form of an oxime. This oxime transiently protects the 3'-O—NH$_2$ group, allowing transformations of other parts of the molecule, including modification of the linker so as to introduce fluorescent tags. This oxime can be removed prior to incubation of the triphosphate with a primer-template complex in the presence of a polymerase.

In the compounds of the instant invention, these fluorescent groups are appended to the five position of pyrimidines or to the 7-position of 7-deaza purines. Further, to permit the cleavage of the fluorescent groups from the nucleobases, the linkers within the compounds of the instant invention contain a vicinal 1,2-diol. This diol is rapidly cleaved by periodate.

In the course of developing the compositions of the instant invention, it was noticed that the 3'-ONH$_2$ group could be protected as an oxime, either with acetone or acetaldehyde (although other aldehydes and ketones should be considered to be functional equivalents for this purpose). Further, it was discovered that it was convenient to store certain compositions containing 3'-oxime units, making these valuable compositions in their own right.

A series of experiments showed that THERMINATOR® (a registered trademark of New England Biolaboratories) was able to add to a primer nucleotides derived from compositions of matter that are nucleoside triphosphates carrying a 3'-$ONH_2$ group and a diol-containing linker attached to the nucleobase and carrying a fluorescent moiety, and that this polymerase worked for all four of the standard nucleobase equivalents. Further, it was shown that THERMINATOR® will add to a primer such a nucleotide even if the 3'-nucleotide contains a scar derived from the periodate cleavage (optionally followed by reduction with sodium cyanoborohydride) of a nucleoside that had been added to the 3'-end of the primer in a previous primer extension step.

A further teaching of the instant invention is a process that involves incubation of a primer-template complex with a mixture of nucleoside triphosphates complementary to nucleosides in the template, some of which carry a fluorescent tag and others that do not. This has advantages when the polymerase does not easily extend a "scarred" primer, that is, a primer whose 3'-nucleotide has a nucleobase to which is appended a fragment of a side chain, such as one that comes from the cleavage of the side chain of a previously incorporated nucleotide carrying a linker and a fluorescent tag. In this process, untagged nucleosides with a 3'-reversible blocking moiety are added to scarred primers while tagged nucleosides with a 3'-reversible block are added to the unscarred primers. In this way, the process can lead to readable sequence with polymerases that are not optimal for SuCRT with only tagged nucleoside triphosphates.

References

[Axe78] Axelrod, V. D., Vartikyan, R. M., Aivazashvili, V. A., Beabealashvili, R. S. (1978) Specific termination of RNA polymerase synthesis as a method of RNA and DNA sequencing. *Nucleic Acids Res.* 5, 3549-3563

[Can95] Canard, B., Cardona, B., Sarfati, R. S. (1995) Catalytic editing properties of DNA polymerases. *Proc. Natl. Acad. Sci. USA* 92, 10859-10863

[Ire86] Ireland, R. E., Varney, M. D. (1986) Approach to the total synthesis of chlorothricolide-synthesis of (+/−)-19.20-dihydro-24-O-methylchlorothricolide, methyl-ester, ethyl carbonate. *J. Org. Chem.* 51, 635-648

[Kam99] Kamal, A., Laxman, E., Rao, N. V. (1999) A mild and rapid regeneration of alcohols from their allylic ethers by chlorotrimethylsilane/sodium iodide. *Tetrahedron Lett.* 40, 371-372.

[Kec79] Keck, G. E., Fleming, S., Nickell, D., Weider, P. (1979) Mild and efficient methods for the reductive cleavage of nitrogen-oxygen bonds. *Synth. Commun.* 9, 281-282.

[Met94] Metzker, M. L., Raghavachari, R., Richards, S., Jacutin, S. E., Civitello, A., Burgess, K., Gibbs, R. A. (1994) Termination of DNA synthesis by novel 3'-modified-deoxyribonucleoside 5'-triphosphates. *Nucleic Acids Res.* 22, 4259-4267

[Mit03] Mitra, R. D., Shendure, J., Olejnik, J., Olejnik, E. K., Church, G. M. (2003) Fluorescent in situ sequencing on polymerase colonies. *Anal. Biochem.* 320, 55-65.

[Seo04] Seo, T. S., Bai, X., Ruparel, H., Li, Z., Turro, N. J., Ju, J. (2004). Photocleavable fluorescent nucleotides for DNA sequencing on a chip constructed by site-specific coupling chemistry. *Proc. Natl. Acad. Sci. USA* 101, 5488-5493

[Wel99] Welch, M. B., Burgess, K. (1999) Synthesis of fluorescent, photolabile 3'-O-protected nucleoside triphosphates for the base addition sequencing scheme. *Nucleosides Nucleotides* 18, 197-201

EXAMPLES

Example 1

Figure 2:
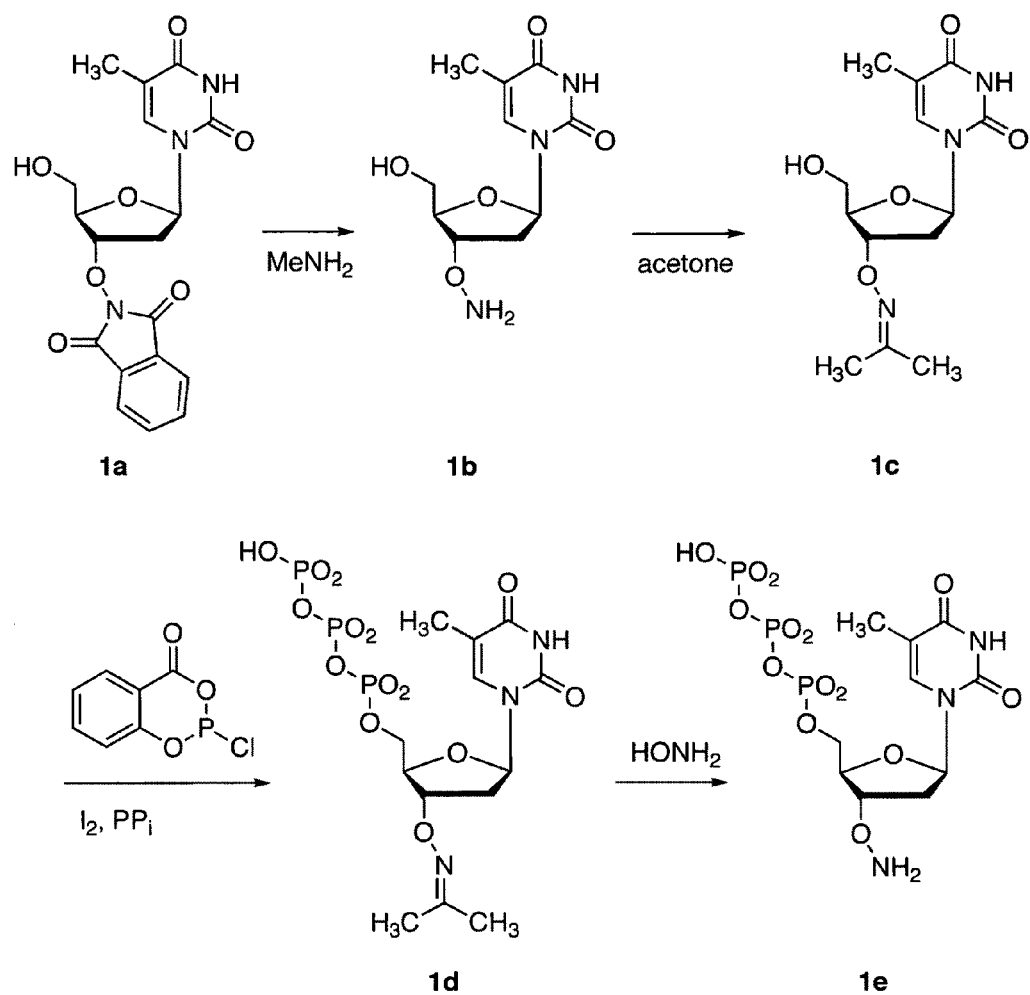
FIG. 2. Example 1. Synthesis of TTP-ONH$_2$
FIG. 3. Example 2. Synthesis of dCTP-ONH$_2$
FIG. 4. Example 3. Synthesis of dATP-ONH$_2$
FIG. 5. Example 4. Synthesis of dGTP-ONH$_2$
FIG. 6. Example 5. Synthesis of linker component FIG. 7. Example 6. Synthesis of thymidine analog with acetylene linker and a Cy3-fluor (part 1)
FIG. 8. Example 6. Synthesis of thymidine analog with acetylene linker and a Cy3-fluor (part 2)
FIG. 9. Example 7. Synthesis of cytidine analog with acetylene linker and Cy3.5 floor (part 1)
FIG. 10. Example 7. Synthesis of cytidine analog with acetylene linker and Cy3.5 fluor (part 1)
FIG. 11. Example 8. Synthesis of adenine analog with acetylene linker and Cy5-fluor (part 2)
FIG. 12. Example 8. Synthesis of adenine analog with acetylene linker and Cy5-fluor (part 2)
FIG. 13. Example 9. Synthesis of guanine analog with an attached fluor (part 1)
FIG. 14. Example 9. Synthesis of guanine analog with an attached fluor (part 2)
FIG. 15. Example 9. Synthesis of guanine analog with an attached fluor (part 3)
FIG. 16. Example 10. Nitrous acid removal of 3'-ONH$_2$ group.

Synthesis of TTP-$ONH_2$ (FIG. 2)

3'-O—(N-Acetone-oxime)-thymidine (1c)

3'-O-Phthalimido-thymidine (1a), prepared following procedures described in literature [De Clercq, E., Inoue, I., Kondo, K. (1990) Preparation of 3-O-amino-2'-deoxyribonucleoside derivatives as antiviral agents for human retrovirus, particularly human immunodeficiency virus. *Eur. Pat. Appl.* 14 pp][Kondo, K., Ogiku, T., Inoue, I. (1985) Synthesis of 5'(3)-O-amino nucleosides. *Symp. Nucleic Acids Chem.* 16, 93-96][Burgess, K., Gibbs, R. A., Metzker, M. L., Raghavachari, R. (1994) Synthesis of an oxyamide linked nucleotide dimer and incorporation into antisense oligonucleotide sequences. *J. Chem. Soc. Chem. Commun.* 8, 915-916][Cook, P. D., Sanghvi, Y. S. (1994) Preparation of antisense heteroatomic oligonucleotide analogs. *PCT Int. Appl.* 90 pp]. The procedures from these literature citations are specifically incorporated into this specification by citation. This material (1.15 g, 3.0 mmol) was dissolved in aqueous methylamine solution (4%, 22 mL, ca. 24 mmol). After 20 min at room temperature (RT), most of the methylamine was removed in vacuo and the remaining solution was treated with acetone (3 mL). After 3 h at RT, the volatiles were removed in vacuo. The residue was redissolved in a mixture of water (25 mL) and acetonitrile (7 mL). Solids were removed from the mixture by filtration (0.2 μm) prior to purification by reverse phase HPLC (Waters Prep Nova-Pak HR C18 column, 60 Å, 19×300 mm, eluent A=25 mM triethylammonium acetate (TEAA) pH 7, eluent B=$CH_3CN$, gradient from 25 to 50% B in A over 7 min, then to 80% B over 8 min, flow rate=5 mL/min, Retention time (Rt)=14 min), which gave 3'-O—(N-acetone-oxime)-thymidine (1c, 640 mg; 72%) as a colorless foam after lyophilization.

$^1$H-NMR ($d_6$-DMSO, 300 MHz): ∂ (ppm)=1.79 (d, J=0.9 Hz, 3H); 1.83 (s, 3H); 1.84 (s, 3H); 2.15-2.35 (m, 2H); 3.55-3.70 (m, 2H); 3.98-4.05 (m, 1H); 4.68-4.72 (m, 1H); 5.15 (br. s, 1H); 6.17 (dd, J=5.7, 8.7 Hz, 1H); 7.76 (d, J=0.9 Hz, 1H); 11.3 (br. s, 1H). $^{13}$C-NMR ($d_6$-DMSO, 75 MHz): ∂ (ppm)= 12.3; 15.5; 21.5; 36.4; 61.8; 82.1; 83.9; 84.1; 109.6; 136.0; 150.5; 155.8; 163.7.

3'-O—(N-Acetone-oxime)-thymidine-5'-triphosphate (1d)

To a solution of 3'-O—(N-acetone-oxime)-thymidine (1c, 300 mg, 1.0 mmol) in pyridine (4 mL) and dioxane (3.4 mL) was added a solution of 2-chloro-4H-1,3,2-benzodioxaphosphorin-4-one (260 mg, 1.4 mmol) in dioxane (2.6 mL) at room temperature. After 10 min, a mixture of tributylammonium pyrophosphate in DMF (0.2 M, 10 mL, 2 mmol) and tributylamine (1.2 mL, 4.8 mmol) were added. After 10 min, a solution of iodine (360 mg, 1.4 mmol) and water (0.56 mL) in pyridine (28 mL) was added. After 20 min, the reaction was quenched by the addition of aqueous $Na_2SO_3$ (5%, 0.5 mL) and acetone (0.5 mL). The solvents were removed in vacuo. Water (50 mL) was added and the mixture was filtered (0.2 μm). Purification by ion-exchange HPLC (Dionex BioLC DNAPac PA-100, 22×250 mm, eluent A=water, eluent B=1 M aq. $NH_4HCO_3$, gradient from 0 to 25% B in 16 min, flow rate=10 mL/min, Rt=13 min), followed by reverse phase HPLC (Waters Prep Nova-Pak HR C18 column, 60 Å, 19×300 mm, eluent A=25 mM TEAA pH 7, eluent B=50% CH$_3$CN in A, gradient from 0 to 70% B in 20 min, flow rate=5 mL/min, Rt=19 min) gave 3'-O—(N-acetone-oxime)-thymidine-5'-triphosphate as a colorless foam after lyophilization. The yield was determined by UV (260 nm, ext. coeff.=8800 Lmol$^{-1}$ cm$^{-1}$) to be 450 µmol (45%).

$^1$H-NMR (D$_2$O, 300 MHz): ∂ (ppm, rel to HDO=4.65)= 1.75-1.79 (m, 9H); 2.18-2.40 (m, 2H); 4.00-4.15 (m, 2H); 4.22-4.27 (m, 1H); 4.46 (s, 2H); 4.78-4.85 (m, 1H); 6.21 (dd, J=5.7, 9.1 Hz, 1H); 7.67 (s, 1H). $^{31}$P-NMR (D$_2$O, 120 MHz): ∂ (ppm, rel to external H$_3$PO$_4$=0)=−10.5 (d, J=20.0 Hz, 1P); −11.7 (d, J=20.0 Hz, 1P); −23.3 (t, J=20.0 Hz, 1P).

3'-O-Amino-thymidine-5'-triphosphate (1e)

To a solution of 3'-O—(N-acetone-oxime)-thymidine-5'-triphosphate (1d, 100 µmol) in water (10 mL) was added aqueous sodium acetate buffer (1M, pH 4.0, 2 mL, 2 mmol) and aqueous hydroxylamine solution (50 wt-%, 100 µL, ca. 1.6 mmol). After 2 h at room temperature, the reaction was diluted with water (20 mL) and filtered (0.2 µm). Purification by ion-exchange HPLC (Dionex BioLC DNAPac PA-100, 22×250 mm, eluent A=water, eluent B=1 M aq. NH$_4$HCO$_3$, gradient from 0 to 30% B in 20 min, flow rate=10 mL/min, Rt=15 min) gave 3'-O-amino-thymidine-5'-triphosphate as a colorless foam after lyophilization. The yield was determined by UV (260 nm, ext. coeff.=8800 Lmol$^{-1}$ cm$^{-1}$) to be 82 µmol (82%).

$^1$H-NMR (D$_2$O, 300 MHz): ∂ (ppm, rel to HDO=4.65)= 1.78 (d, J=0.9 Hz, 3H); 2.18-2.29 (m, $^1$H); 2.37-2.46 (m, 1H); 4.01-4.16 (m, 2H); 4.25-4.29 (m, 1H); 4.61-4.63 (m, 1H); 6.17 (dd, J=5.8, 9.0 Hz, 1H); 7.62 (d, J=1.2 Hz, 1H). $^{31}$P-NMR (D$_2$O, 120 MHz): ∂ (ppm, rel to external H$_3$PO$_4$=0)=−10.8 (d, J=20 Hz, 1P); −11.7 (d, J=20 Hz, 1P); −23.1 (t, J=20 Hz, 1P).

Example 2

Figure 3:
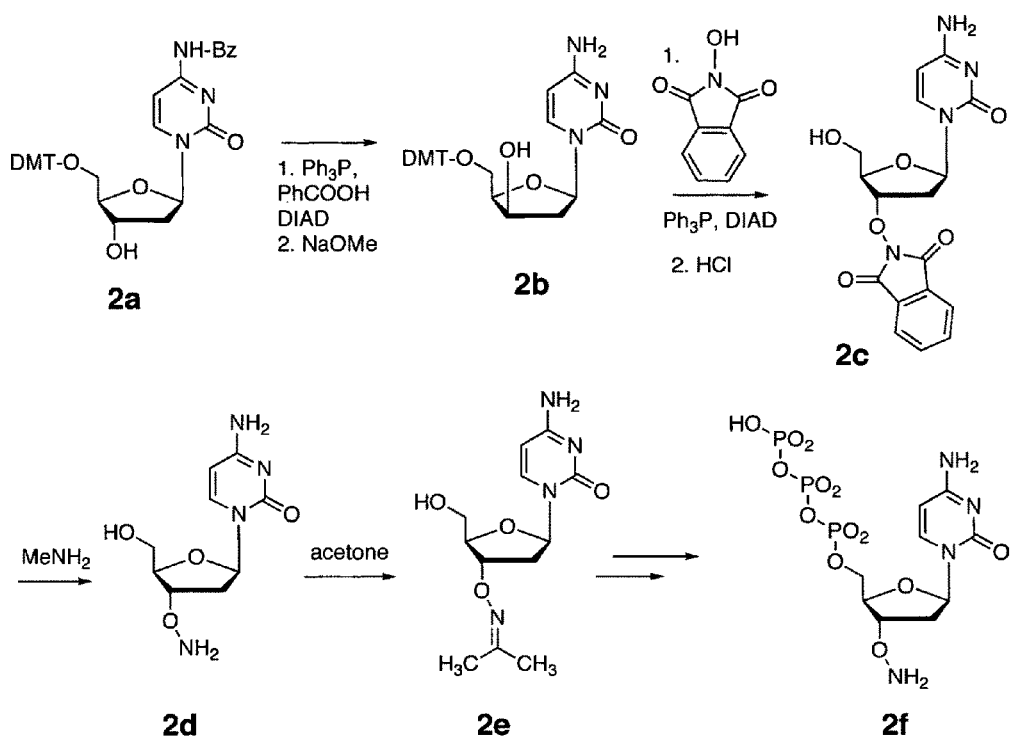

Synthesis of dCTP-ONH2 (FIG. 3)

5'-O-Dimethoxytrityl-xylo-2'-deoxycytidine (2b)

To a solution of N$^4$-benzoyl-5'-O-dimethoxytrityl-2'-deoxycytidine (2a, 8.9 g, 14 mmol), benzoic acid (2.5 g, 20 mmol) and triphenylphosphine (5.2 g, 20 mmol) in THF (150 mL) was added DIAD (3.7 mL, 20 mmol) at 0° C. The reaction was allowed to warm to RT overnight and then was quenched by the addition of water (0.5 mL). The solvents were removed in vacuo. Purification by FLC (silica, gradient 50 to 100% EtOAc in hexanes) gave N$^4$-benzoyl-3'-O-benzoyl-5'-O-dimethoxytrityl-xylo-2'-deoxycytidine (13.7 g) as a colorless foam which, according to NMR, contained significant amounts of triphenylphosphine oxide, as well as some elimination product (2',3'-olefin). This intermediate was re-dissolved in MeOH (450 mL) and treated with a solution of sodium methoxide in MeOH (5.3 M, 4 mL, 21 mmol). After 2 h at RT, the reaction was quenched by the addition of AcOH (glacial, 1.25 mL). The solvents were removed in vacuo and the residue was partitioned between CH$_2$Cl$_2$ (300 mL) and aqueous NaCl (50% sat., 150 mL). The organic phase was separated and the solvent removed in vacuo. Purification by FLC (silica, gradient 5 to 10% MeOH in CH$_2$Cl$_2$) gave 5'-O-dimethoxytrityl-xylo-2'-deoxycytidine (4.6 g; 62% overall) as a colorless foam.

$^1$H-NMR (d$_6$-DMSO, 300 MHz): ∂ (ppm)=1.78-1.87 (m, 1H); 2.46-2.55 (m, 1H); 3.19-3.24 (m, 1H); 3.37-3.43 (m, 1H); 3.76 (s, 6H); 4.07-4.12 (m, 1H); 4.16-4.19 (m, 1H); 5.10-5.20 (m, 1H); 5.66 (d, J=7.4 Hz, 1H); 6.07 (dd, J=1.7, 7.9 Hz, 1H); 6.86-6.92 (m, 4H); 7.16 (br s, 2H); 7.18-7.48 (m, 9H); 7.68 (d, J=7.4 Hz, 1H). $^{13}$C-NMR (d$_6$-DMSO, 75 MHz): ∂ (ppm)=41.4; 55.0; 62.8; 69.2; 83.4; 85.4; 85.5; 93.0; 113.1; 126.6; 127.8; 129.8; 135.6; 135.7; 141.6; 145.0; 155.2; 158.0; 165.6.

3'-O-Phthalimido-2'-deoxycytidine (2c)

To a solution of 5'-O-dimethoxytrityl-xylo-2'-deoxycytidine (2b, 3.4 g, 6.4 mmol), N-hydroxyphthalimide (1.6 g, 10 mmol) and triphenylphosphine (2.6 g, 10 mmol) in THF (180 mL) was added DIAD (1.9 mL, 10 mmol) at 0° C. The reaction was let to warm to RT overnight and then was quenched by the addition of water (0.5 mL). The solvents were removed in vacuo. Purification by FLC (silica, gradient 3 to 10% MeOH in CH$_2$Cl$_2$) gave 5'-O-dimethoxytrityl-3'-O-phthalimido-2'-deoxycytidine (3.7 g) as a colorless foam which, according to NMR, contained significant amounts of triphenylphosphine oxide and some elimination product (2',3'-olefin). This intermediate was redissolved in MeOH (150 mL) and treated with aqueous HCl (conc, 7.5 mL) at RT. Within minutes, the product started to precipitate. After 10 minutes, the solids were filtered off and dried at high vacuum to give 3'-O-phthalimido-2'-deoxycytidine (1.5 g, 63% overall) as an off-white powder.

$^1$H-NMR (d$_6$-DMSO, 300 MHz): ∂ (ppm)=2.28-2.38 (m, 1H); 2.65-2.74 (m, 1H); 3.62-3.68 (m, 2H); 4.35-4.40 (m, 1H); 4.95-5.00 (m, 1H); 6.20 (d, J=7.9 Hz, 1H); 6.25 (dd, J=6.9, 7.0 Hz, 1H); 7.89 (s, 4H); 8.22 (d, J=7.9 Hz, 1H); 8.71 (s, 1H); 9.83 (s, 1H). $^{13}$C-NMR (d$_6$-DMSO, 75 MHz): ∂ (ppm)=36.6; 61.0; 84.1; 85.8; 87.7; 94.0; 123.3; 128.6; 134.8; 144.2; 146.9; 159.5; 163.6.

3'-O—(N-Acetone-oxime)-2'-deoxycytidine (2e). 3'-O-Phthalimido-2'-deoxycytidine (2c, 375 mg, 1.0 mmol) was dissolved in aqueous methylamine solution (4%, 11 mL, ca. 12 mmol). After 10 min, most of the methylamine was removed in vacuo, and the remaining solution was treated with acetone (2 mL). After 3 h at RT, the solvent was removed in vacuo. The residue was redissolved in water (30 mL) and the mixture was filtered (0.2 µm). Purification by reverse phase HPLC (Waters Prep Nova-Pak HR C18 column, 60 Å, 19×300 mm, eluent A=25 mM TEAA pH 7, eluent B=CH$_3$CN, gradient from 0 to 50% B in 10 min, then to 85% B in 8 min, flow rate=5 mL/min, Rt=17 min) gave 3'-O—(N-acetone-oxime)-2'-deoxycytidine (2c, 200 mg; 71%) as a colorless foam after lyophilization.

$^1$H-NMR (d$_6$-DMSO, 300 MHz): ∂ (ppm)=1.83 (s, 3H); 1.84 (s, 3H); 1.99-2.09 (m, 1H); 2.30-2.39 (m, 1H); 3.55-3.66 (m, 2H); 4.02-4.06 (m, 1H); 4.65-4.70 (m, 1H); 5.30 (br. s, 1H); 5.77 (d, J=7.4 Hz, 1H); 6.17 (dd, J=5.6, 8.7 Hz, 1H); 7.23 (br. s, 2H); 7.84 (d, J=7.4 Hz, 1H). $^{13}$C-NMR (d$_6$-DMSO, 75 MHz): ∂ (ppm)=15.5; 21.5; 37.3; 61.9; 82.4; 84.2; 85.2; 94.3; 141.0; 155.1; 155.7; 165.6.

3'-O—(N-Acetone-oxime)-2'-deoxycytidine-5'-triphosphate (2e)

To a solution of 3'-O—(N-acetone-oxime)-2'-deoxycytidine (2e, 170 mg, 0.6 mmol) in pyridine (2 mL) and dioxane (1.5 mL) was added a solution of 2-chloro-4H-1,3,2-benzodioxaphosphorin-4-one (150 mg, 0.8 mmol) in dioxane (1.5 mL) at RT. After 15 min a mixture of tributylammonium pyrophosphate in DMF (0.2 M, 6 mL, 1.2 mmol) and tributylamine (0.7 mL, 2.8 mmol) was added. After 20 min a solution of iodine (210 mg, 0.8 mmol) and water (0.32 mL) in pyridine (16 mL) was added. After 20 min the reaction was quenched by the addition of aqueous $Na_2SO_3$ (5%, 0.5 mL) and acetone (0.5 mL). The solvents were removed in vacuo. Water (30 mL) was added, and the mixture was filtered (0.2 μm). Purification by ion-exchange HPLC (Dionex BioLC DNAPac PA-100, 22×250 mm, eluent A=water, eluent B=1 M aq. $NH_4HCO_3$, gradient from 0 to 25% B in 16 min, flow rate=10 mL/min, Rt=14 min), followed by reverse phase HPLC (Waters Prep Nova-Pak HR C18 column, 60 Å, 19×300 mm, eluent A=25 mM TEAA pH 7, eluent B=50% $CH_3CN$ in A, gradient from 0 to 70% B in 20 min, flow rate=5 mL/min, Rt=18 min) gave 3'-O—(N-acetone-oxime)-2'-deoxycytidine-5'-triphosphate as a colorless foam after lyophilization. The yield was determined by UV (260 nm, ext. coeff.=7300 $Lmol^{-1}$ $cm^{-1}$) to be 225 μmol (38%).

$^1$H-NMR ($D_2O$, 300 MHz): ∂ (ppm, rel to HDO=4.65)= 1.77 (s, 3H); 1.79 (s, 3H); 2.12-2.22 (m, 1H); 2.40-2.50 (m, 1H); 4.00-4.16 (m, 2H); 4.28-4.33 (m, 1H); 4.76-4.80 (m, 1H); 6.09 (d, J=7.7 Hz, 1H); 6.18 (dd, J=5.7, 8.4 Hz, 1H); 7.23 (br. s, 2H); 7.96 (d, J=7.7 Hz, 1H). $^{31}$P-NMR ($D_2O$, 120 MHz): ∂ (ppm, rel to external H3PO4=0)=−10.9 (d, J=19.5 Hz, 1P); −11.4 (d, J=19.5 Hz, 1P); −23.3 (t, J=19.5 Hz, 1P).

3'-O-Amino-2'-deoxycytidine-5'-triphosphate (2f)

To a solution of 3'-O—(N-acetone-oxime)-2'-deoxycytidine-5'-triphosphate (2e, 100 μmol) in water (10 mL) was added aqueous sodium acetate buffer (1 M, pH 4.0, 2 mL, 2 mmol) and aqueous hydroxylamine solution (50 wt-%, 100 μL, ca. 1.6 mmol). After 2 h at RT, the reaction was diluted with water (20 mL) and filtered (0.2 μm). Purification by ion-exchange HPLC (Dionex BioLC DNAPac PA-100, 22×250 mm, eluent A=water, eluent B=1 M aq. $NH_4HCO_3$, gradient from 0 to 30% B in 20 min, flow rate=10 mL/min, Rt=16 min) gave 2f as a colorless foam after lyophilization (74%, by UV, (260 nm, ext. coeff.=7300 $Lmol^{-1}$ $cm^{-1}$).

$^1$H-NMR ($D_2O$, 300 MHz): ∂ (ppm, rel to HDO=4.65)= 2.09-2.16 (m, 1H); 2.40-2.50 (m, 1H); 4.00-4.10 (m, 2H); 4.25-4.30 (m, 1H); 4.40-4.45 (m, 1H); 6.02 (d, J=6.5 Hz, 1H); 6.14 (dd, J=6.0, 7.9 Hz, 1H); 7.85 (d, J=6.5 Hz, 1H). $^{31}$P-NMR ($D_2O$, 120 MHz): ∂ (ppm, rel to external $H_3PO_4$=0)=−10.2 (br, 1P); −11.3 (br, 1P); −22.9 (br, 1P).

Example 3

Figure 4:
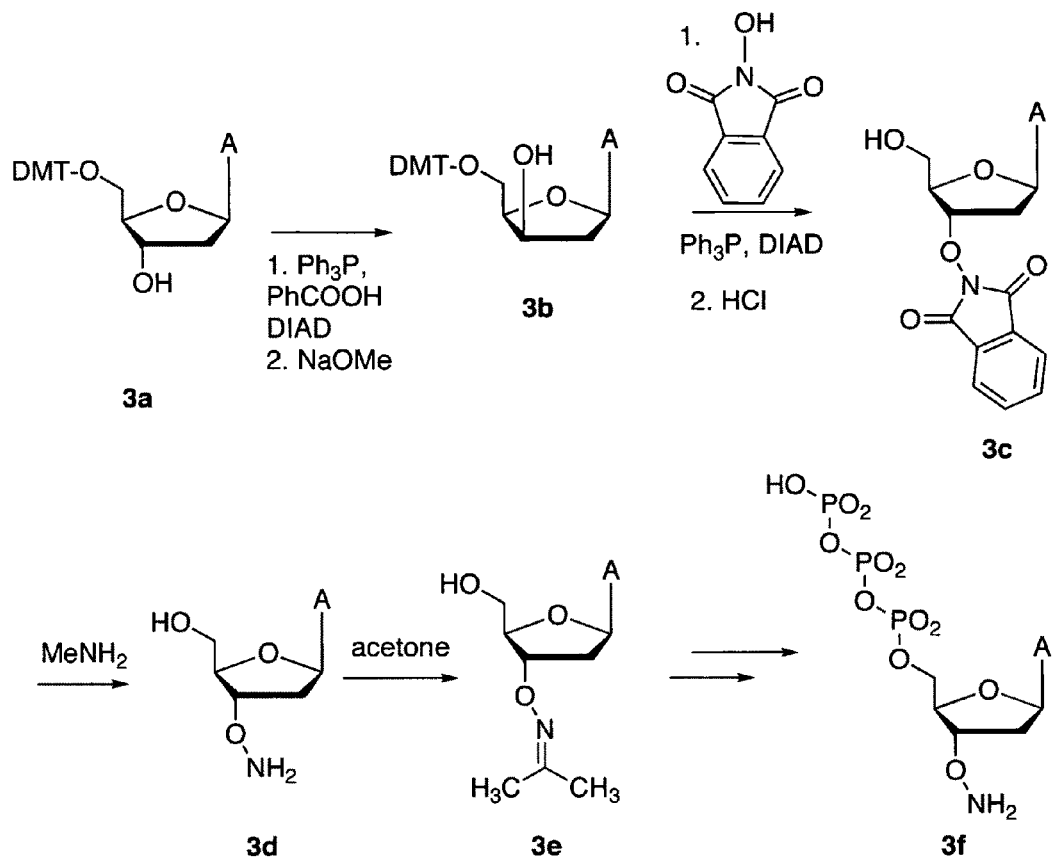

Synthesis of dATP-ONH$_2$ (FIG. 4)

5'-O-Dimethoxytrityl-xylo-2'-deoxyadenosine (3b)

To a solution of 5'-O-dimethoxytrityl-2'-deoxyadenosine (3a, 8.3 g, 15 mmol), benzoic acid (3.0 g, 24 mmol) and triphenylphosphine (6.5 g, 24 mmol) in THF (250 mL) was added DIAD (4.5 mL, 24 mmol) at RT. After 1 h the reaction was quenched by the addition of MeOH (5 mL). The solvents were removed in vacuo. Purification by FLC (silica, gradient 3 to 5% MeOH in $CH_2Cl_2$) gave 3'-O-benzoyl-5'-O-dimethoxytrityl-xylo-2'-deoxyadenosine (12 g) as a colorless foam which, according to NMR, contained some triphenylphosphine oxide as well as some elimination product (2',3'-olefin). This intermediate was redissolved in MeOH (300 mL) and treated with a solution of sodium methoxide in MeOH (5.3 M, 4 mL, 21 mmol). After 16 h at RT, the reaction was quenched by the addition of AcOH (glacial, 1.5 mL). The solvents were removed in vacuo. Purification by FLC (silica, gradient 3 to 10% MeOH in $CH_2Cl_2$) gave 5'-O-dimethoxytrityl-xylo-2'-deoxyadenosine (3.7 g; 45% overall) as a colorless foam.

$^1$H-NMR ($d_6$-DMSO, 300 MHz): ∂ (ppm)=2.26-2.34 (m, 1H); 2.74-2.84 (m, 1H); 3.18-3.25 (m, 1H); 3.34-3.42 (m, 1H); 3.70-3.74 (2s, 6H); 4.17-4.22 (m, 1H); 4.31-4.36 (m, 1H); 5.95 (d, J=5.7 Hz, 1H); 6.35 (dd, J=1.0, 7.8 Hz, 1H); 6.77-6.86 (m, 4H); 7.16-7.44 (m, 11H); 8.16 (s, 1H); 8.27 (s, 1H). $^{13}$C-NMR ($d_6$-DMSO, 75 MHz): ∂ (ppm)=40.6; 55.0; 55.0; 63.1; 69.6; 82.9; 83.6; 85.5; 113.1; 119.0; 126.6; 127.7; 127.7; 129.7; 135.6; 135.8; 139.8; 145.0; 148.6; 152.3; 156.1; 158.0; 158.0.

3'-O-Phthalimido-2'-deoxyadenosine (3c)

To a solution of 5'-O-dimethoxytrityl-xylo-2'-deoxyadenosine (3b, 3.4 g, 6 mmol), N-hydroxy-phthalimide (1.6 g, 10 mmol) and triphenylphosphine (2.6 g, 10 mmol) in THF (120 mL) was added DIAD (1.9 mL, 10 mmol) at RT. After 1 h the reaction was quenched by the addition of MeOH (3 mL). The solvents were removed in vacuo. Purification by FLC (silica, gradient 3 to 5% MeOH in $CH_2Cl_2$) gave 5'-O-dimethoxytrityl-3'-O-phthalimido-2'-deoxyadenosine (6.2 g) as a colorless foam which, according to NMR, contained significant amounts of triphenylphosphine oxide and some elimination product (2',3'-olefin). This intermediate was redissolved in MeOH (30 mL) and treated with methanolic HCl (1.25 M, 55 mL, ca. 70 mmol) at RT. Within minutes, product started to precipitate. After 10 minutes, solids were removed by filtration and dried at high vacuum to give 3c (1.5 g, 63% overall) as an off-white powder.

$^1$H-NMR ($d_6$-DMSO, 300 MHz): ∂ (ppm)=2.62-3.02 (m, 2H); 3.60-3.66 (m, 2H); 4.37-4.41 (m, 1H); 5.13-5.18 (m, 1H); 6.59 (dd, J=6.2, 7.2 Hz, 1H); 7.91 (s, 4H); 8.58 (s, 1H); 8.78 (s, 1H); 8.97 (br s, 1H); 9.60 (br s, 1H). $^{13}$C-NMR ($d_6$-DMSO, 75 MHz): ∂ (ppm)=36.1; 61.2; 83.8; 84.1; 88.0; 118.5; 123.4; 128.7; 134.9; 142.0; 145.2; 148.1; 150.4; 163.8.

3'-O—(N-Acetone-oxime)-2'-deoxyadenosine (3e)

3'-O-Phthalimido-2'-deoxyadenosine (3c, 790 mg, 2.0 mmol) was dissolved in aqueous methylamine solution (4%, 22 mL, ca. 24 mmol). After 20 min, most of the methylamine was removed in vacuo, and the remaining solution was treated with acetone (3 mL). After 3 h at RT, the solvent was removed in vacuo. The residue was redissolved in water (35 mL) and $CH_3CN$ (15 mL), and the mixture was filtered (0.2 μm). Purification by reverse phase HPLC (Waters Prep Nova-Pak HR C18 column, 60 Å, 19×300 mm, eluent A=25 mM TEAA pH 7, eluent B=CH3CN, gradient from 25 to 50% B in 7 min, then to 80% B in 8 min, flow rate=5 mL/min, Rt=14 min) gave 3'-O—(N-acetone-oxime)-2'-deoxyadenosine (465 mg; 76%) as a colorless foam after lyophilization.

$^1$H-NMR ($d_6$-DMSO, 300 MHz): ∂ (ppm)=1.86 (s, 3H); 1.87 (s, 3H); 2.47-2.55 (m, 1H); 2.82-2.93 (m, 1H); 3.54-3.72 (m, 2H); 4.11-4.16 (m, 1H); 4.81-4.85 (m, 1H); 5.43 (dd, J=4.7, 7.0 Hz, 1H); 6.33 (dd, J=5.9, 8.9 Hz, 1H); 7.34 (br. s, 2H); 8.13 (s, 1H); 8.35 (s, 1H). $^{13}$C-NMR ($d_6$-DMSO, 75 MHz): ∂ (ppm)=15.5; 21.5; 36.4; 62.2; 82.5; 84.4; 84.9; 119.3; 139.6; 148.8; 152.3; 155.9; 156.2.

3'-O—(N-Acetone-oxime)-2'-deoxyadenosine-5'-triphosphate

To a suspension of 3'-O—(N-acetone-oxime)-2'-deoxyadenosine (3e, 180 mg, 0.6 mmol) in pyridine (2 mL), dioxane (1.5 mL) and DMF (1 mL) was added a solution of 2-chloro- 4H-1,3,2-benzodioxaphosphorin-4-one (150 mg, 0.8 mmol) in dioxane (1.5 mL) at RT, leading to a clear solution. After 15 min a mixture of tributylammonium pyrophosphate in DMF (0.2 M, 6 mL, 1.2 mmol) and tributylamine (0.7 mL, 2.8 mmol) was added. After 20 min a solution of iodine (210 mg, 0.8 mmol) and water (0.32 mL) in pyridine (16 mL) was added. After 20 min, the reaction was quenched by the addition of aqueous $Na_2SO_3$ (5%, 0.5 mL) and acetone (0.5 mL). The solvents were removed in vacuo. Water (40 mL) was added, and the mixture was filtered (0.2 μm). Purification by ion-exchange HPLC (Dionex BioLC DNAPac PA-100, 22×250 mm, eluent A=water, eluent B=1 M aq. $NH_4HCO_3$, gradient from 0 to 25% B in 16 min, flow rate=10 mL/min, Rt=13 min), followed by reverse phase HPLC (Waters Prep Nova-Pak HR C18 column, 60 Å, 19×300 mm, eluent A=25 mM TEAA pH 7, eluent B=50% $CH_3CN$ in A, gradient from 0 to 100% B in 20 min, flow rate=5 mL/min, Rt=18 min) gave 3'-O—(N-acetone-oxime)-2'-deoxyadenosine-5'-triphosphate as a colorless foam after lyophilization. The yield was determined by UV (260 nm, ext. coeff.=15400 $Lmol^{-1} cm^{-1}$) to be 240 μmol (40%).

$^1$H-NMR ($D_2O$, 300 MHz): ∂ (ppm, rel to HDO=4.65)=1.78 (s, 3H); 1.83 (s, 3H); 2.55-2.78 (m, 2H); 3.97-4.13 (m, 2H); 4.32-4.37 (m, 1H); 4.90-4.95 (m, 1H); 6.33 (dd, J=5.8, 9.0 Hz, 1H); 8.03 (s, 1H); 8.37 (s, 1H). $^{31}$P-NMR ($D_2O$, 120 MHz): ∂ (ppm, rel to external $H_3PO_4$=0)=−10.4 (d, J=19.5 Hz, 1P); −11.4 (d, J=19.5 Hz, 1P); −23.2 (t, J=19.5 Hz, 1P).

3'-O-Amino-2'-deoxyadenosine-5'-triphosphate (3f)

To a solution of 3'-O—(N-acetone-oxime)-2'-deoxyadenosine-5'-triphosphate (100 μmol) in water (10 mL) was added aqueous sodium acetate buffer (1M, pH 4.0, 2 mL, 2 mmol) and aqueous hydroxylamine solution (50 wt-%, 100 μL, ca. 1.6 mmol). After 2 h at RT, the reaction was diluted with water (20 mL) and filtered (0.2 μm). Purification by ion-exchange HPLC (Dionex BioLC DNAPac PA-100, 22×250 mm, eluent A=water, eluent B=1 M aq. $NH4HCO3$, gradient from 0 to 30% B in 20 min, flow rate=10 mL/min, Rt=15 min) gave 3f as a colorless foam after lyophilization. The yield was determined by UV (260 nm, ext. coeff.=15400 $Lmol^{-1} cm^{-1}$) to be 65 μmol (65%).

$^1$H-NMR ($D_2O$, 300 MHz): ∂ (ppm, rel to HDO=4.65)=2.36-2.43 (m, 1H); 2.57-2.63 (m, 1H); 3.93-4.10 (m, 2H); 4.29-4.34 (m, 1H); 4.50-4.54 (m, 1H); 6.28 (dd, J=7.0, 8.0 Hz, 1H); 8.04 (s, 1H); 8.33 (s, 1H). $^{31}$P-NMR ($D_2O$, 120 MHz): ∂ (ppm, rel to external $H_3PO_4$=0)=−8.8 (d, J=19.5 Hz, 1P); −11.2 (d, J=19.5 Hz, 1P); −22.6 (t, J=19.5 Hz, 1P).

Example 4

Figure 5:
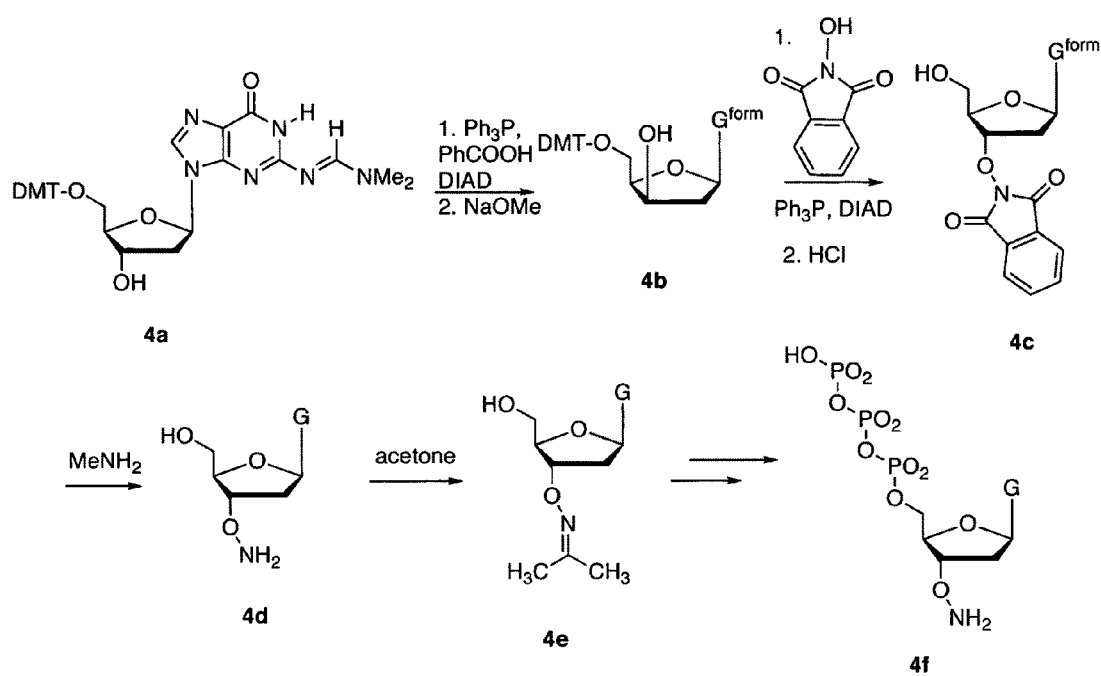

Synthesis of dGTP-ONH2 (FIG. 5)

5'-O-Dimethoxytrityl-N2-dimethylaminomethylidene-xylo-2'-deoxyguanosine (4b)

To a solution of 5'-O-dimethoxytrityl-N2-dimethylaminomethylidene-2'-deoxyguanosine (4a, 9.4 g, 15 mmol), benzoic acid (3.0 g, 24 mmol) and triphenylphosphine (6.5 g, 24 mmol) in THF (250 mL) was added DIAD (4.5 mL, 24 mmol) at RT. After 30 min the reaction was quenched by the addition of MeOH (2 mL). The solvents were removed in vacuo. This intermediate was redissolved in MeOH (600 mL) and treated with a solution of sodium methoxide in MeOH (5.3 M, 7.6 mL, 40 mmol). After 16 h at RT, the reaction was quenched by the addition of AcOH (glacial, 2.3 mL, 40 mmol). The solvents were removed in vacuo. Purification by FLC (silica, gradient 0 to 10% MeOH in $CH_2Cl_2$) gave 5'-O-dimethoxytrityl-N2-dimethylaminomethylidene-xylo-2'-deoxyguanosine (5.6 g; 50% overall) as a colorless foam.

$^1$H-NMR ($d_6$-DMSO, 300 MHz): ∂ (ppm)=2.18-2.26 (m, 1H); 2.69-2.80 (m, 1H); 3.03 (s, 3H); 3.11 (s, 3H); 3.19-3.25 (m, 1H); 3.34-3.40 (m, 1H); 3.70-3.74 (2s, 6H); 4.16-4.20 (m, 1H); 4.32-4.37 (m, 1H); 5.57-5.61 (m, 1H); 6.29 (dd, J=1.5, 8.4 Hz, 1H); 6.80-6.86 (m, 4H); 7.16-7.44 (m, 9H); 8.00 (s, 1H); 8.54 (s, 1H); 11.38 (s, 1H). $^{13}$C-NMR ($d_6$-DMSO, 75 MHz): ∂ (ppm)=34.6; 40.6; 40.9; 55.0; 55.0; 63.2; 69.4; 82.0; 83.5; 85.5; 113.1; 119.4; 126.6; 127.7; 129.7; 129.8; 135.6; 135.7; 137.3; 145.0; 149.4; 157.3; 157.7; 157.9; 158.0; 158.0.

5'-O-Dimethoxytrityl-N2-dimethylaminomethylidene-3'-O-phthalimido-2'-deoxyguanosine (4c)

To a solution of 5'-O-dimethoxytrityl-N2-dimethylaminomethylidene-xylo-2'-deoxyguanosine (4.7 g, 7.5 mmol), N-hydroxy-phthalimide (2.1 g, 13 mmol) and triphenylphosphine (3.4 g, 13 mmol) in THF (150 mL) was added DIAD (2.5 mL, 13 mmol) at RT. After 1 h the reaction was quenched by the addition of MeOH (2 mL). The solvents were removed in vacuo. Purification by FLC (silica, gradient 3 to 10% MeOH in CH2Cl2) gave 5'-O-dimethoxytrityl-N2-dimethylaminomethylidene-3'-O-phthalimido-2'-deoxyguanosine (5.3 g) as a colorless foam which, according to NMR, contained ca 0.25 equivalents of elimination product (2',3'-olefin). An analytical sample was repurified by reverse phase HPLC (Waters Prep Nova-Pak HR C18 column, 60 Å, 19×300 mm, eluent A=25 mM TEAA pH 7, eluent B=$CH_3CN$, gradient from 50% to 90% B in 18 min, then constant 90% B for 6 min, flow rate=5 mL/min, Rt=22 min) to give a colorless foam after lyophilization.

$^1$H-NMR ($CDCl_3$, 300 MHz): ∂ (ppm)=2.64-2.74 (m, 1H); 2.84-2.94 (m, 1H); 3.09 (s, 3H); 3.16 (s, 3H); 3.31-3.45 (m, 2H); 3.75 (s, 6H); 4.56-4.61 (m, 1H); 5.12-5.16 (m, 1H); 6.53 (dd, J=5.5, 8.6 Hz, 1H); 6.72-6.78 (m, 4H); 7.12-7.36 (m, 10H); 7.72-7.85 (m, 5H); 8.67 (s, 1H); 10.11 (s, 1H). $^{13}$C-NMR ($CDCl_3$, 75 MHz): ∂ (ppm)=35.3; 41.5; 55.3; 63.6; 82.6; 83.6; 86.7; 88.7; 113.3; 120.4; 123.9; 127.0; 128.0; 128.1; 128.7; 130.0; 130.1; 135.0; 135.5; 135.9; 144.4; 150.4; 157.1; 158.5; 158.6; 158.6; 164.0.

3'-O—(N-acetone-oxime)-2'-deoxyguanosine (4e)

To a solution of 5'-O-dimethoxytrityl-N2-dimethylaminomethylidene-3'-O-phthalimido-2'-deoxyguanosine (4c, 900 mg, ca. 1 mmol phthalimido-compound, contains ca. 0.25 eq. 2',3'-olefin) in MeOH (7 mL) was added aqueous HCl (conc, 0.4 mL, ca 5 mmol) and TFA (0.1 mL, ca 1.5 mmol). The mixture was shaken for 5 min at RT, leading to a clear solution. Ammonium hydroxide (30%, 5 mL, ca 80 mmol) was added, and the resulting suspension was stirred for 1 h. Aqueous methylamine solution (10%, 13 mL, ca. 36 mmol) was added. After 20 min, the supernatant was filtered off and most of the methylamine and ammonia was removed in vacuo. The remaining solution was neutralized with dilute aqueous HCl and treated with acetone (3 mL) and $CH_3CN$ (5 mL). After 3 h at RT, the mixture was diluted with water (20 mL) and $CH_3CN$ (20 mL) and filtered (0.2 μm). Purification by reverse phase HPLC (Waters Prep Nova-Pak HR C18 column, 60 Å, 19×300 mm, eluent A=25 mM TEAA pH 7, eluent B=$CH_3CN$, gradient from 25 to 50% B in 5 min, then to 80% B in 12 min, flow rate=5 mL/min, Rt=13 min) gave 3'-O—(N-acetone-oxime)-2'-deoxyguanosine (120 mg; 37%) as a colorless foam after lyophilization.

¹H-NMR (d₆-DMSO, 300 MHz): ∂ (ppm)=1.84 (s, 3H); 1.85 (s, 3H); 2.41-2.50 (m, 1H); 2.62-2.72 (m, 1H); 3.52-3.64 (m, 2H); 4.02-4.08 (m, 1H); 4.74-4.78 (m, 1H); 5.05-5.12 (m, 1H); 6.09 (dd, J=5.7, 8.9 Hz, 1H); 6.51 (br. s, 2H); 7.95 (s, 1H); 10.60 (br. s, 1H).

3'-O—(N-acetone-oxime)-2'-deoxyguanosine-5'-triphosphate. To a suspension of 3'-O—(N-acetone-oxime)-2'-deoxyguanosine (100 mg, 0.3 mmol) in pyridine (1 mL), dioxane (0.8 mL) and DMF (1 mL) was added a solution of 2-chloro-4H-1,3,2-benzodioxaphosphorin-4-one (75 mg, 0.4 mmol) in dioxane (0.75 mL) at RT, leading to a clear solution. After 15 min a mixture of tributylammonium pyrophosphate in DMF (0.2 M, 3 mL, 0.6 mmol) and tributylamine (0.35 mL, 1.4 mmol) was added. After 20 min a solution of iodine (100 mg, 0.4 mmol) and water (0.16 mL) in pyridine (8 mL) was added. After 20 min the reaction was quenched by the addition of aqueous Na2SO3 (5%, 0.5 mL) and acetone (0.5 mL). The solvents were removed in vacuo. Water (30 mL) was added, and the mixture was filtered (0.2 μm). Purification by ion-exchange HPLC (Dionex BioLC DNAPac PA-100, 22×250 mm, eluent A=water, eluent B=1 M aq. NH4HCO3, gradient from 0 to 25% B in 16 min, flow rate=10 mL/min, Rt=16 min), followed by reverse phase HPLC (Waters Prep Nova-Pak HR C18 column, 60 Å, 19×300 mm, eluent A=25 mM TEAA pH 7, eluent B=50% CH3CN in A, gradient from 0 to 100% B in 20 min, flow rate=5 mL/min, Rt=18 min) gave 3'-O—(N-acetone-oxime)-2'-deoxyguanosine-5'-triphosphate as a colorless foam after lyophilization. The yield was determined by UV (260 nm, ext. coeff.=11700 Lmol$^{-1}$ cm$^{-1}$) to be 135 μmol (45%).

¹H-NMR (D₂O, 300 MHz): ∂ (ppm, rel to HDO=4.65)= 1.78 (s, 3H); 1.81 (s, 3H); 2.45-2.55 (m, 1H); 2.65-2.80 (m, 1H); 4.00-4.13 (m, 2H); 4.27-4.32 (m, 1H); 4.87-4.92 (m, 1H); 6.14 (dd, J=5.8, 9.0 Hz, 1H); 7.98 (s, 1H). ³¹P-NMR (D₂O, 120 MHz): ∂ (ppm, rel to external H₃PO₄=0) =−9.7 (d, J=19.5 Hz, 1P); −11.4 (d, J=19.5 Hz, 1P); −23.1 (t, J=19.5 Hz, 1P).

3'-O-Amino-2'-deoxyguanosine-5'-triphosphate (4f). To a solution of 3'-O—(N-acetone-oxime)-2'-deoxyguanosine-5'-triphosphate (50 μmol) in water (5 mL) was added aqueous sodium acetate buffer (1M, pH 4.0, 1 mL, 1 mmol) and aqueous hydroxylamine solution (50 wt-%, 50 μL, ca. 0.8 mmol). After 2 h at RT, the reaction was diluted with water (10 mL) and filtered (0.2 μm). Purification by ion-exchange HPLC (Dionex BioLC DNAPac PA-100, 22×250 mm, eluent A=water, eluent B=1 M aq. NH4HCO3, gradient from 0 to 30% B in 20 min, flow rate=10 mL/min, Rt=18 min) gave 3'-O-amino-2'-deoxyguanosine-5'-triphosphate as a colorless foam after lyophilization. The yield was determined by UV (260 nm, ext. coeff.=11700 Lmol$^{-1}$ cm$^{-1}$) to be 36 μmol (72%).

¹H-NMR (D₂O, 300 MHz): ∂ (ppm, rel to HDO=4.65)= 2.50-2.75 (m, 2H); 3.97-4.13 (m, 2H); 4.29-4.34 (m, 1H); 4.55-4.60 (m, 1H); 6.08-6.16 (m, 1H); 8.00 (s, 1H). ³¹P-NMR (D₂O, 120 MHz): ∂ (ppm, rel to external H₃PO₄=0)=−10.6 (br, 1P); −11.2 (br, 1P); −23.0 (br, 1P).

Example 5

Figure 6:
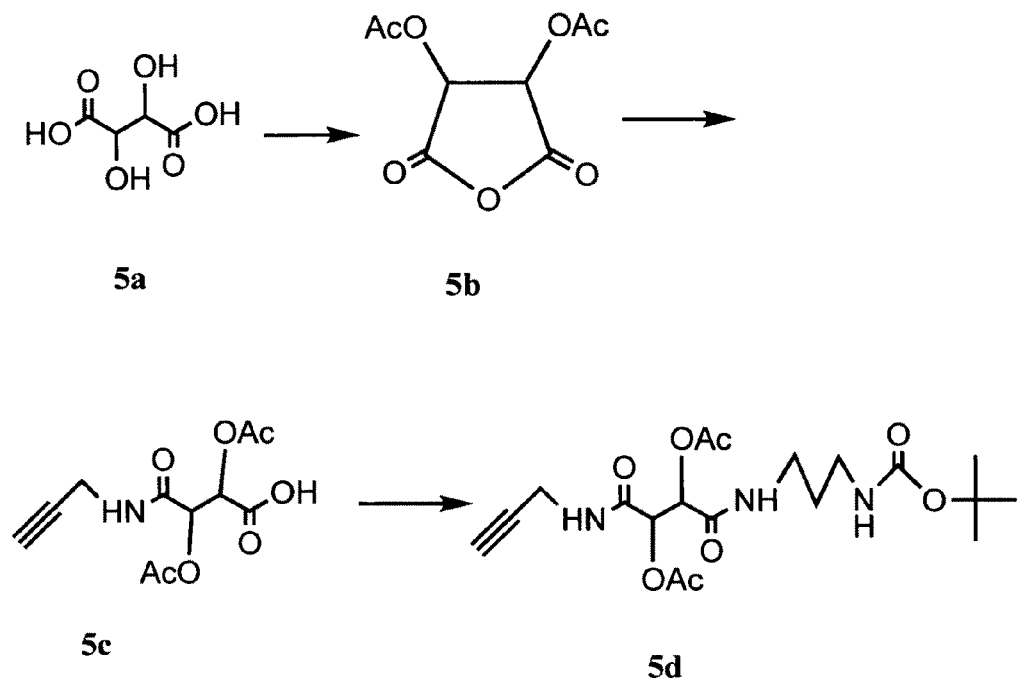

Synthesis of Linker Component (FIG. 6)

(R,R)-Diacetyltartaric acid anhydride (5b). To a mixture of finely powdered tartaric acid (5a, 5.48 g, 36.6 mmol) in acetic anhydride (12 mL) was added concentrated sulfuric acid (0.2 mL) with stirring at RT. After the release of heat stopped, the solution was gently refluxed for 10 min and then cooled to 0° C. The crystalline product thus formed was collected by filtration and washed with benzene. This crude product was stirred with 16 mL of diethyl ether at 0° C. for 10 min, filtered, washed with diethyl ether, and dried to afford 5.82 g (74%) of the anhydride.

(R,R))—N-Propragyl amine diacetyltartaric acid monoamide (5c)

To a solution of (R,R)-diacetyltartaric acid anhydride (8.0 g, 34 mmol) in 60 mL of CH₂Cl₂ was added propragyl amine (2.3 mL, 37 mmol) at 0° C. under an atmosphere of Ar. After the solution had been stirred at this temperature overnight, the solvent was removed under reduced pressure. The solid obtained was washed with diethyl ether (4.×50 mL) and filtered. Drying on high vacuum gave 5c (8.0 g) as a solid.

(R,R)—N-(Propragyl amine)-N'-Boc-ethylenediamine diacetyltartramide (5d)

A mixture of di-N-succinimidyl oxalate (1.7 g, 6 mmol), the monoamide 5c (2.3 g, 6.11 mmol), and pyridine (0.5 mL, 6.11 mmol) in 100 mL of acetonitrile was stirred at RT for 12 h under Ar. The resulting solution, almost clear, was cooled to 0° C. To this was added a mixture of N-Boc-ethylenediamine (961 mg, 6.0 mmol) and triethylamine (0.8 mL, 6.0 mmol) in 15 mL of acetonitrile. The mixture was stirred at this temperature for 1.5 h, and then EtOAc (350 mL) and water (50 mL) were added. The layers were separated and the organic layer was dried over anhydrous Na₂SO₄. The solvents were removed under reduced pressure and the residue was purified by preparative silica gel (30 g) chromatography with a CH₂Cl₂-MeOH (100:7 v/v) mixture as eluent to yield the pure diamide (5d, 2.0 g) as a yellowish white solid.

¹H NMR(CdCl₃:Me₂SO-d₆, 20:1): 7.6(1H, br s, NH), 7.4 (1H, br s, NH), 5.6 (1H, s, NH), 5.544 (1H, d, J=3.8 Hz, CH), 5.58 (1H, d, J=3.8 Hz, CH), 3.79-4.1 (2H, m, CH₂), 3.1-3.3 (4H, m, CH₂), 2.1 (1H, m, CH), 2.05 (3H, s, CH₃), 2.07(3H, s, CH₃), 1.38 (9H, s, CH₃)

Example 6

Figure 7:
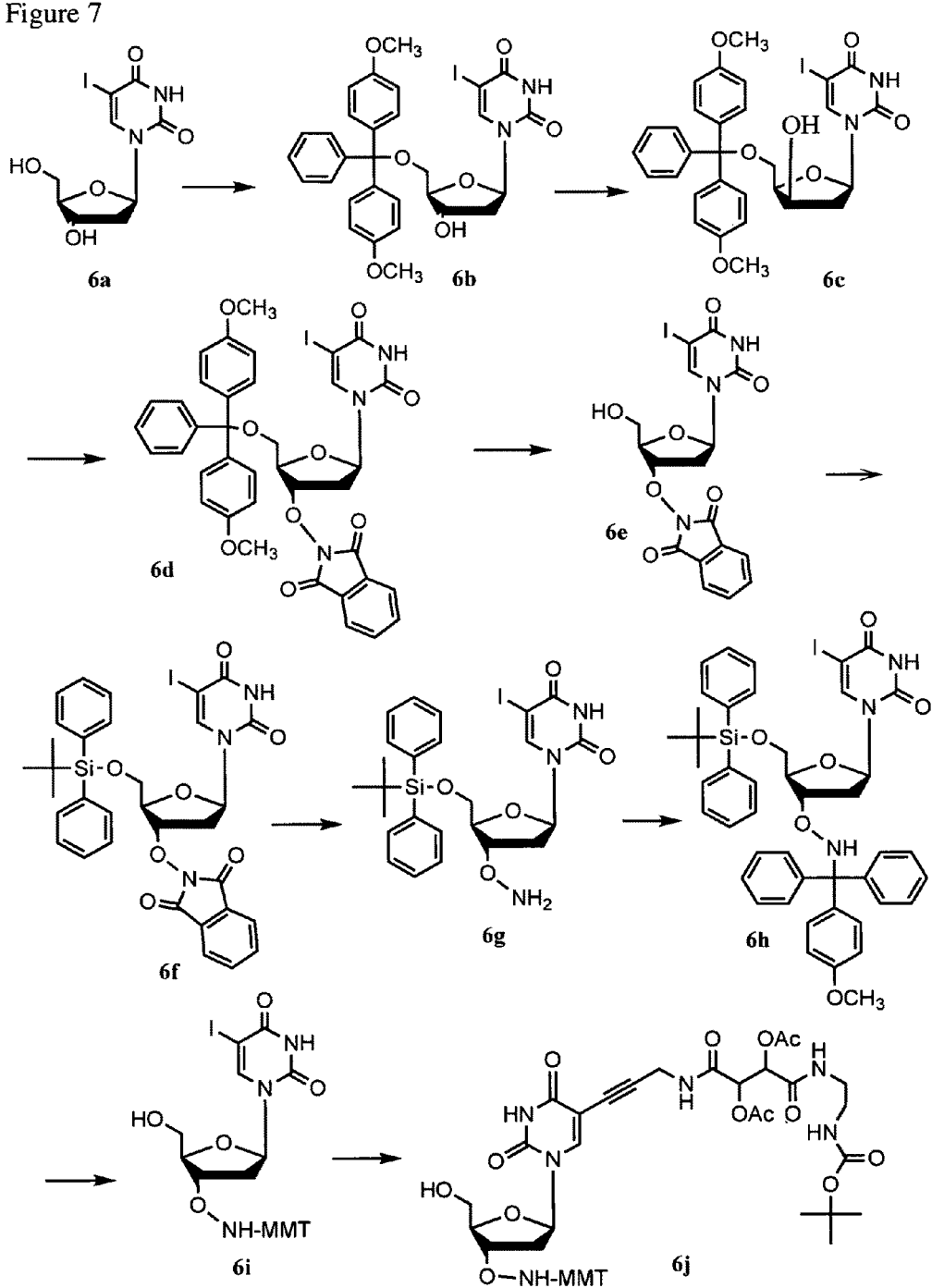
Figure 8:
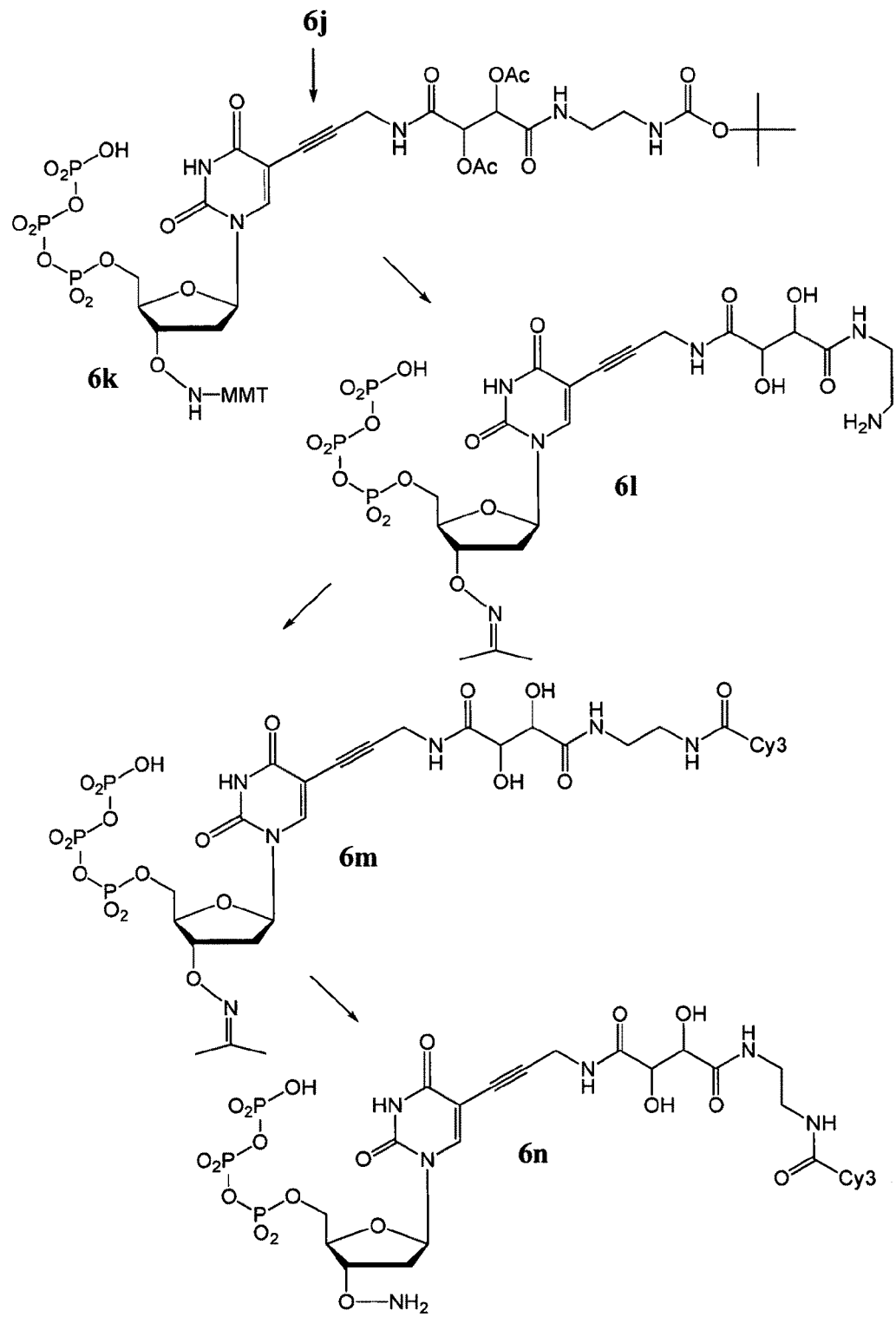

Thymidine Analog with an acetylene linker and a Cy3-fluor (FIGS. 7 and 8)

5'-Dimethoxytrityl-xylo-5-iodouridine (6c)

A solution of 2'-deoxy-5-iodouridine (6a, 5 g; 14.125 mmol), triethylamine (2.35 mL; 16.95 mmol) and N,N-dimethylaminopyridine (517 mg; 4.23 mmol) in pyridine (40 mL) was cooled to 0° C. A separate solution of 4,4'-dimethoxytrityl chloride (5.75 g; 16.95 mmol) in pyridine (40 mL) was added quickly and the resulting suspension was allowed to warm to RT overnight. Then the suspension was cooled to 0° C., and triethylamine (6 mL; 42 mmol) and methanesulfonyl chloride (2 mL; 21 mmol) were added. The red suspension was allowed to warm to RT. After 2 h the suspension was filtered and the solids were washed with EtOAc (100 mL). The combined filtrate was concentrated in vacuo to give 6b as a brown foam. Crude 6b was re-dissolved in a mixture of EtOH (140 mL) and aqueous NaOH (1 M, 70 mL; 70 mmol). After being heated under reflux for 90 min, the mixture was treated with aqueous HCl (1 M, 40 mL, 40 mmol). The EtOH was removed in vacuo and the remaining suspension was partitioned between CH₂Cl₂ (100 mL) and brine (20 mL). The organic phase was dried (Na₂SO₄) and concentrated in vacuo.

The crude product was resolved by flash column chromatography (silica; gradient 0-5% MeOH in CH$_2$Cl$_2$) giving 6c as a colorless powder (9 g, 99%).

$^1$H-NMR (CDCl$_3$, 300 MHz): ∂ (ppm)=1.42 (s, 1H); 2.12-2.18 (m, 1H); 2.50-2.61 (m, 1H); 3.45-3.66 (m, 2H); 3.79 (s, 6H); 4.02-4.07 (m, 1H); 4.43-4.47 (m, 1H); 6.15 (dd, J=8.0, 1.8 Hz, 1H); 6.84-6.88 (m, 4H); 7.20-7.46 (m, 9H); 8.25 (s, 1H).

3'-O-Phthalimidoyl-5-iodouridine (6e)

To a solution of compound 6c (9.5 g; 14.47 mmol), triphenylphosphine (4.2 g; 16 mmol) and N-hydroxyphthalimide (2.6 g; 16 mmol) in tetrahydrofuran (100 mL) was added N,N'-diisopropyl azodicarboxylate (3.5 mL; 18 mmol) at 0° C. The resulting orange suspension was allowed to warm to RT overnight, during which time it clarified. The mixture was treated with water (0.6 mL) and the solvent was removed in vacuo. Most byproducts were removed by flash column chromatography (silica; gradient 50% hexanes in EtOAc to pure EtOAc), giving a mixture (10 g) containing mostly 6d (EtOAc:Hex=2:1; Rf=0.37) together with some triphenylphosphine oxide. This mixture was suspended in MeOH (750 mL) and treated with concentrated aqueous HCl (37.5 mL; ca 450 mmol). The clear solution was cooled to −20° C. overnight, yielding compound 6e as slightly orange precipitate (1.83 g; 25%).

$^1$H-NMR (d$_6$-DMSO, 300 MHz): ∂ (ppm)=2.29-2.39 (m, 1H); 2.56-2.60 (m, 1H); 3.64-3.67 (m, 2H); 4.28-4.32 (m, 1H); 4.90-5.00 (m, 1H); 5.29 (t, J=4.9 Hz, 1H); 6.30 (dd, J=8.3, 5.8 Hz, 1H); 7.88 (s, 4H); 8.39 (s, 1H); 11.72 (s, 1H).

1-(5'-O-tert-Butyldiphenylsilyl-3'-O-phthalimidoyl-2'-deoxy-5-iodouracil (6f)

Compound 6e (1.8 g, 3.66 mmol) was thoroughly dried by coevaporation twice with 25 mL of toluene on a rotary evaporator in 100 mL round bottom flask. Anhydrous DMF (25 mL) was then added, followed by imidazole (1.45 g, 21 mmol). The mixture was stirred until all of the imidazole dissolved. Tert-butyldiphenylsilyl chloride (2.2 mL, 4.39 mmol) was then added, and the flask was flushed with nitrogen for 2 minutes. The mixture was then stirred overnight at RT, diluted with CH$_2$Cl$_2$ (100 mL) and extracted three times with water (each 50 mL) and once with saturated aqueous NaCl (50 mL). The organic layer was dried over anhydrous sodium sulfate, recovered by vacuum filtration, and concentrated by rotary evaporation. The resulting residue was purified by flash column chromatography on silica gel with hexane:EtOAc (1:1) to give 6f (2.1 g, 81%) as white solid.

3'-O-Amino-1-(5'-O-tert-butyldiphenylsilyl-2'-deoxy-5-iodouracil (6g)

Cold methylhydrazine (0.77 mL, 14.9 mmol) was added to a stirred solution of 6f (5.5 g, 7.45 mmol) in anhydrous CH$_2$Cl$_2$ at −5° C. to −10° C. After 10 minutes, a white precipitation of 1,2-dihydro-4-hydroxy-2-methyl-1-oxophthalizine was formed. The suspension was stirred at RT for 1 h. The precipitate was removed by filtration and was washed with CH$_2$Cl$_2$ (2×50 mL). The combined filtrates were concentrated by rotary evaporation and the residue purified by silica gel chromatography. Elution with hexane:EtOAc (1:1) gave 6g (4.4 g, 97%).

3'-O-Aminodimethoxytrityl-1-(5'-O-tert-butyldiphenylsilyl-2'-deoxy-5-iodouracil (6h)

Compound 6g (6.4 g, 7.57 mmol) was dried by azeotropic removal of water two times with pyridine (10 mL), with evaporation to dryness on a rotary evaporator each time. The residue was dissolved in anhydrous CH$_2$Cl$_2$ (25 mL). Diisopropylethylamine (3.1 mL, 18 mmol) and monomethoxytrityl chloride (4.7 g, 15.14 mmol) were then added. The progress of the reaction was monitored by TLC (hexane/EtOAc (2:1). After the reaction was complete, the mixture was diluted with CH$_2$Cl$_2$ (100 mL), the organic layer was washed with saturated sodium bicarbonate (50 mL) and water (50 mL), and then dried over sodium sulfate. The solvents were removed by rotary evaporation under vacuum, and the residue was purified by flash chromatography on silica gel (230-400 mesh) with 2:1-1:1 hexane:EtOAc to give 6h (7 g, 98%).

3'-O-Aminodimethoxytrityl-2'-deoxy-5-iodouracil (6i)

Compound 6h (7 g, 7.5 mmol) was dissolved in THF (20 mL) and treated with TBAF in THF (1 M, 20 mL). The reaction mixture was stirred for 2 h. at which time TLC showed that the reaction was complete. The reaction mixture was concentrated, diluted with CH$_2$Cl$_2$ (100 mL), and extracted with water (50 mL) and brine (50 mL). The aqueous extracts were back extracted with CH$_2$Cl$_2$ (100 mL), and the combined organic layers were dried over sodium sulfate and concentrated. The residue was fractionated by column chromatography (hexane:EtOAc, 2:1-1:1 to yield 6i (5 g, 95%)

$^1$H NMR (Me$_2$SO-d$_6$): 11.71 (1H, br s), 8.4 (1H, s), 8.1 (1H, s), 7.1-7.4 (10H, m), 6.7-6.8(4H, m), 6.1 (dd, 8.5, 5.8 Hz, 1H), 5.1 (1H, br s), 4.0-4.2 (1H, m), 3.8-4.0 (1H, m), 3.5-3.7 (2H, m), 2.33-2.4 (1H, m), 2.07-2.1 (1H, m)

Monomethoxytrityl-Protected Uridine Derivative with an acetylene diol linker (6j)

Compound 6i (1 g, 1.55 mmol) was dissolved in DMF (25 mL) and the solution was treated with CuI (59 mg, 0.31 mmol). The solution was degassed with Ar, and then treated successively with triethylamine (0.43 mL, 3.1 mmol), Boc linker (from above, 1.3 g, 3.1 mmol) and Pd(PPh$_3$)$_4$ (179.18 mg, 0.155 mmol). The resulting yellow solution was stirred for 3.0 h at RT. After complete conversion of the starting material was shown by TLC (CH$_2$Cl$_2$:MeOH, 9:1), the reaction was quenched with 5% EDTA (25 mL) and extracted with EtOAc. The organic layer was dried over sodium sulfate and concentrated to dryness by coevaporating with toluene. The residue was fractionated by column chromatography on silica (CH$_2$Cl$_2$:MeOH, 100:8) to give 6j (0.7 g, 50%).

$^1$H NMR (Me$_2$SO-d$_6$): 11.6 (1H, s), 8.7 (1H, m), 8.1-8.2 (2H, m, s), 7.2-7.4(10H, m), 7.1(2H, d, 8 Hz), 6.8 (2H, d, 6 Hz), 6.1 (dd, 8.6, 5.7 Hz, 1H), 5.4-5.5 (2H, m), 5.0 (1H,m), 4.0-4.2 (2H, m), 3.8-4.0 (4H, m), 3.75 (3H, s), 2.8-3.2 (4H, m), 2.2-2.3 (1H, m), 2.07 (3H,s), 2.1(3H,s), 1.3 (9H, s).

Triphosphate of dUTP-ONH$_2$ Carrying an acetylene diol linker (6k)

To a solution of 5'-OH nucleoside derivative 6j (3'-O—NH-MMTr, linker-di-OAc/NH-Boc) (930 mg, 1.0 mmol) in pyridine (4 mL) and dioxane (3.4 mL) was added a solution of 2-chloro-4H-1,3,2-benzodioxaphosphorin-4-one (260 mg, 1.4 mmol) in dioxane (2.6 mL) at RT. After 20 min a mixture of tributylammonium pyrophosphate in DMF (0.2 M, 14 mL, 2.8 mmol) and tributylamine (1.6 mL, 6.4 mmol) was added. After 20 min a solution of iodine (360 mg, 1.4 mmol) and water (0.56 mL) in pyridine (28 mL) was added. After 30 min the reaction was quenched by the addition of aqueous Na$_2$SO$_3$ (5%, 0.5 mL). The solvents were removed in vacuo. Water (50 mL) and CH$_3$CN (40 mL) was added, and the mixture was filtered (0.2 µm). Rough purification by reverse phase HPLC (Waters Prep Nova-Pak HR C$_{18}$ column, 60 Å, 19×300 mm, eluent A=water, eluent B=CH$_3$CN, gradient from 18 to 50% B in 25 min, then to 60% B in 5 min, then to 90% B in 2 min, then constant 90% B for 8 min, flow rate=5 mL/min, R$_t$=25-35 min) gave the fully protected triphosphate 6k (mixture of compounds due to partial loss of diol-acetates) as a colorless foam after lyophilization.

3'-O—(N-acetone-oxime)-2'-deoxyuridine-5'-triphosphate Carrying acetylene linker with diol and Primary Amine (6l)

Intermediate 6k was treated with NH$_4$OH (conc., 50 mL) for 4 h at RT and the mixture was lyophilized. The residue was treated with MeOH (0.5 mL) and TFA (9 mL) at RT for 2 min, resulting in a clear solution. Et$_2$O (75 mL) was added and the suspension was stored at −20° C. for 1 h. The precipitate was separated by centrifugation and the supernatant was decanted. The precipitate was redissolved carefully in aqueous NH$_4$HCO$_3$ buffer (200 mM, 45 mL) containing acetone (2 mL). The pH was adjusted to 6 by addition of dilute aqueous HCl, and the solution was let stand at RT for 2 h. The solvents were removed in vacuo. The residue was dissolved in water (45 mL), and the mixture was filtered (0.2 µm). Purification by ion-exchange HPLC (Dionex BioLC DNAPac PA-100, 22×250 mm, eluent A=water, eluent B=1 M aq. NH$_4$HCO$_3$, constant A for 2 min, then gradient from 0 to 18% B in 13 min, flow rate=10 mL/min, R$_t$=12-15 min), followed by reverse phase HPLC (Waters Prep Nova-Pak HR C$_{18}$ column, 60 Å, 19×300 mm, eluent A=25 mM TEAA pH 7, eluent B=50% CH$_3$CN in A, gradient from 0 to 100% B in 30 min, flow rate=5 mL/min, R$_t$=20 min) gave compound 6l as a colorless foam after lyophilization. The yield was determined by UV (291 nm, ext. coeff.=11000 Lmol$^{-1}$ cm$^{-1}$) to be 270 µmol (27% overall). Part of this material (ca 200 µmol) was transformed to the sodium salt by treatment with DOWEX-50WX-8 (Na$^+$) resin (10 g) in water (30 mL) for 3 h, followed by reverse phase HPLC purification, as above.

$^1$H-NMR (D$_2$O, 300 MHz): ∂ (ppm, rel to HDO=4.65)= 1.77 (s, 3H); 1.79 (s, 3H); 2.13-2.24 (m, 1H); 2.41-2.49 (m, 1H); 2.85-3.00 (m, 2H); 3.38-3.55 (m, 2H); 4.05-4.20 (m, 4H); 4.26-4.32 (m, 1H); 4.46 (s, 2H); 4.78-4.83 (m, 1H); 6.16 (dd, J=5.4, 8.8 Hz, 1H); 8.09 (s, 1H). $^{31}$P-NMR (D$_2$O, 120 MHz): ∂ (ppm, rel to external H$_3$PO$_4$=0)=−8.7 (d, J=19.5 Hz, 1P); −11.3 (d, J=19.5 Hz, 1P); −22.3 (t, J=19.5 Hz, 1P).

dUTP-ONH$_2$ carrying a Cy3-labelled acetylene diol linker (compound 6n). A solution of compound 6l (sodium salt, 20 µmol) in aqueous K$_2$HPO$_4$ (0.5 M, 0.6 mL) was mixed with a solution of Cy3-OSu (10 mg, ca. 12 µmol) in DMSO (0.8 mL) and acetone (0.4 mL). The mixture was incubated at RT in the dark for 2 h. The reaction mixture was diluted with water (25 mL) and purified by ion-exchange HPLC (Dionex BioLC DNAPac PA-100, 22×250 mm, eluent A=water, eluent B=1 M aq. NH$_4$HCO$_3$, constant A for 2 min, then gradient from 0 to 55% B in 28 min, flow rate=10 mL/min, R$_t$=25 min), to give compound 6m as a red foam after lyophilization. A solution of oxime 6m in water (10 mL) was treated in aqueous NaOAc buffer (1M, pH 4.0, 2 mL, 2 mmol) with an aqueous hydroxylamine solution (50 wt-%, 100 µL, ca. 1.6 mmol). After 3 h at RT in the dark, the reaction was diluted with water (10 mL) and filtered (0.2 µm). Purification by ion-exchange HPLC (Dionex BioLC DNAPac PA-100, 22×250 mm, eluent A=water, eluent B=1 M aq. NH$_4$HCO$_3$, gradient from 0 to 60% B in 20 min, flow rate=10 mL/min, R$_t$=18 min) gave compound 6n as a red foam after lyophilization. The yield was determined by UV (290 nm, ext. coeff.=21000 Lmol$^{-1}$ cm$^{-1}$) to be 7.4 µmol (ca. 60% overall with respect to dye).

Example 7

Figure 9:
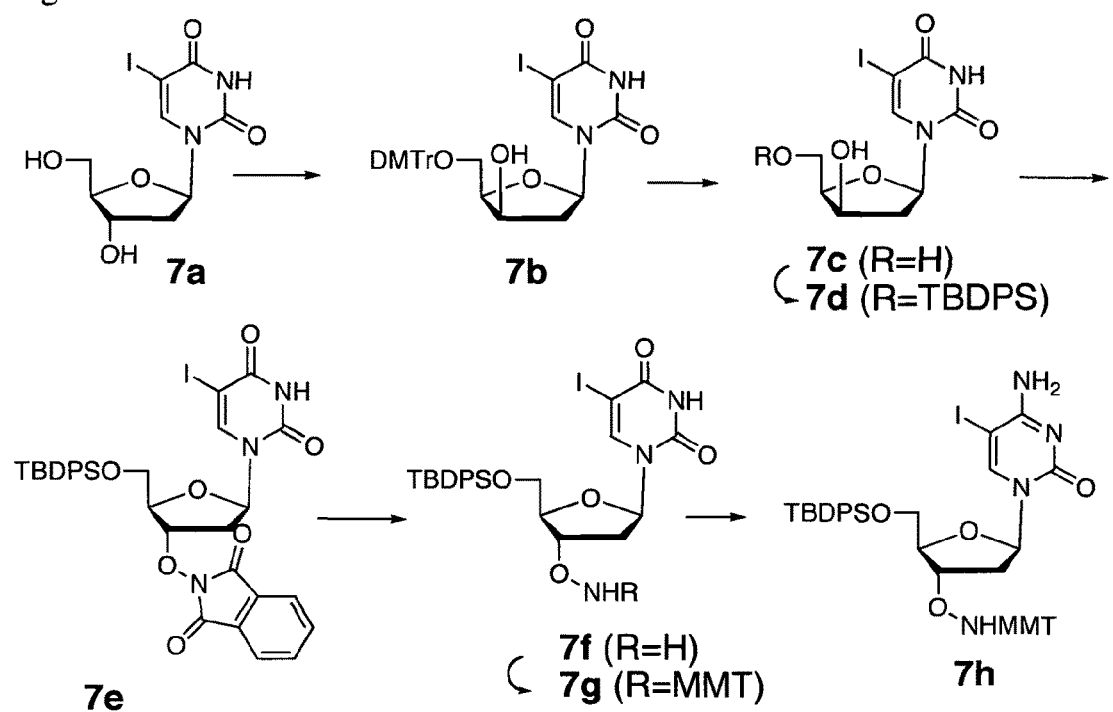
Figure 10:
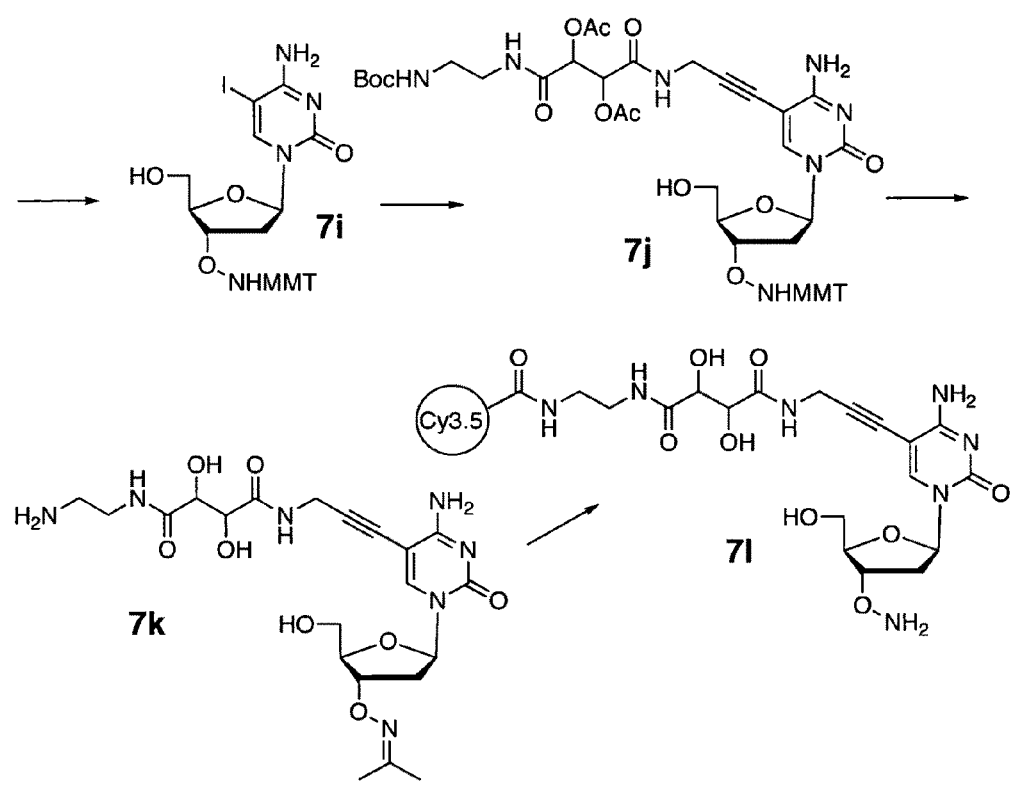

Cytidine Analog with acetylene linker and Cy3.5 fluor (FIGS. 9 and 10)

1-(2'-Deoxy-5'-O-dimethoxytrityl-β-threopentofuranosyl)-5-iodouracil (7b)

To a stirred solution of 5-iodo 2'-deoxyuridine (7a, 10 g, 28.2 mmol) in pyridine (150 mL) were added Et$_3$N (4.4 mL, 31.6 mmol) and DMAP (350 mg, 2.86 mmol), followed by addition of DMTCl (10.5 g, 30.9 mmol) at RT. The reaction mixture was stirred overnight at RT. Et$_3$N (4.8 mL, 34.5 mmol) and MsCl (2.54 mL, 32.8 mmol) were then added to this mixture. After being stirred at RT for 2 h, the mixture was filtered, and the solid was washed with EtOAc. The filtrate was concentrated, dissolved in EtOH (150 mL) and NaOH (1 M, 70 mL) was added. After being refluxed for 1.5 h, the mixture was cooled to RT and treated with HCl (1 M, 40 mL). The EtOH was removed by rotary evaporation and the residue was extracted with CH$_2$Cl$_2$. The organic layer was washed with brine, dried (Na$_2$SO$_4$), filtered and concentrated. The residue was purified by silica gel column chromatography (hexane:EtOAc=2:1 to 1:2) to give 7b (9.5 g, 14.5 mmol, 51%).

$^1$H NMR (CDCl$_3$): δ 9.52 (s, 1H), 8.21 (s, 1H), 7.21-7.44 (m, 9H), 6.82 (m, 4H), 6.15 (dd, 1H), 4.42 (m,1H), 4.06 (m, 1H), 3.80 (s, 6H), 3.62 (m,2H), 3.42 (m,2H), 3.12 (m,1H), 2.72 (m, 1H), 2.19 (m, 1H).

1-(5'-O-tert-Butyldiphenylsilyl-2'-deoxy-β-threopentofuranosyl)-5-iodouracil (7d)

To a stirred solution of solution of 7b (6.7 g, 10.2 mmol) in CH$_2$Cl$_2$ (60 mL) was added trichloroacetic acid (3.34 g, 20.4 mmol) at RT. The reaction mixture was stirred at RT for 2 hours and then poured into hexane (200 mL). The precipitate was removed by filtration, washed with diethyl ether, and dried to give 7c. This solid was dissolved in DMF (45 mL) and the solution was treated with imidazole (2.08 g, 30.6 mmol) and TBDPSCl (2.88 mL, 11.2 mmol) at 0° C. The mixture was warmed to RT, stirred for 3 h, poured into water (200 mL) and extracted with ethyl ether. The organic layer was dried (Na$_2$SO$_4$), filtered and concentrated. The residue was fractionated by silica gel column chromatography (hexane:EtOAc=2:1 to 1:2) to give 7d (5.02 g, 8.5 mmol, 83%).

Compound 7c: $^1$H NMR (DMSO-d$_6$): δ 11.63 (s, 1H), 8.35 (s, 1H), 5.99 (dd, 1H, J=1.8 and 8.1), 5.31 (d, 1H, J=3.3), 4.72 (t, 1H, J=5.4), 4.19 (m, 1H), 3.79 (m,1H), 3.57-3.74 (m,2H), 2.49 (m,1H), 1.87 (m,1H).

Compound 7d: $^1$H NMR (CDCl$_3$): δ 9.31 (s, 1H), 8.32 (s, 1H), 7.66-7.72 (m, 4H), 7.39-7.50 (m, 6H), 6.16 (dd, 1H, J=1.8 and 8.1), 4.53 (m, 1H), 4.09 (m, 2H), 3.89 (m, 1H), 3.50 (br s, 1H), 2.53 (m, 1H), 2.14 (dd, 1H, J=1.8 and 15.0), 1.09 (s, 9H); $^{13}$C NMR (CDCl$_3$): δ 160.51, 150.60, 146.53, 135.77, 135.75, 132.59, 132.44, 130.45, 128.28, 128.25, 85.43, 85.58, 71.17, 68.00, 62.56, 41.27, 27.14.

5'-O-tert-Butyldiphenylsilyl-3'-O-phthalimido-5-iodo-2'-deoxyuridine (7e)

To a stirred suspension of 7d (1.92 g, 3.24 mmol), PPh$_3$ (1.27 g, 4.84 mmol) and N-hydroxyphthalimide (793 mg, 4.86 mmol) in toluene (35 mL) was added DIAD (0.96 mL, 4.88 mmol) at 0° C. The reaction mixture was warmed to RT, stirred at RT for 1 h, and concentrated by rotary evaporation. The residue was purified by silica gel column chromatography (hexane:EtOAc=2:1 to 1:1) to give compound 7e (1.9 g, 2.58 mmol, 79%).

$^1$H NMR (CDCl$_3$): δ 8.49 (s, 1H), 8.09 (s, 1H), 7.84-8.09 (m, 2H), 7.78-7.82 (m, 2H), 7.60-7.65(m, 4H), 7.34-7.44 (m, 6H), 6.44 (dd, 1H, J=5.1 and 9.0), 4.94 (m, 1H), 4.49 (m, 1H), 3.96 (dd, 1H, J=3.0 and 11.7), 3.83 (dd, 1H, J=3.0 and 11.7), 2.84 (dd, 1H, J=5.4 and 14.4), 2.13 (m, 1H( ) 1.06 (s, 9H).

5'-O-tert-Butyldiphenylsilyl-3'-O—(NHMMTr)-5-iodo-2'-deoxyuridine (7g)

To a stirred suspension of 7e (4.9 g, 6.64 mmol) in EtOH (50 mL) was added hydrazine hydrate (0.41 mL, 13.2 mmol) at RT. The mixture was stirred (30 min), filtered and washed with CH$_2$Cl$_2$. The filtrate was concentrated and the residue was purified by silica gel column chromatography (Hex/EtOAc=1/1) to give compound 7f (3.45 g, 5.68 mmol, 85%). Compound 7f (3.45 g, 5.68 mmol) was dissolved in CH$_2$Cl$_2$ (60 mL) and the solution was treated with N,N-diisopropylethylamine (1.48 mL, 8.5 mmol) and MMTCl (1.93 g, 6.25 mmol). The mixture was stirred for 1 h at RT and concentrated. The residue was resolved by silica gel column chromatography (hexane:EtOAc=2:1) to give compound 7g (4.09 g, 4.65 mmol, 82%).

$^1$H NMR (CDCl$_3$): δ8.64 (s, 1H), 8.04 (s, 1H), 7.25-7.73 (m, 20H), 7.13 (m, 2H), 6.79 (m, 2H), 6.59 (s, 1H), 6.11 (dd, 1H, J=5.1 and 9.3), 4.23 (m, 1H), 3.99 (m, 1H), 3.81 (m, 1H), 3.78 (s, 3H), 3.58 (dd, 1H, J=3.0 and 11.7), 2.48 (m, 1H), 1.87 (m, 1H), 1.04 (s, 9H).

5'-O-tert-Butyldiphenylsilyl-3'-O—(NH-MMTr)-5-iodo-2'-deoxycytidine (7h)

To a suspension of 1,2,4-triazole (4.33 g, 62.7 mmol) in CH$_3$CN (50 mL) was added POCl$_3$ (1.28 mL, 13.98 mmol) at 0° C. This mixture was stirred at 0° C. for 10 min and Et$_3$N (8.74 mL, 62.7 mmol) was added. The reaction mixture was stirred at 0° C. for 30 min and a solution of 7g (4.09 g, 4.65 mmol) in CH$_3$CN (50 mL) was added at 0° C. This mixture was stirred at RT for 2 h, water (15 mL) was added and the reaction mixture was concentrated. The residue was diluted with CH$_2$Cl$_2$ and washed with sat. aq. NaHCO$_3$ solution. The organic layer was dried (Na$_2$SO$_4$), filtered and concentrated. The residue was dissolved in pyridine/NH$_4$OH (1/1, 70 mL), stirred at RT for 3 h and concentrated. The residue was purified by silica gel column chromatography (CH$_2$Cl$_2$: MeOH=100:0 to 15:1) to give compound 7h (3.6 g, 4.1 mmol, 88%).

$^1$H NMR (DMSO-d$_6$): δ 8.17 (s, 1H), 7.86 (brs, 2H), 7.09-7.64 (m, 22H), 6.79 (m, 2H), 6.63 (brs, 1H), 3.96 (dd, 1H, J=5.4 and 9.0), 4.04 (m, 1H), 3.96 (m, 1H), 3.69 (s, 3H), 3.65 (m, 1H), 3.51 (m, 1H), 2.29 (m, 1H), 1.72 (m, 2H), 0.94 (s, 9H).

3'-O—(NH-MMTr)-5-iodo-2'-deoxycytidine (7i)

Compound 7h (1.89 g, 2.15 mmol) was dissolved in THF (30 mL) and 1M TBAF in THF (3 mL) was added. The reaction mixture was stirred at RT for 1 h and concentrated. The residue was purified by silica gel column chromatography (CH$_2$Cl$_2$:MeOH=15:1 to 12:1) to give compound 7i (1.11 g, 1.73 mmol, 80%).

$^1$H NMR (DMSO-d$_6$): δ 8.20 (s, 1H), 8.07 (s, 1H), 7.78 (brs, 1H), 7.19-7.30 (m, 10H), 7.10 (d, 2H, J=9.3), 6.82 (d, 2H, J=9.0), 6.59 (brs, 1H), 5.97 (dd, 1H, J=5.7 and 7.8), 5.01 (t, 1H, J=4.7), 3.97 (m, 1H), 3.91 (m, 1H), 3.71 (s, 3H), 3.46 (m, 1H), 3.37 (m, 1H), 3.21 (m, 1H), 1.74 (m, 1H).

3'-O—(NH-MMTr)-5-acetylene diol linker-2'-deoxycytidine (7j)

To a mixture of 7i (920 mg, 1.44 mmol) and CuI (55 mg, 0.29 mmol) in DMF (15 mL) were added Pd(PPh$_3$)$_4$ (166 mg, 0.14 mmol) and Et$_3$N (0.4 mL, 2.87 mmol). After addition of a solution of the linker from above (1.18 g, 2.85 mmol) in DMF (10 mL), the reaction mixture was stirred overnight at RT and concentrated. The residue was purified by silica gel column chromatography (CH$_2$Cl$_2$/MeOH=15/1 to 10/1). The isolated product was further purified by reverse HPLC (Waters Prep Nova-Pak HR C$_{18}$ column, 60 Å, 19×300 mm, eluent A=50% CH$_3$CN in water, eluent B=100% CH$_3$CN, gradient from 0 to 70% B in 20 min, flow rate 5 mL/min). The peak at 21 min was collected and lyophilized to give a white solid 7j (600 mg, 0.65 mmol, 45%).

$^1$H NMR (DMSO-d$_6$): δ 8.61 (t, 1H, J=5.4), 8.13 (t, 1H, J=5.4), 8.07 (s, 1H), 8.04 (s, 1H), 7.78 (brs, 1H), 7.19-7.30 (m, 10H), 7.09 (d, 2H, J=9.0), 6.82 (d, 2H, J=9.0), 6.72 (m, 2H), 5.98 (dd, 1H, J=6.0 and 8.7), 5.45 (s, 2H), 4.95 (t, 1H, J=4.8), 3.99-4.17 (m, 4H), 3.71 (s, 3H), 2.86-3.47 (m, 6H), 2.24 (m, 1H), 2.07, 2.21 (2s, 6H), 1.71 (m, 1H), 1.35 (s, 9H); ESI-MS: m/e=925

3'-O—(N-acetone-oxime)-5-acetylene diol linker-2'-deoxycytidine-5'-triphosphate (7k)

To a stirred solution of 7j (240 mg, 0.26 mmol) in pyridine (1.3 mL) and 1,4-dioxane (1 mL) was added a solution of 2-chloro-4H-1,3,2-benzodioxaphosphorin-4-one in 1,4-dioxane (100 mg/1 mL, 0.9 mL). After 20 min stirring at RT, a mixture of a 0.2 M tributylammonium pyrophosphate in DMF (4.55 mL) and Bu$_3$N (0.52 mL) was added. After 30 min stirring, a solution of I$_2$ (117 mg) in pyridine (9.1 mL) and water (0.18 mL) was added. After 30 min of further stirring, 5% aq. Na$_2$SO$_3$ solution was added until the color disappeared. The solvents were removed by rotary evaporation and the residue was dissolved in CH$_3$CN/H$_2$O (1/1, 20 mL). Solids were removed by filtration (0.45 µM filter) and purified by ion exchange HPLC (Dionex BioLC DNAPac PA-100, 22×250 mm, eluent A=water, eluent B=1M NH$_4$HCO$_3$, gradient from 0% to 50% B in 30 min, flow rate 10 mL/min). The fraction containing triphosphate was pooled and lyophilized to give the intermediate, which was dissolved in water (10 mL). NH$_4$OH (10 mL) was added and the mixture was stirred for 3 h stirring at RT. The solvent was removed under vacuum, and the residue was dissolved in water (25 mL) and resolved by ion exchange HPLC (Dionex BioLC DNAPac PA-100, 22×250 mm, eluent A=water, eluent B=1M NH$_4$HCO$_3$, gradient from 0% to 50% B in 30 min, flow rate 10 mL/min). The fraction containing triphosphate was pooled and lyophilized to give triphosphate with 3'-ONHMMTr (~40 mg), which was separated into 4 eppendorf tubes. To each eppendorf tube were added MeOH (10 µL) and TFA (200 µL). After vortex, the mixture was stand at RT for 2 min and Et$_2$O (1.5 mL) was added. After vortexing, the mixture was allowed to stand at −20° C. for 30 min. After centrifuge (10,000 rpm, 10 min), the supernatant was decanted. The residue was dissolved in aqueous NH$_4$HCO$_3$ (200 mM, 0.5 mL) and acetone (30 µL) was added. After 1 h, the mixture was lyophilized, dissolved in water (20 mL), fractionated by reverse HPLC (Waters Prep Nova-Pak HR C$_{18}$ column, 60 Å, 19×300 mm, eluent A=25 mM TEAA pH 7, eluent B═CH$_3$CN, gradient from 20% to 40% B in 20 min, flow rate 5 mL/min, R$_t$=12 min), and lyophilized to give 7k (~30 mg).

$^1$H NMR (D$_2$O): δ 8.09 (s, 1H), 6.16 (m, 1H), 4.08-4.82 (m, 8H), 3.48 (m, 2H), 3.03 (m, 2H), 2.48 (m, 1H), 2.14 (m, 1H), 1.82, 1.79 (2s, 6H); $^{31}$P NMR (D$_2$O): δ −9.19 (m), −10.47 (m), −21.75 (m).

3'-O-amino-5-acetylene diol linker with Cy 3.5-2'-deoxycytidine-5'-triphosphate (7l)

Compound 7k (5 mg) was dissolved in aq. K$_2$HPO$_4$ (500 mM, 400 µL). A solution of Cy 3.5 NHS ester (5 mg) in DMSO (400 µL) and acetone (200 µL) was added. The reaction mixture was allowed to stand overnight at RT and water was added. This mixture was purified by ion exchange HPLC (Dionex BioLC DNAPac PA-100, 22×250 mm, eluent A=water, eluent B=1 M NH$_4$HCO$_3$, gradient from 70% to 100% B in 20 min, flow rate 10 mL/min, R$_t$=16-19 min). After lyophilization, the 3'-oxime derivative was dissolved in water (5 mL) and 1M NaOAc (pH=4, 1 mL) was added. To this solution was added NH$_2$OH (60 µL). After 2 h in the dark, water (7 mL) was added and the mixture was purified by ion exchange HPLC (Dionex BioLC DNAPac PA-100, 22×250 mm, eluent A=water, eluent B=1M NH$_4$HCO$_3$, gradient from 70% to 100% B in 10 min, then constant 100% B in 30 min, flow rate 10 mL/min, R$_t$=21-25 min) to give compound 7l (0.7 µmol by uv).

Example 8

Figure 11:
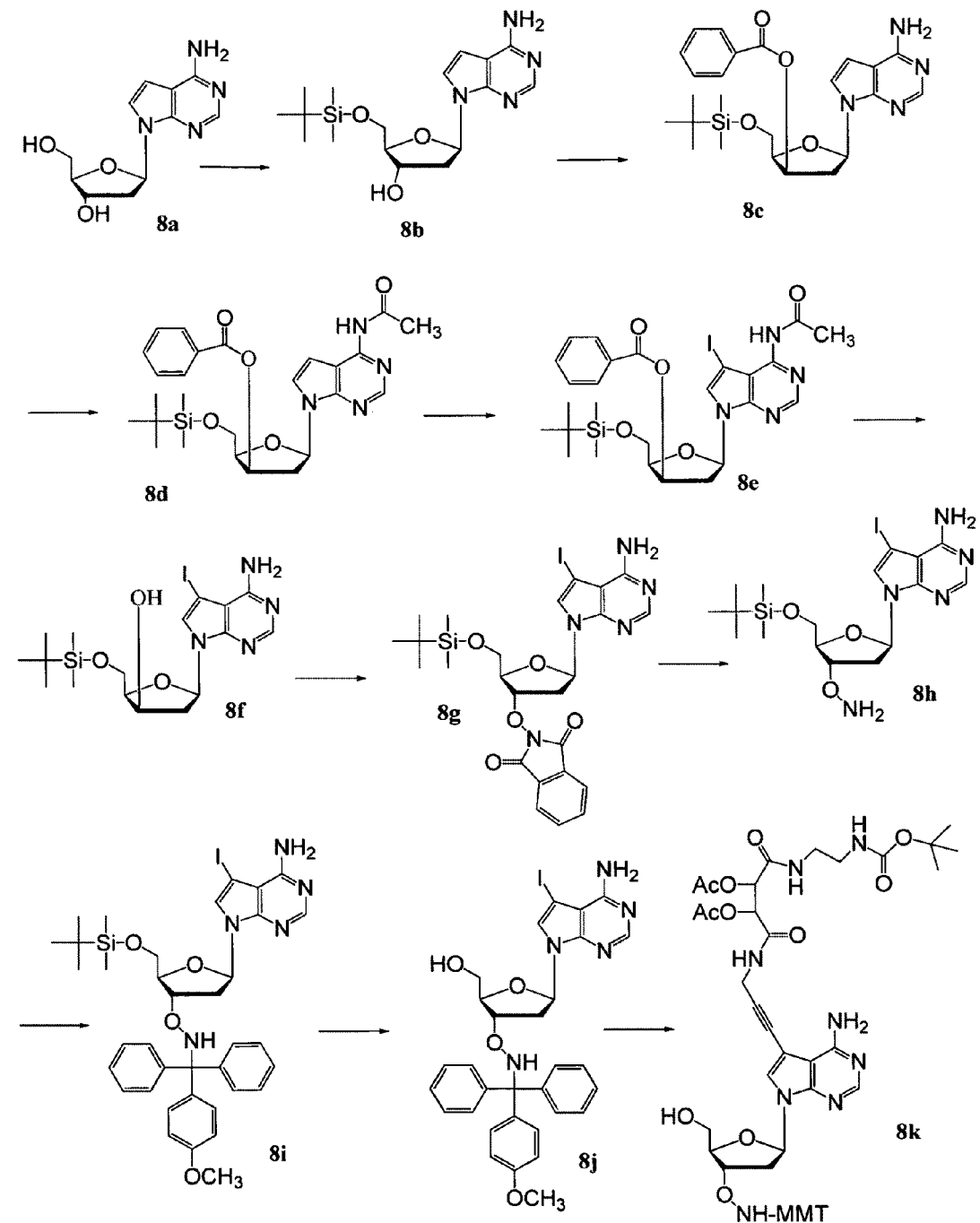
Figure 12:
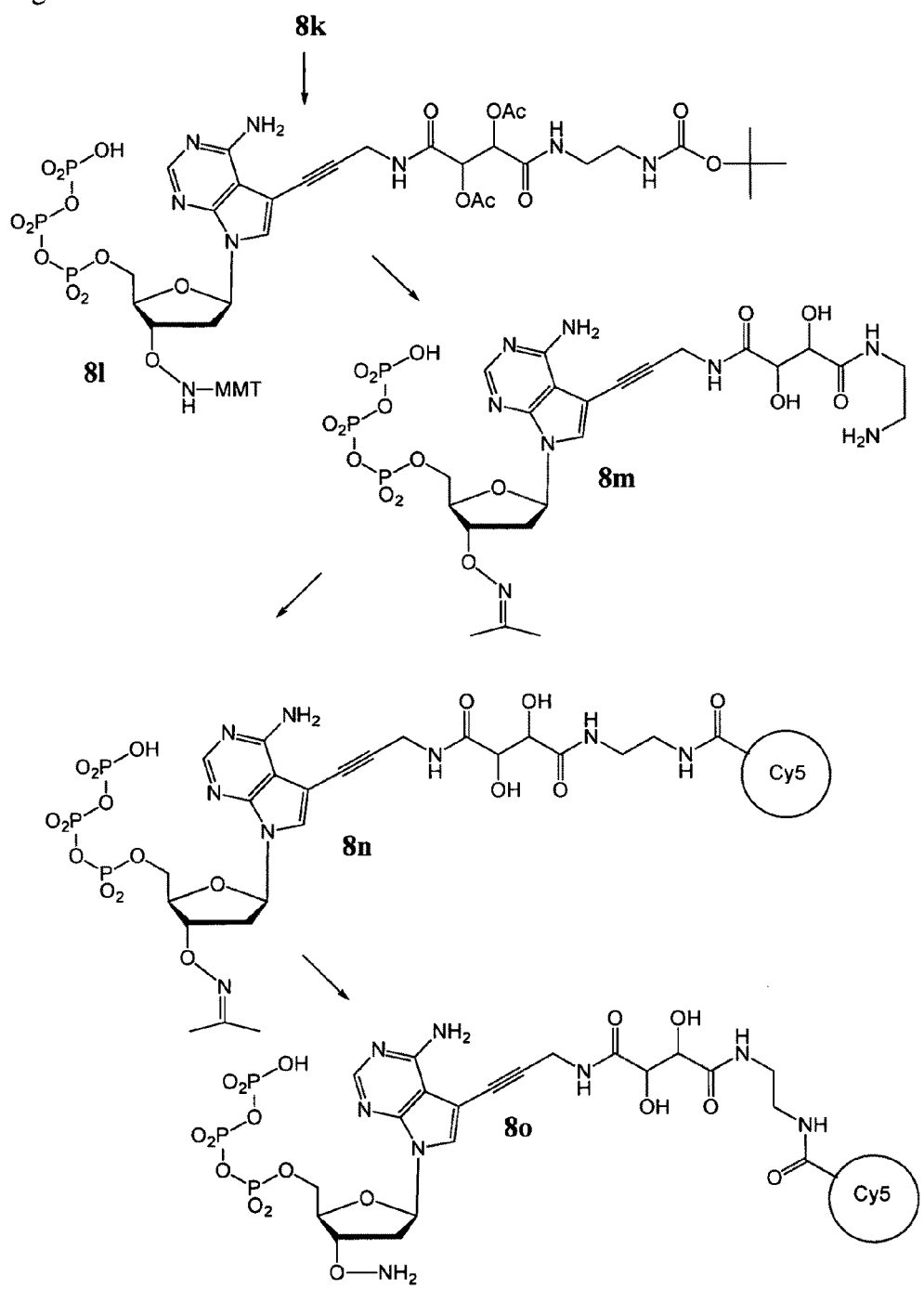

Adenine Analog with acetylene linker and Cy5-fluor (FIGS. 11 and 12)

5'-O-(tert-Butyldimethylsilyl)-deoxydeazaadenosine (8b)

2'-Deoxydeazaadenosine (8a, 1.7 g, 7.11 mmol) was dried by co-evaporation twice with toluene (25 mL, rotary evaporation in a 100 mL round bottom flask). The material was dissolved in anhydrous DMF (25 mL) and the solution was treated with imidazole (1.45 g, 21 mmol) with stirring until all of the imidazole had dissolved. To the solution was added tert-butyldimethylsilyl chloride (1.2 g, 8.5 mmol). The flask was flushed with dry N$_2$ (2 min) and the mixture was stirred overnight at RT. The mixture was diluted with CH$_2$Cl$_2$ (100 mL) and the organic layer was extract with water (3×50 mL) and brine (1×50 mL). The organic layer was dried (Na$_2$SO$_4$), filtered, and concentrated (rotary evaporation). The residue was resolved by flash column chromatography (silica gel, eluant 5% MeOH/95% CH$_2$Cl$_2$ to 9:1 CH$_2$Cl$_2$/MeOH) to give 8b (2.5 g, 7.11 mmol).

N$^6$-Acetyl-5'-O-(tert-butyldimethylsilyl)-xylo-3'-O-(benzoyl)-2',3 dideoxydezaadenosine (8d)

A solution of 5'-O-(tert-butyldimethylsilyl)-deoxydeazaadenosine (8b) (2.5 g, 7.11 mmol), benzoic acid (1.4 g, 11.4 mmol) and triphenylphosphine (3 g, 11.4 mmol) in THF (100 mL) was treated dropwise with diisopropylazodicarboxylate (DIAD, 2.2 mL, 11.4 mmol) at RT. The mixture was stirred for 1 h at RT. The reaction was quenched by the addition of MeOH (10 mL); stirring was continued for 15 min. The solvents were removed in vacuo and the residue was resolved by flash column chromatography (silica gel, eluant 2% to 5% MeOH/CH$_2$Cl$_2$ to give 8c (3.3 g, 7 mmol). This intermediate (8c, 3.3 g, 7 mmol) was dried by co-evaporation twice with anhydrous pyridine (10 mL). The residue was dissolved in a mixture of CH$_2$Cl$_2$ (25 pyridine (1.4 mL) and triethylamine (4.7 mL), and the solution was cooled in an ice bath. Acetyl chloride (8.5 mmol, 0.6 mL) was then added at 0° C., and the mixture was allowed to slowly warm to RT. The mixture was stirred for an additional 16 h at RT. The reaction was quenched by the addition of MeOH (30 mL) followed by stirring for 30 min at RT. The mixture was again cooled on ice to 0° C. and diluted with concentrated aqueous ammonia (10 mL). The mixture was stirred for an additional 15 min at 0° C. The solvents were removed by rotary evaporation and the residue was dissolved in CH$_2$Cl$_2$ (125 mL) and the solution was extracted with saturated aqueous NaHCO$_3$. The organic phase was dried (Na$_2$SO$_4$), filtered, rotary evaporated, and then dried under high vacuum to give 8d (1.5 g, 2.62 mmol).

Synthesis 7'-iodo-5'-O-(tert-Dimethylsilyl)-xylo-2',3'-dideoxydeazaadenosine (8f)

8d (1.34 g, 2.62 mmol) was dissolved in CH$_2$Cl$_2$ (100 mL). To this was added potassium carbonate (Na$_2$CO$_3$) (1.4 g, 10.48 mmol) and ICl (0.853 g, 5.25 mmol). The mixture was stirred for 21 h at RT. The organic solution was washed with aqueous Na$_2$S$_2$O$_3$ (0.1 M, 50 mL) and saturated aqueous NaHCO$_3$ (50 mL), dried over Na$_2$SO$_4$ and evaporated. The residue was resolved by silica gel chromatography (eluant hexane:EtOAc 2:1) to give 8e (1.2 g, 1.8 mmol). This intermediate was re-dissolved in MeOH (100 mL) and treated with NaOMe in MeOH (30%, 0.2 mL, 2.7 mmol). After 2 h at RT, the reaction was quenched by the addition of AcOH (glacial, 0.100 mL). The solvents were removed in vacuo and the residue was partitioned between CH$_2$Cl$_2$ (100 mL) and aqueous NaCl (50% sat., 50 mL). The organic phase was separated and the solvent removed in vacuo. Purification by FLC (silica, gradient 5 to 10% MeOH in CH$_2$Cl$_2$) gave 8f (0.847 g; 1.9 mmol) as a colorless foam.

$^1$H-NMR (Me$_2$SO-d$_6$): 8.1 (1H, s), 7.7 (1H, s), 6.6 (2H, br 6.4 (1H, m), 5.6 (1H, m), 4.3 (1H, m), 3.7-3.9 (3H, m), 2.6-2.7 (1H, m), 2.1-2.2 (1H, m), 0.82 (9H, s), −0.02 (6H, s).

3'-O-Phthalimido-7'-iodo-5'-O-(tert-Dimethylsilyl)-2',3'dideoxydeazaadenosine (8g)

A solution of 8f (0.847 g, 1.9 mmol), N-hydroxy-phthalimide (0.489 g, 3 mmol) and triphenylphosphine (0.786 g, 3 mmol) in THF (50 mL) was treated with DIAD (0.6 mL, 3 mmol) at RT. The mixture was stirred for 1 h at RT, after which the reaction was quenched by the addition of MeOH (10 mL). The solvents were removed in vacuo. Resolution of the residue by FLC (silica, gradient 3 to 10% MeOH in CH$_2$Cl$_2$) gave 8g (1.2 g, 1.9 mmol) as a colorless foam.

3'-O-Amino-7'-iodo-5'-O-(tert-butyldimethylsilyl)-2',3'-dideoxydeazaadenosine (8h)

Cold methylhydrazine (0.19 mL, 3.8 mmol) was added to a stirred solution of 8g (1.2 g, 1.9 mmol) in anhydrous CH$_2$Cl$_2$ at −5° C. to −10° C. After 10 minutes, white 1,2-dihydro-4-hydroxy-2-methyl-1-oxophthalizine precipitated. The suspension was stirred at RT (1 h). The solids were removed by filtration and the precipitate was washed with CH$_2$Cl$_2$ (2×20 mL). The combined filtrates were concentrated and the residue resolved by column chromatography (silica gel, elution gradient 0 to 3% MeOH in CH$_2$Cl$_2$) to give 8h (0.959 g, 1.9 mmol).

3'-O-Aminomonomethoxytrityl-7-iodo-5'-O-(tert-butyldimethylsilyl)-2',3'-dideoxydeazaadenosine (8i)

A sample of 8h was dried by rotary evaporation twice with pyridine (10 mL). The residue was dissolved in anhydrous CH$_2$Cl$_2$ (25 mL). Diisopropyl ethylamine (0.66 mL, 3.8 mmol) and monomethoxytrityl chloride (0.645 g, 2.1 mmol) were added and the progress of the tritylation reaction was monitored by TLC (silica, hexane:EtOAc 1:1). When the reaction was complete, the mixture was diluted with CH$_2$Cl$_2$ (100 mL). The organic layer was washed with saturated NaHCO$_3$ (50 mL) and water (50 mL) and dried (Na$_2$SO$_4$). The solids were removed by filtration and the solvents were removed by rotary evaporation (vacuum pump). The residue was resolved by flash chromatography (silica gel, 230-400 mesh, gradient 2:1 hexane/EtOAc to 1:1 hexane/EtOAc) to give 8i (0.8 g, 1.1 mmol).

3'-O-Aminomonomethoxytrityl-7-iodo-2',3'-dideoxydeazaadenosine (8j)

8i (0.8 g, 1.1 mmol) was dissolved in THF (2 mL) and the solution was treated with a solution of TBAF in THF (1 M, 2 mL). The mixture was stirred for 30 min, at which time the reaction was complete (TLC). The mixture was concentrated by rotary evaporation, diluted with CH$_2$Cl$_2$ (100 mL), and extracted with water (50 mL) and brine (50 mL). The aqueous phases were back extracted with CH$_2$Cl$_2$ (100 mL). The combined organic solutions were dried (Na$_2$SO$_4$) and concentrated by rotary evaporation. The residue was resolved by column chromatography (silica gel, eluted with a gradient 0 to 5% MeOH in CH$_2$Cl$_2$) to give 8j (0.6 g, 1 mmol). $^1$H-NMR (Me$_2$SO-d$_6$): 8.1 (1H,s), 8.05(1H,s), 7.6(1H,s), 7.2-7.4 (10H, m), 6.8(4H, m), 6.6 (2H, br s), 6.3 (1H, m), 5.0 (1H, m), 4.0-4.1 (1H, m), 3.9 (1H, m), 3.8 (3H, s), 3.3-3.5 (2H, m), 2.2-2.3 (2H, m).

3'-O-Aminomonomethoxytrityl-7-iodo-2',3'-dideoxydeazaadenosine with linker (8k)

Intermediate 8j (0.663 g, 1 mmol) was dissolved in DMF (25 mL). CuI (38 mg, 0.2 mmol) was added and the solution was degassed with Ar. Triethylamine (0.3 mL, 2 mmol), Boc linker (5d, 0.828 g, 2 mmol) and Pd(PPh$_3$)$_4$ (115.6 mg, 0.1 mmol) were added successively. The yellow solution was stirred for 1.0 h at RT. After complete conversion of the starting material (TLC, CH$_2$Cl$_2$:MeOH 9:1). The reaction was quenched with 25 ml of 5% EDTA and extracted with EtOAc. The organic layer was dried (Na$_2$SO$_4$) and concentrated to dryness by co evaporating with toluene. The crude mixture was purified by column chromatography on silica (CH$_2$Cl$_2$:MeOH 100:8) to yield 8k (0.8 g, 0.9 mmol).
$^1$H-NMR (Me$_2$SO-d$_6$): 8.8 (1H, br s), 8.7 (1H, br s), 8.1 (1H, br s), 8.05 (1H, s), 7.7 (1H,s), 7.1-7.3 (10H, m), 6.8-6.9 (4H, m), 6.7 (1H, br s), 6.3 (1H, m), 5.4-5.5 (2H, m), 5.1 (1H, m), 4.0-4.1 (1H, m), 3.9 (1H, m), 3.8 (3H, s), 3.3-3.4 (1H, m), 2.8-3.2 (4H, m), 2.2-2.3 (2H, m), 2.1 (3H, s), 1.9 (3H, s), 1.4 (9H, s).

3'-O—(N-acetone-oxime)-2'-deoxy-7-deazaadenosine-5'-triphosphate Carrying acetylene linker with diol and primary amine (8m)

To a solution of the fully protected 5'-OH nucleoside 8k (3'-O—NH-MMTr, linker-di-OAc/NH-Boc) (480 mg, 0.5 mmol) in pyridine (2 mL) and dioxane (1.7 mL) was added a solution of 2-chloro-4H-1,3,2-benzodioxaphosphorin-4-one (130 mg, 0.7 mmol) in dioxane (1.3 mL) at RT. After 20 min, a mixture of tributylammonium pyrophosphate in DMF (0.2 M, 7 mL, 1.4 mmol) and tributylamine (0.8 mL, 3.2 mmol) was added. After a further 20 min, a solution of iodine (180 mg, 0.7 mmol) and water (0.28 mL) in pyridine (14 mL) was added. After 30 min, the reaction was quenched by the addition of aqueous Na$_2$SO$_3$ (5%, 0.5 mL). The solvents were removed in vacuo. Water (25 mL) and CH$_3$CN (20 mL) was added, and the mixture was filtered (0.2 µm). Rough purification by reverse phase HPLC (Waters Prep Nova-Pak HR C$_{18}$ column, 60 Å, 19×300 mm, eluent A=water, eluent B=CH$_3$CN, gradient from 18 to 50% B in 25 min, then to 60% B in 5 min, then to 90% B in 2 min, then constant 90% B for 8 min, flow rate=5 mL/min, R$_t$=25-33 min) gave protected triphosphate 8l (mixture of compounds due to partial loss of diol-acetates) as a colorless foam after lyophilization. This intermediate was treated with ammonium hydroxide (conc., 50 mL) for 4 h at RT and then lyophilized again. The residue was treated with MeOH (1.2 mL) and TFA (32 mL) at RT for 3 min, resulting in a clear solution. Diethyl ether (250 mL) was added and the suspension was stored at −20° C. for 1 h. The precipitate was separated by centrifugation and the supernatant was decanted. The precipitate was redissolved carefully in aqueous sodium bicarbonate buffer (80 mM, 130 mL) containing acetone (2 mL). The pH was adjusted to 6 by addition of dilute aqueous HCl, and the solution was let stand at RT for 3 h. The remaining acetone and diethyl ether were removed in vacuo. The aqueous solution was filtered (0.2 µm). Purification by ion-exchange HPLC (Dionex BioLC DNAPac PA-100, 22×250 mm, eluent A=water, eluent B=1 M TEAB pH 8, constant A for 2 min, then gradient from 0 to 50% B in 16 min, flow rate=10 mL/min, R$_t$=16 min), followed by reverse phase HPLC (Waters Prep Nova-Pak HR C$_{18}$ column, 60 Å, 19×300 mm, eluent A=25 mM TEAA pH 7, eluent B=50% CH$_3$CN in A, gradient from 20 to 60% B in 25 min, flow rate=5 mL/min, R$_t$=18 min) gave 8m as a colorless foam after lyophilization. The yield was estimated by UV (280 nm, ext. coeff. 13000 Lmol$^{-1}$ cm$^{-1}$) to be ca. 130 µmol (ca. 25% overall).

$^1$H-NMR (D$_2$O, 300 MHz): ∂ (ppm, rel to HDO=4.65)= 1.79 (s, 3H); 1.84 (s, 3H); 2.45-2.52 (m, 2H); 3.00-3.08 (m, 2H); 3.42-3.48 (m, 2H); 3.95-4.10 (m, 3H); 4.18-4.28 (m, 2H); 4.48 (s, 2H); 4.83-4.88 (m, 1H); 6.33 (dd, J=7.4, 7.6 Hz, 1H); 7.48 (s, 1H); 7.86 (s, 1H). $^{31}$P-NMR (D$_2$O, 120 MHz): ∂ (ppm, rel to external H$_3$PO$_4$=0)=−9.0 (d, J=19.5 Hz, 1P); −11.2 (d, J=19.5 Hz, 1P); −22.5 (t, J=19.5 Hz, 1P).

7-deaza-dATP-ONH$_2$ Carrying a Cy5-Labelled acetylene diol linker

A solution of 8m (estimated 10 µmol) in aqueous K$_2$HPO$_4$ (0.5 M, 0.5 mL) was mixed with a solution of Cy5-OSu (8 mg, ca. 8 µmol) in DMSO (0.7 mL) and acetone (0.35 mL). The mixture was incubated at RT in the dark for 4 h. The reaction mixture was diluted with water (16 mL) and purified by ion-exchange HPLC (Dionex BioLC DNAPac PA-100, 22×250 mm, eluent A=water, eluent B=1 M aq. NH$_4$HCO$_3$, constant A for 2 min, then gradient from 0 to 60% B in 18 min, flow rate=10 mL/min, R$_t$=19 min), to give 8n as a blue foam after lyophilization. To a solution of this oxime in water (10 mL) was added aqueous sodium acetate buffer (1 M, pH 4.0, 2 mL, 2 mmol) and aqueous hydroxylamine solution (50 wt-%, 100 µL, ca. 1.6 mmol). After 3 h at RT in the dark, the reaction was diluted with water (10 mL) and filtered (0.2 µm). Purification by ion-exchange HPLC (Dionex BioLC DNAPac PA-100, 22×250 mm, eluent A=water, eluent B=1 M aq. NH$_4$HCO$_3$, constant A for 2 min, then gradient from 0 to 80% B in 18 min, flow rate=10 mL/min, R$_t$=17 min) gave 8o as a blue foam after lyophilization. The yield was determined by UV (290 nm, ext. coeff.=19000 Lmol$^{-1}$ cm$^{-1}$) to be 4.6 µmol (ca. 60% with respect to dye).

Example 9

Figure 13:
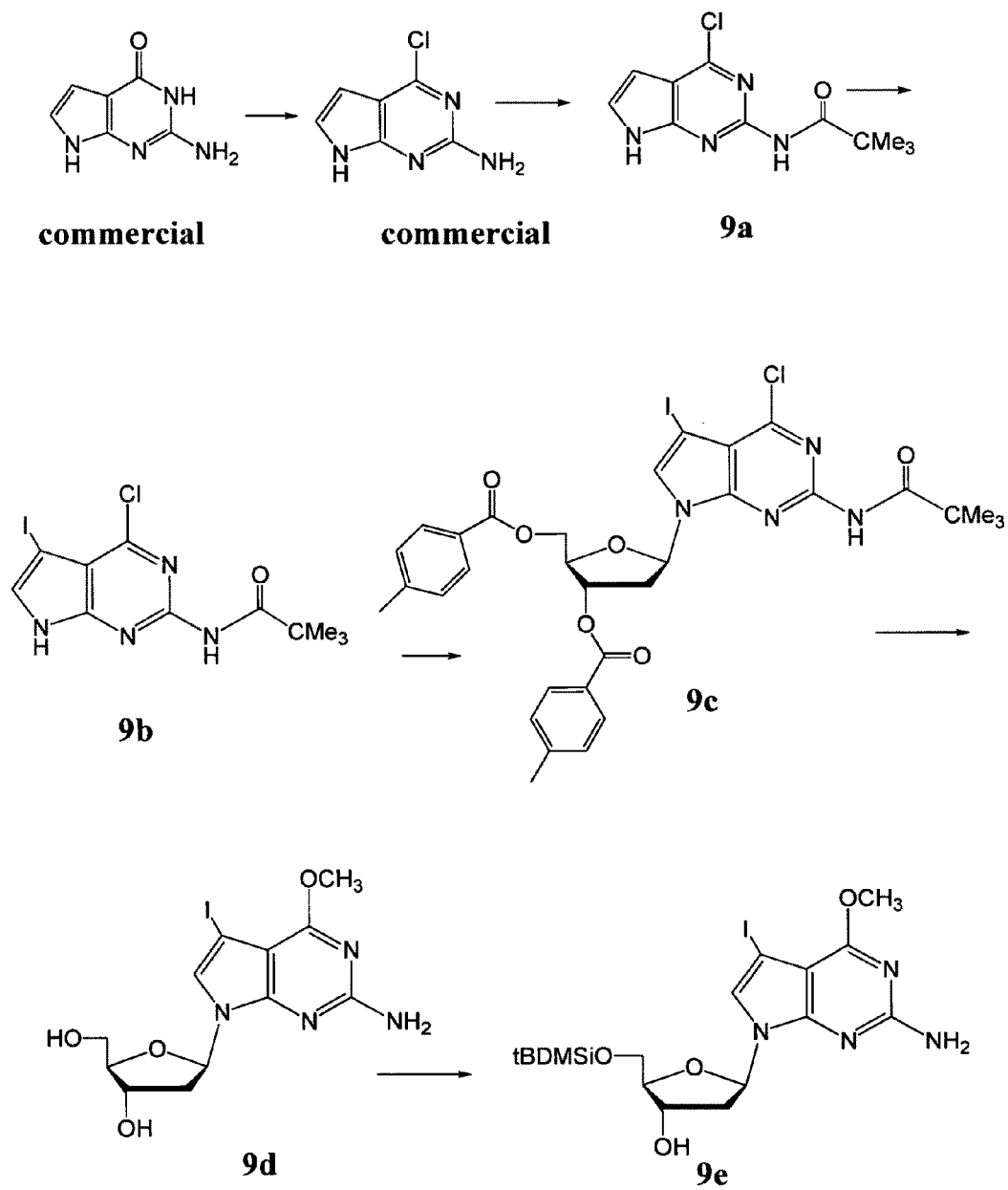
Figure 14:
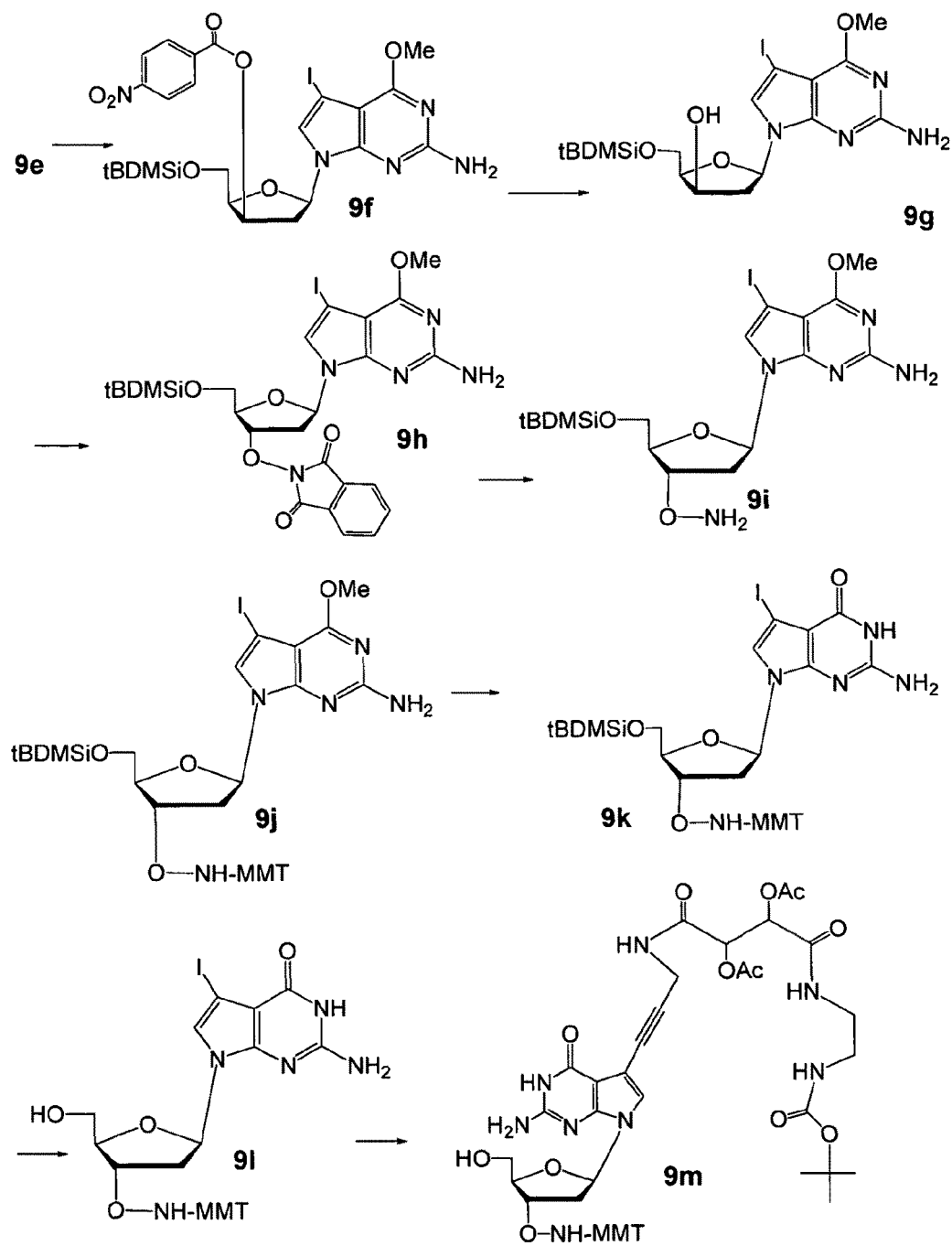
Figure 15:
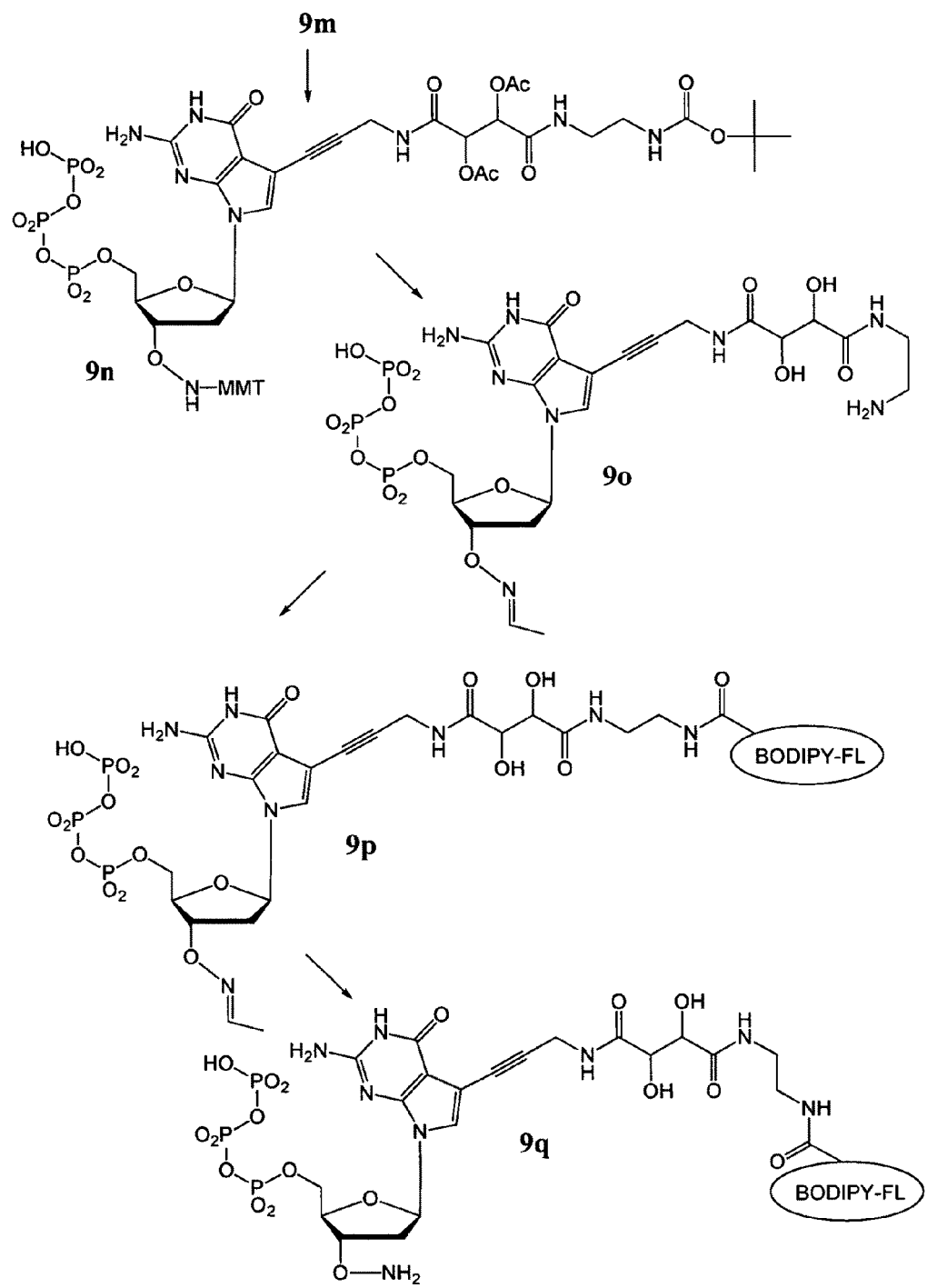

Synthesis of Guanine Analog with an Attached fluor (FIGS. 13 and 14)

4-Chloro-2-trimethylacetamido-pyrrolo[2.3-d]pyrimidine (9a)

To a stirring solution of 2-amino-4-chloro-pyrrolo[2,3-d]pyrimidine (7.3 g, 43.61 mmol) in anhydrous pyridine (120 mL) was added pivaloyl chloride (18.7 mL, 152.63 mmol). The reaction was stirred at RT under nitrogen for 16 h and quenched with MeOH (50 mL). The solvents were then removed in vacuo, and the residue was co-evaporated with toluene (100 mL). The resulting residue was dissolved in EtOAc (150 mL) and washed with 0.1 M HCl (3×75 mL). The organic layer was dried ($MgSO_4$) and evaporated. The crude material was resolved by silica chromatography (30% EtOAc/hexane) to yield 9a (12.2 g) as a white crystalline solid.

$^1$H-NMR (DMSO-$d_6$): 1.2 (9H, s), 6.5 (1H, d, $J_1$=4 Hz), 7.5 (1H, d, $J_1$=4 Hz), 10.1 (1H, s), 12.3 (1H, s).

4-Chloro-5-iodo-2-trimethylacetamido-pyrrolo[2,3-d]pyrimidine (9b)

4-Chloro-2-trimethylacetamido-pyrrolo[2,3-d]pyrimidine (9a, 10.9 g, 43.24 mmol) was dissolved in anhydrous THF (120 mL) under nitrogen. After the addition of N-iodosuccinimide (10.7 g, 47.56 mmol), the mixture was stirred at RT for 1 h. The solvent was then removed in vacuo. The residue dissolved in EtOAc (100 mL) and washed with 1 M sodium thiosulfate (3×100 mL). Column chromatography purification (2% MeOH in DCM, isocratic) yielded 9b (12.9 g).

$^1$H-NMR (DMSO-$d_6$): 1.2 (9H, s), 7.8 (1H, d, $J_1$=4 Hz), 10.1 (1H, s), 12.7 (1H, s).

Synthesis of 4-chloro-7-(2-deoxy-3,5-di-O-(p-toluoyl)-beta-D-erythro-pentofuranosyl)-$N^2$-[trimethylacetamido]-7-iodo-pyrrolo[2,3-d]pyrimidine (9c)

To a suspension of powdered KOH (1 g, 85%, 18.44 mmol) and TDA-1 (0.2 mL, 0.63 mmol) in $CH_3CN$ (60 mL), was added compound 9b (2 g, 5.3 mmol). After stirring the mixture for 5 min, 2-deoxy-3,5-di-O-(p-toluoyl)-a-D-erythro-pentofuranosyl chloride (2.7 g, 6.9 mmol) was added and the stirring was continued for 1 h. Insoluble material was removed by filtration, the precipitate was washed with $CH_3CN$ and then hot acetone, and the combined filtrates were evaporated to dryness. The residue was resolved by FC (silica gel, eluent $CH_2Cl_2$). The combined fractions containing product were evaporated to give 9c as a foam (1.6 g); TLC (silica gel, A): Rf=0.53.

$^1$H NMR ($CDCl_3$): d=1.35-1.37 (m, 9 H, 3 $CH_3$), 2.42 (s, 3 H,$CH_3$), 2.45 (s, 3 H, $CH_3$), 2.78-2.82 (m, 1 H, H-2'), 2.91-2.97 (m, 1H, H-2'), 4.55-4.58, 4.63-4.66, 4.73-4.76 (3 m, 3 H, H-4', 2H-5'), 5.77-4.78 (m, 1 H, H-3'), 6.74 (t, 1 H, J=6.8 Hz, H-1'), 7.25, 7.28, 7.90, 7.98 (4 d, 8 H, J=8.1 Hz,), 8.16 (s, 1 H, H-6), 10.29 (s, 1 H, NH).

2-Amino-6-methoxy-7-iodo-9-[beta-D-ribo-5'-O-(tert-butyldimethylsilyl)-2'-deoxyribofuranosyl]-7-deazapurine (9e)

A solution of 9c (3.8 g, 5.2 mmol) in 0.5M MeONa/MeOH (71 mL) was heated under reflux for 3 h. The reaction mixture was neutralized with glacial acetic acid (2.0 mL), the crude product was adsorbed to silica gel, and applied on the top of a silica column eluting with 95:5 $CH_2Cl_2$:MeOH. Compound containing fractions were collected and evaporated to dryness to give 9d (1.8 g) as a colorless solid. To a stirred solution of 9d (1.5 g; 3.69 mmol) and imidazole (652 mg; 9.5 mmol) in anhydrous DMF (15 mL) was added tert-butyldimethylsilyl chloride (0.720 g; 4.8 mmol). The reaction mixture was stirred at room temperature for 20 h. Most of the solvent was removed in vacuo, and the residue was purified by flash column chromatography (silica gel, eluant EtAOc:hexane 1:2-0.5) to give 9e (1.5 g) as a white foam.

$^1$H NMR ($CDCl_3$): 7.23 (s, 1H), 6.49 (dd, J=6.1, 7.7 Hz, 1H), 4.46 (m, 1H), 3.99 (s, 3H), 3.94 (m, 1H), 3.79-3.87 (m, 2H), 2.36-2.44 (ddd, J=5.8, 7.7, 13.3 Hz, 1H), 2.24-2.31 (ddd, J=3.1, 6.0, 13.3 Hz, 1H), 0.96 (s, 9H), 0.14 (s, 3H),0.13 (s, 3H)

2-Amino-6-methoxy-7-iodo-9-[beta-D-xylo-5'-O-(tert-butyldimethylsilyl)-2'-deoxyribofuranosyl]-7-deazapurine (9g)

A solution of 9e (1.5 g, 2.88 mmol), p-nitrobenzoic acid (770 mg, 4.61 mmol) and $Ph_3P$ (1.2 g, 4.61 mmol) in THF (20 mL) was added DIAD (0.9 mL, 4.61 mmol) at RT. After incubation for 1 h, MeOH (2 mL) was added. The solvents were removed in vacuo and the residue was resolved by FLC (silica, gradient EtOAc-hexane 1:2 to 1:1) to give 9f (1.7 g) as a yellowish white solid. A solution of 9f (1.7 g) in methanolic ammonia (40 mL) was stirred for 1 h at RT and then concentrated under vacuum. The residue was resolved by chromatography (silica gel, eluent EtOAc:hexane 1:2-2:1) to give 9g (1.4 g) as white foam.

$^1$H NMR (DMSO-$d_6$): 7.4 (s, 1H), 6.3-6.4 (s, 2H), 6.25-6.3 (dd, J=2.7, 8.4 Hz, 1H), 5.4 (d, J,3.9, 1H), 4.3 (m, 1H), 3.99 (s, 3H), 3.94 (m, 1H), 3.7-3.8 (m, 2H), 2.6-2.7 (m, 2H), 1.2 (s, 9H), 0.9 (s, 6H)

Synthesis of 2-amino-7-iodo-9-[beta-D-ribo-3'-O-aminoxy-N-(4-monomethoxytritylamino)-2-deoxyribofuranosyl]-7-deazapurine (9k)

To a solution of 9g (1.4 g, 2.7 mmol), N-hydroxyphthalimide (704 mg, 4.32 mmol) and triphenylphosphine (1.1 g, 4.32 mmol) in THF (20 mL) was added DIAD (0.85 mL, 4.32 mmol) at room temperature. After 1 h the reaction was quenched by the addition of methanol (2 mL). The solvents were removed in vacuo. Purification by FLC silica, gradient ethyl acetate-hexane (1:2-1:1) gave 9h (1.8 g) as a colorless foam.

Cold methylhydrazine (0.3 mL, 5.4 mmol) was added to a stirred solution of 9h (1.8 g, 2.7 mmol) in anhydrous $CH_2Cl_2$ at −5° C. to −10° C. After 10 minutes, 1,2-dihydro-4-hydroxy-2-methyl-1-oxophthalizine appeared as a white precipitate. The suspension was stirred at RT for 1 h, the solids were removed by filtration, and the precipitate washed with $CH_2Cl_2$ (2×20 mL). The combined filtrates were concentrated and the residue was resolved by silica gel column chromatography (eluent with 10% MeOH in EtOAc) to give 9i (600 mg).

By rotary evaporation twice with pyridine (5 mL each), 9i (600 mg, 1.12 mmol) was dried and then dissolved in anhydrous $CH_2Cl_2$ (10 mL). Diisopropyl ethylamine (0.29 mL, 1.6 mmol) and monomethoxytrityl chloride (364 mg, 1.17 mmol) were added. The reaction was complete in 4 h (by TLC). The reaction was diluted with $CH_2Cl_2$ (50 mL), and the organic layer was washed saturated aqueous $NaHCO_3$ (25 mL) and water (25 mL) and then dried over $Na_2SO_4$. The solids were removed by filtration and the filtrate rotary evaporated under vacuum, and the residue was resolved by FLC (silica gel (230-400 mesh, eluent hexane/EtOAc 2:1) to give 9j (0.784 g). Intermediate 9j (784 mg, 0.97 mmol) dissolved in anhydrous DMF (10 mL) was treated with sodium thiocresolate (657 mg, 4.5 mmol) and the mixture was heated at 90° C. for 1 h. The solvent was removed under vacuum and the residue was resolved by chromatography (silica gel (5% MeOH in $CH_2Cl_2$) to give 9k as a yellowish white solid (600 mg).

Intermediate 9k (600 mg) in THF (0.5 mL) was treated with 1M TBAF in THF (0.5 mL), and the mixture was stirred for 30 min. TLC showed completion of reaction. The mixture was concentrated, diluted with $CH_2Cl_2$ (25 mL), and extracted with water (15 mL) and brine (15 mL). The aqueous extracts were back extracted with $CH_2Cl_2$ (25 mL), and the combined organic phases were dried ($Na_2SO_4$) and evaporated. The residue was resolved by chromatography (silica, eluent 5% MeOH in $CH_2Cl_2$) to give 9l (500 mg).

$^1$H NMR (DMSO-$d_6$): 10.45 (s, 1H), 8.05 (s, 1H), 7.9 (s, 1H), 6.9-7.4 (m, 14H), 6.3 (s, 2H), 6-6.1(m, 1H), 4.85 (t, J=6.2, 1H), 4.0 (m,1H), 3.84 (m, 1H), 3.72 (s, 3H), 3.3-3.4(m, 2H), 2.1-2.2 (m, 2H).

Synthesis of the Guanine Derivative with a Side Chain (9m)

Intermediate 9k (500 mg, 0.73 mmol) dissolved in DMF (10 mL) was treated with CuI (28 mg, 0.147 mmol), the mixture was degassed with Ar, and triethylamine (0.2 mL, 1.47 mmol), Boc linker (0.61 g, 1.47 mmol) and Pd(PPh$_3$)$_4$ (84 mg, 0.073 mmol) were added successively. The yellow solution was stirred for 3.0 h at RT in the dark. Complete conversion of the starting material was detected by TLC ($CH_2Cl_2$:MeOH, 9:1). The reaction was quenched by adding 5% EDTA (5% aqueous). and the mixture was extracted with EtOAc. The organic layer was dried ($Na_2SO_4$) and concentrated to dryness by co-evaporating with toluene. The crude mixture was resolved by column chromatography on silica ($CH_2Cl_2$:MeOH, 10:1). To give 9m (0.481 g).

$^1$H NMR (DMSO-$d_6$): 10.43 (s, 1H), 8.7 (m, 1H), 8.2 (m,1H), 8.1 (s, 1H), 6.85-7.35(m, 14H), 6.8(br,s,1H), 6.3(br, s, 1H), 6-6.1(m,1H), 5.4-5.5 (m, 2H), 4.82 (t, J=5.8, 1H), 3.8-4.2 (m, 4H), 3.7 (s, 3H), 3.3-3.4(m, 2H), 2.8-3.2(m, 4H), 2.1-2.3(m,2H), 2.07 (s, 3H), 2.02(s,3H), 1.37 (s, 9H).

3'-O—(N-acetaldehyde-oxime)-2'-deoxy-7-deaza-guanosine-5'-triphosphate Carrying acetylene linker with diol and primary amine (9o)

To a solution of 9m (480 mg, 0.5 mmol) in pyridine (2 mL) and dioxane (1.9 mL) was added a solution of 2-chloro-4H-1,3,2-benzodioxaphosphorin-4-one (110 mg, 0.6 mmol) in dioxane (1.1 mL) at room temperature. After 20 min a mixture of tributylammonium pyrophosphate in DMF (0.2 M, 6 mL, 1.2 mmol) and tributylamine (0.7 mL, 2.8 mmol) was added. After 20 min a solution of iodine (155 mg, 0.6 mmol) and water (0.24 mL) in pyridine (12 mL) was added. After 20 min the reaction was quenched by the addition of aqueous $Na_2SO_3$ (5%, 0.5 mL). The solvents were removed in vacuo. The intermediate was treated with ammonium hydroxide (conc., 40 mL) for 5 h at room temperature. The solvents were removed by lyophilization. The residue was redissolved in TEAA buffer (50 mM, 65 mL) and $CH_3CN$ (30 mL). The mixture was filtered (0.2 µm). Purification by reverse phase HPLC (Waters Prep Nova-Pak HR $C_{18}$ column, 60 Å, 19×300 mm, eluent A=25 mM TEAA pH 7, eluent B=50% $CH_3CN$ in A, gradient from 30 to 60% B in 22 min, flow rate=5 mL/min, $R_f$=16 min) gave the diol intermediate as a colorless foam after lyophilization. This foam was treated with MeOH (0.4 mL) and TFA (6 mL) at room temperature for 3 min. $Et_2O$ (70 mL) was added and the suspension was stored at −20° C. for 1 h. The precipitate was separated by centrifugation and the supernatant was decanted. The precipitate was re-dissolved carefully in aqueous $NaHCO_3$ buffer (80 mM, 90 mL) containing acetaldehyde (1 mL). The solution was let stand at room temperature for 3 h. The remaining acetaldehyde and $Et_2O$ were removed in vacuo. The aqueous solution was filtered (0.2 µm). Purification by ion-exchange HPLC (Dionex BioLC DNAPac PA-100, 22×250 mm, eluent A=water, eluent B=1 M aq. $NH_4HCO_3$, constant A for 2 min, then gradient from 0 to 50% B in 20 min, flow rate=10 mL/min, $R_f$=15 min), followed by reverse phase HPLC (Waters Prep Nova-Pak HR $C_{18}$ column, 60 Å, 19×300 mm, eluent A=25 mM TEAA pH 7, eluent B=50% $CH_3CN$ in A, gradient from 0 to 45% B in 40 min, flow rate=5 mL/min, $R_f$=31 and 31.5 min) gave 9o as a colorless foam after lyophilization. The yield was determined by UV (273 nm, ext. coeff. 10000 $Lmol^{-1} cm^{-1}$) to be 60 µmol (12% overall).

$^1$H-NMR ($D_2O$, 300 MHz): ∂ (ppm, rel to HDO=4.65)= 1.76 (d, J=5.9 Hz, 1.5H); 1.80 (d, J=5.7 Hz, 1.5H); 2.40-2.56 (m, 2H); 3.00-3.08 (m, 2H); 3.42-3.48 (m, 2H); 3.95-4.32 (m, 5H); 4.47 (s, 2H); 4.85-4.95 (m, 1H); 6.24 (dd, J=7.5, 13.8 Hz, 1H); 6.93 (q, J=5.7 Hz, 0.5H); 7.26 (s, 1H); 7.51 (q, J=5.9 Hz, 0.5H). $^{31}$P-NMR ($D_2O$, 120 MHz): ∂ (ppm, rel to external $H_3PO_4$=0)=−0.9 (d, J=19.5 Hz, 1P); −11.2 (d, J=19.5 Hz, 1P); −22.7 (t, J=19.5 Hz, 1P).

7-deaza-dGTP-ONH$_2$ Carrying a BODIPY-FL-C$_5$-Labelled acetylene diol linker (9q)

A solution of 9o (ca. 7 µmol) in aqueous $K_2HPO_4$ (0.5 M, 0.5 mL) was mixed with a solution of BODIPY-FL-C$_5$-OSu (5 mg, ca. 12 µmol) in DMSO (0.7 mL) and acetone (0.3 mL). The mixture was incubated at room temperature in the dark for 4 h. The reaction mixture was diluted with water (15 mL) and purified by ion-exchange HPLC (Dionex BioLC DNA-Pac PA-100, 22×250 mm, eluent A=water, eluent B=1 M aqueous $NH_4HCO_3$, constant A for 2 min, then gradient from 0 to 65% B in 18 min, flow rate=10 mL/min, $R_f$=17 min), to give the intermediate oxime 9p as an orange foam after lyophilization. To a solution of this oxime in water (5 mL) was added aqueous sodium acetate buffer (1M, pH 4.0, 1 mL, 1 mmol) and aqueous hydroxylamine solution (50 wt-%, 50 µL, ca. 0.8 mmol). After 4 h at room temperature in the dark, the reaction was diluted with water (5 mL). Purification by ion-exchange HPLC (Dionex BioLC DNAPac PA-100, 22×250 mm, eluent A=water, eluent B=1 M aq. $NH_4HCO_3$, constant A for 2 min, then gradient from 0 to 100% B in 14 min, flow rate=10 mL/min, $R_f$=14 min) 9q as an orange foam after lyophilization. The yield was determined by UV (273 nm, ext. coeff.=12000 $Lmol^{-1} cm^{-1}$) to be 2.0 µmol (ca. 30% overall with respect to nucleoside).

Example 10

Figure 16:
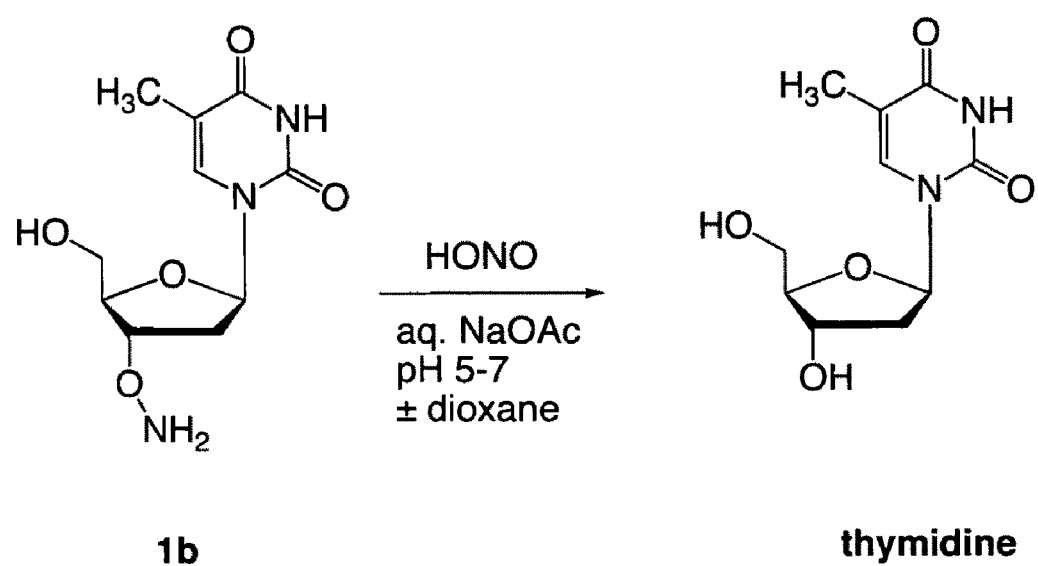

Model Reaction Cleavage of O—NH$_2$ Unit (FIG. 16)

(a) Cleavage of O-(4-nitrobenzyl)hydroxylamine with Aqueous HONO at Varying Dielectric To an aqueous solution of O-(4-nitrobenzyl)hydroxylamine (1 mM, 300 µL) were added "co-solvent" (brine or water or ethanol or isopropanol or acetonitrile or 1,4-dioxane) (500 µL), aqueous sodium acetate buffer (1 M, 100 µL, pH 3.5 to 6.0), and aqueous sodium nitrite solution (100 mM, 100 μL). The resulting pH was measured with a microelectrode (accuracy ca.±0.02). After 1 h at RT, an aliquot (100 μL) was removed, neutralized by the addition of K-phosphate buffer (170 mM, 600 μL, pH 7), and analyzed by analytical reverse-phase HPLC (Waters NovaPak C-18 4 μm, 3.9×150 mm, with guard column Waters NovaPak C-18 4 μm, 3.9×15 mm, eluent A=3% acetonitrile in 25 mM TEAA pH 7, eluent B=acetonitrile, gradient from 20% B to 50% B in 30 min, flow rate=0.5 mL/min, $R_t$=product: 8.5 min; starting material: 9.5 min.).

(b1) Cleavage of 3'-O-aminothymidine 1b with Aqueous HONO and Dioxane as Cosolvent To an aqueous solution of 3'-O-aminothymidine (1b, 20 mM, 50 μL) were added dioxane (300 μL) and aqueous nitrous acid (1 M, 700 μL, pH 5.0 to 6.0, prepared from sodium nitrite and 1 M NaOAc buffer). The resulting pH was measured with a microelectrode (accuracy ca.±0.02). After 5 min at room temperature, and aliquot (100 μL) was removed, neutralized by the addition of K-phosphate buffer (1 M, 600 μL, pH 7), and analyzed by analytical reverse-phase HPLC (Waters NovaPak C-18 4 μm, 3.9×150 mm, with guard column Waters NovaPak C-18 4 μm, 3.9×15 mm, eluent A=25 mM TEAA pH 7, eluent B=acetonitrile, gradient from 3% B to 13% B in 20 min, flow rate=0.5 mL/min, $R_t$=product: 8 min; starting material: 11 min.). The amount of cleavage was determined by integrating (267 nm) the peaks of the remaining 1b and the product (thymidine). The rates are as follows:

| actual pH (±0.02) | product after 5 min |
| --- | --- |
| 6.54 | 17% |
| 6.21 | 48% |
| 6.00 | 85% |
| 5.72 | >99% |

(b) Cleavage of 3'-O-aminothymidine 1b with Aqueous HONO and No Cosolvent

To an aqueous solution of 3'-O-aminothymidine (1b, 20 mM, 2 μL) was added aqueous nitrous acid (350-700 mM NaNO$_2$/1 M NaOAc, 50 μL, pH 5.5-5.75). The resulting pH was measured with a microelectrode (accuracy ca.±0.02). After 1 or 2 min at room temperature, the reaction was quenched by the addition of K-phosphate buffer (1 M, 200 μL, pH 7), and analyzed by analytical reverse-phase HPLC (Waters NovaPak C-18 4 μm, 3.9×150 mm, with guard column Waters NovaPak C-18 4 μm, 3.9×15 mm, eluent A=25 mM TEAA pH 7, eluent B=acetonitrile, gradient from 3% B to 13% B in 20 min, flow rate=0.5 mL/min, $R_t$=product: 8 min; starting material: 11 min.). The amount of cleavage was determined by integrating (267 nm) the peaks of the remaining 1b and the product (thymidine). The rates are as follows:

| conc of NaNO$_2$ | actual pH (±0.02) | product after 1 min | product after 2 min |
| --- | --- | --- | --- |
| 350 | 5.50 | n/a | 90% |
| 700 | 5.50 | 98% | >99% |
| 700 | 5.65 | n/a | 96% |

As control, the natural nucleosides were treated as follows: An aqueous solution of 2'-deoxyguanosine or 2'-deoxyadenosine or 2'-deoxycytidine (20 mM, 30 μL) was treated with aqueous nitrous acid (700 mM NaNO$_2$, 1 M NaOAc, pH 5.5, 500 μL) at room temperature for 72 h (i.e. 4320 min). An aliquot (50 μL) was removed, neutralized by the addition of K-phosphate buffer (1 M, 200 μL, pH 7), and analyzed by analytical reverse-phase HPLC (Waters NovaPak C-18 4 μm, 3.9×150 mm, with guard column Waters NovaPak C-18 4 μm, 3.9×15 mm. eluent A=25 mM TEAA pH 7, eluent B=acetonitrile, gradient from 0% B to 3% B in 10 min, then to 30% B in 20 min, flow rate=0.5 mL/min, $R_t$=dG: 14 min, dA: 18 min, dC: 8 min). The amount of decomposition was determined by integrating (260 nm) the peaks of the remaining starting material (nucleoside) and the product(s). The results are as follows:

| nucleoside | byproducts after 72 h @ 260 nm |
| --- | --- |
| dG | 20% |
| dA | 13% |
| dC | 15% |

Example 11

Figure 17:
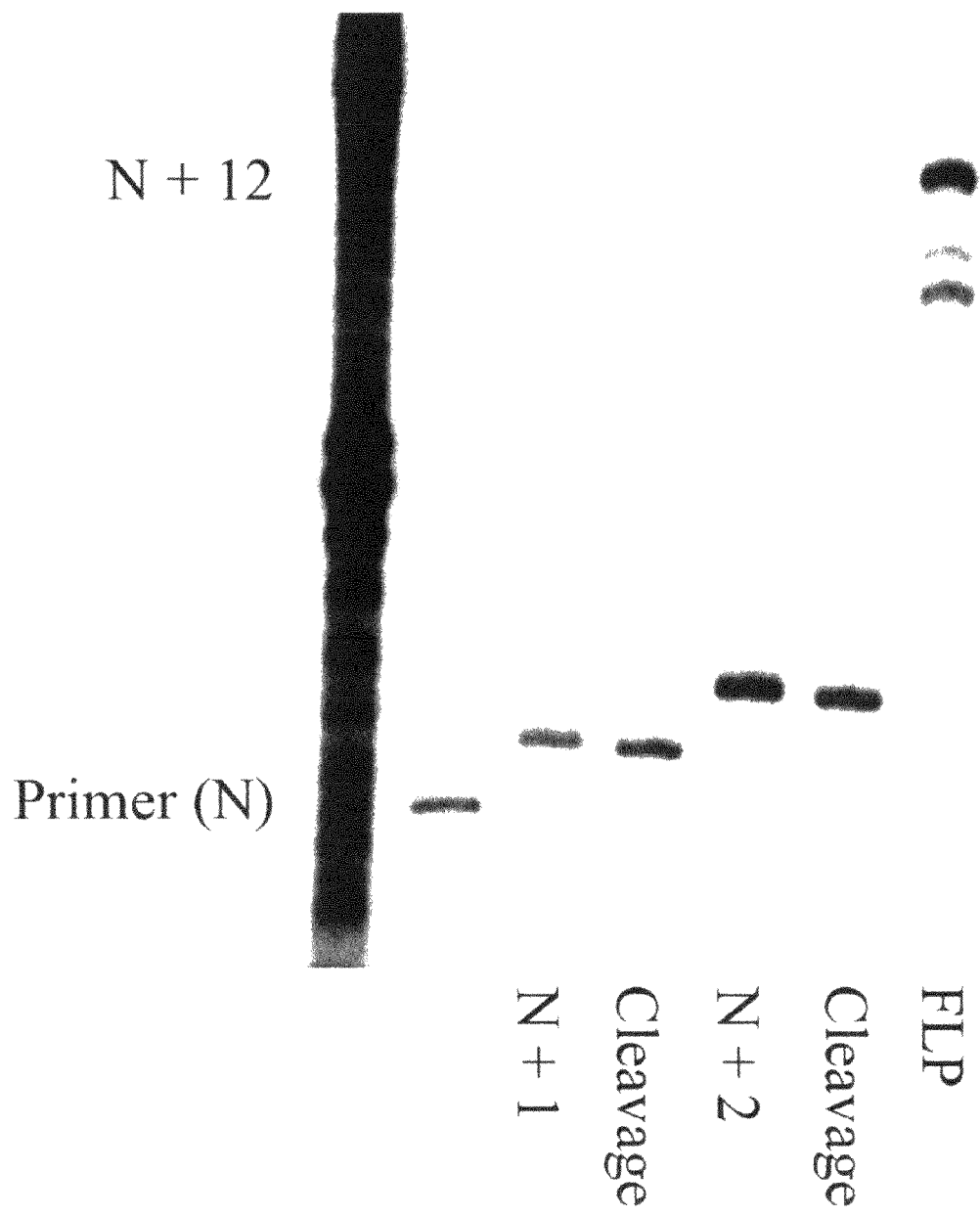
FIG. 17. Example 11. Enzymatic extension with tagged triphosphate.

Standard Cycle with Extension with Termination, then Cleavage (FIG. 17)

Solutions

TTP-ONH$_2$ Stock: 10 mM in 10 mM Tris pH 8.5 (do not treat with HONH$_2$, store at −20° C.)

Stock Solution Hydroxylamine: 50 wt % in ddH$_2$O, store at 4° C.

Cleavage Cocktail (1 mL): Prepared the day of experiments, must be fresh:

This cocktail is 700 mM in nitrous acid (HONO) and optionally contains 30% dioxane, in this case, this results in a pH of 5.7 (dioxane raises the pH). Sodium nitrite (48 mg, 0.7 mmol) is weighed into an eppendorf and dissolved in aqueous Na-acetate buffer (1 M, pH 5.0, 300 μL; plus 1 M, pH 5.5, 400 μL). To this, add dioxane (300 μL).

Quench Buffer: 10 mM EDTA. The buffers listed are treated with hydroxylamine and incubated overnight at room temperature Primary Wash Buffer. 5 mM Tris-HCl pH 7.5, 500 μM EDTA; 1 M NaCl; 2% HONH$_2$ Post Extension Wash buffer. 10 mM Tris pH 8.5, 2% HONH$_2$ ddH$_2$O. Contains 2% HONH$_2$ Post Cleavage Wash. Thermopol Buffer (This is used only in a wash step to remove salts from the primary wash); Supplied by New England Biolabs as 10× and diluted to 1× in ddH$_2$O above. For all trapping and extension reactions listed below neither Tris nor Thermopol buffer are pretreated with hydroxylamine. Only the wash buffers listed above are pretreated.

TTP-ONH$_2$ Trapping Reaction to Remove Contaminating TTP-OH

Contamination by triphosphates is commonplace in polymerase preparations and buffers. Should these be encountered these can be removed using the trapping reaction below, able to clean up as much as 5 and 8% of 3'-unblocked triphosphate in a 10 mM dNTP-ONH$_2$ stock. Here, the procedure is shown for 3'-unblocked dTTP.

```
                                                SEQ ID 1
GCG TAA TAC GAC TCA CTA TGG ACG

SEQ ID 2
CGC ATT ATG CTG AGT GAT ACC TGC AAA AAA AAA AAA-5'
```

1.5 μl of 10 mM TTP-ONH$_2$ stock
2.25 μl Primer (P-1)/Template (T-3) complex (Final concentration of 50 pmol/50 pmol)

1.5 µl 10× Thermopol buffer (no hydroxylamine)
8.25 µl ddH$_2$O (pretreated with hydroxylamine)
1.5 µl Taq 475 (0.5 µg/µL of a Taq stock solution).
   Incubate at 72° C. for 2 min. Keep on ice until ready to use.
   This volume allows for 15 extension reactions that incorporate the reversible terminator.

Extension Reactions

The following are mixed: Template (30 pmol), unlabeled
20 pmol cold primer
2.5 pmol $^{32}$P labeled primer
1× Thermopol Buffer (no hydroxylamine)
100 µM Cleaned-up TTP-ONH$_2$ (use 1 µL of the post trapping reaction)
0.25 µg Taq 475 (1 µL)
Add ddH$_2$O pretreated with HONH$_2$ to give a final volume of 10 µL
Pre-warm reaction (9 µl) to 72° C. for 30 sec (Hot-start)
Initiate reaction with 1 µl of 1 mM Cleaned-up TTP-ONH$_2$
Incubate for 2 min at 72° C.
Quench reaction with 5 µl of a 10 mM EDTA stock Cleavage Reactions The cleavage reaction was initially optimized with the "free" unphosphorylated nucleoside T-ONH$_2$ in solution. Variants are acceptable with or without organic solvents, over a pH range that is preferably 5 to 7. The reaction was analyzed by analytical reverse phase (rp) HPLC and was complete in less than 5 minutes at room temperature (while TTP-ONH2 and TTP-OH cannot be separated by rp HPLC, the unphosphorylated nucleosides T-ONH2 and T-OH can easily be separated). Using the identical reaction conditions for the primer/template attached via streptavidin/biotin to magnetic microbeads led to incomplete cleavage in 5 minutes, however. Without further optimization, and without changing anything else, we then increased the reaction time to 20 minutes, which led to complete cleavage. While we do not think that the reaction with the primer/template attached to a solid support will indeed need that much longer than with the free nucleoside in solution, the ultimate reaction conditions will have to be optimized for the particular architecture in question, and the results that we obtained with our model system can only be seen as a starting point (which is why we did not spend any further effort on optimizing it). Given the small size of the reagent (HONO), we estimate that it will be possible to shorten the reaction with the primer/template on solid support considerably from the 20 minutes that we used, maybe even down to the few minutes needed for the free nucleoside. One additional factor in analyzing/optimizing the cleavage reaction is to make sure that the cleavage cocktail is prepared fresh immediately before use, to prevent side products from the reaction of R-ONH2 with the slow oxidation of dioxane in aging cocktail.

Cleavage buffer is added (for each 10 µL reaction, 100 µL of cleavage buffer) and the mixture is incubated at RT for 20 min (shorter times also apply). The cleavage buffer is washed away from the material on the magnetic beads, which are washed twice with Primary Wash Buffer. Salts and the chelator are removed by washing twice with Post Cleavage Buffer (wash twice). The cycle is repeated an indefinite number of times.

Example 12

Figure 18:
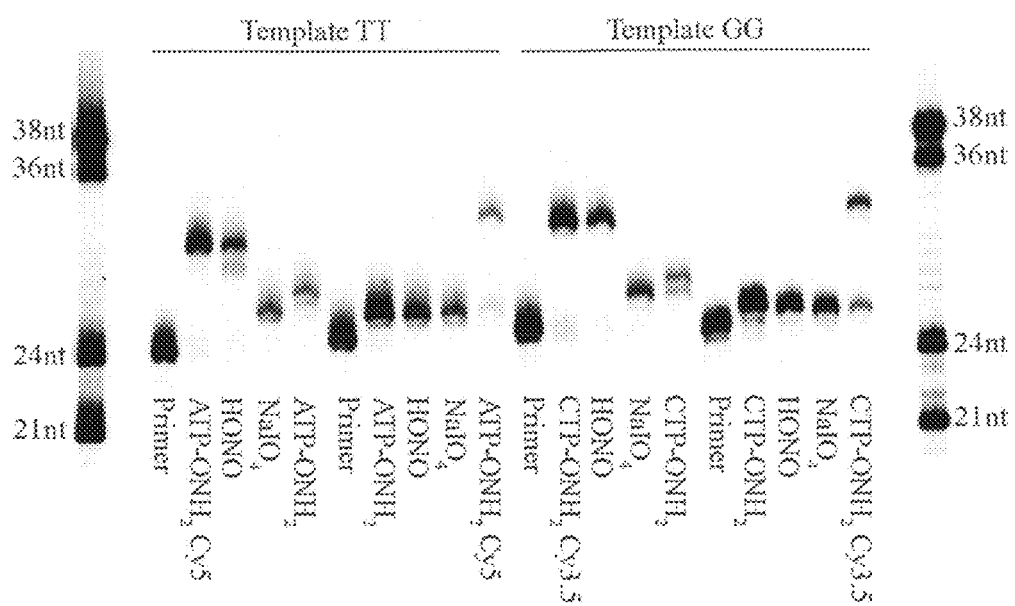
FIG. 18. Example 12. Sequencing using cyclic reversible termination cycle
FIG. 19. Example 13. Enzymatic extension with tagged 3'-ONH$_2$ triphosphates and "scars"
FIG. 20. Example 14. Enzymatic extension with tagged 3'-ONH$_2$ triphosphates and "scars"
FIG. 21. Structures used in Example 13.

Sequencing Using Cyclic Reversible Termination Cycle (FIG. 18)

This example shows the use of reversible terminators in a sequencing cycle using 7-deaza ATP-ONH$_2$ tagged with Cy5 and CTP-ONH$_2$ tagged with Cy3.5. In these experiments, material was immobilized via the biotin on Dynabeads® a magnetic bead carrying streptavidin.

Primer, Template, Triphosphates:

SEQ ID 1
$^{32}$P 5'-GCG TAA TAC GAC TCA CTA TGG ACG-3'

SEQ ID 3
5'Biotin-GTC TTC GTG TTT CGT CCA TAG TGA GTC GTA TTA CGC-3'

SEQ ID 4
5'Biotin-GTC TTC GTG TGG CGT CCA TAG TGA GTC GTA TTA CGC-3'

1) ATP-ONH$_2$ Cy5 (internal reference)
2) ATP-ONH$_2$ (internal reference)
3) CTP-ONH$_2$ Cy3.5 (internal reference)
4) CTP-ONH$_2$ (internal reference)

All of the buffers (except the cleavage buffer) were pre-incubated overnight with 0.5% hydroxylamine. The primer template complex was prepared by annealing γ$^{32}$P-labeled Primer P-1 (SEQ ID 1, 1 pmol), cold primer P-1 (SEQ ID 1, 20 pmol) and Template GG (SEQ ID 4) or TT (SEQ ID 3), each at 30 pmol, by incubation at 96° C. for 5 min followed by cooling to room temperature over 1 hour (10 µL reaction volume). Four sequencing reactions were run consecutively, and the results are shown in FIG. 18.

1) ATP-ONH$_2$ Cy5, HONO, NaIO$_4$, ATP-ONH$_2$
2) ATP-ONH$_2$, HONO, NaIO$_4$, ATP-ONH$_2$ Cy5
3) CTP-ONH$_2$ Cy3.5, HONO, NaIO$_4$, CTP-ONH$_2$
4) CTP-ONH$_2$, HONO, NaIO$_4$, CTP-ONH$_2$ Cy3.5

TABLE

Reaction protocols
1$^{st}$ extension reaction:

Two different reactions containing:
30 pmol Template
20 pmol cold primer
1 pmol labeled primer
1X Thermopol Buffer
100 µM appropriate triphosphate
0.5 Units Therminator
Pre-warm reaction (9 µl) to 72° C. for 30 sec
Initiate reaction with 1 µl of 1 mM triphosphate
Incubate for 4 min at 72° C.
Quench reaction with 5 µl of 10 mM EDTA
Clean up reactions after each step by washing twice with 500 µL of wash buffer, with the template-product complex captured on Dynabeads ®.

A cleavage cocktail is made by mixing two aqueous acetic acid:sodium acetate buffers, each with total acetate=1 M, the first at pH 5.0, the second at pH 5.5, in a ratio of 3:4 (typically, 300 µL of the first was mixed with 400 µL of the second, followed by addition of sodium nitrite (48 mg, 0.7 mmol). Optionally, dioxane (300 µL) was added, and these conditions were used in this example. The final pH was approximately 5.7. Following extension, the template-product is captured on Dynabeads®, and the mixture was incubated at room temperature for 20 min in the cleavage buffer. The products were captured again and the magnetic beads were washed twice with 500 µL of wash buffer. The buffer was removed and reaction buffer was added for extension reactions 2$^{nd}$ Round of Primer Extensions
30 pmol Template
20 pmol cold primer
1 pmol labeled primer
1× Thermopol Buffer
100 µM appropriate triphosphate
0.5 Units Therminator
Pre-warm reaction (9 µl) to 72° C. for 30 sec
Initiate reaction with 1 µl of 1 mM appropriate triphosphate
Incubate for 4 min at 72° C.
Quench reaction with 5 µl of 10 mM EDTA As shown in FIG. 18, Therminator successfully incorporates fluorescently labeled reversible terminators after a standard base and a —ONH$_2$ cleaved base "scarred" in the primer. Therminator can also incorporate ATP-ONH$_2$ and CTP-ONH$_2$ after a scarred base on a primer.

Example 13

Figure 19:
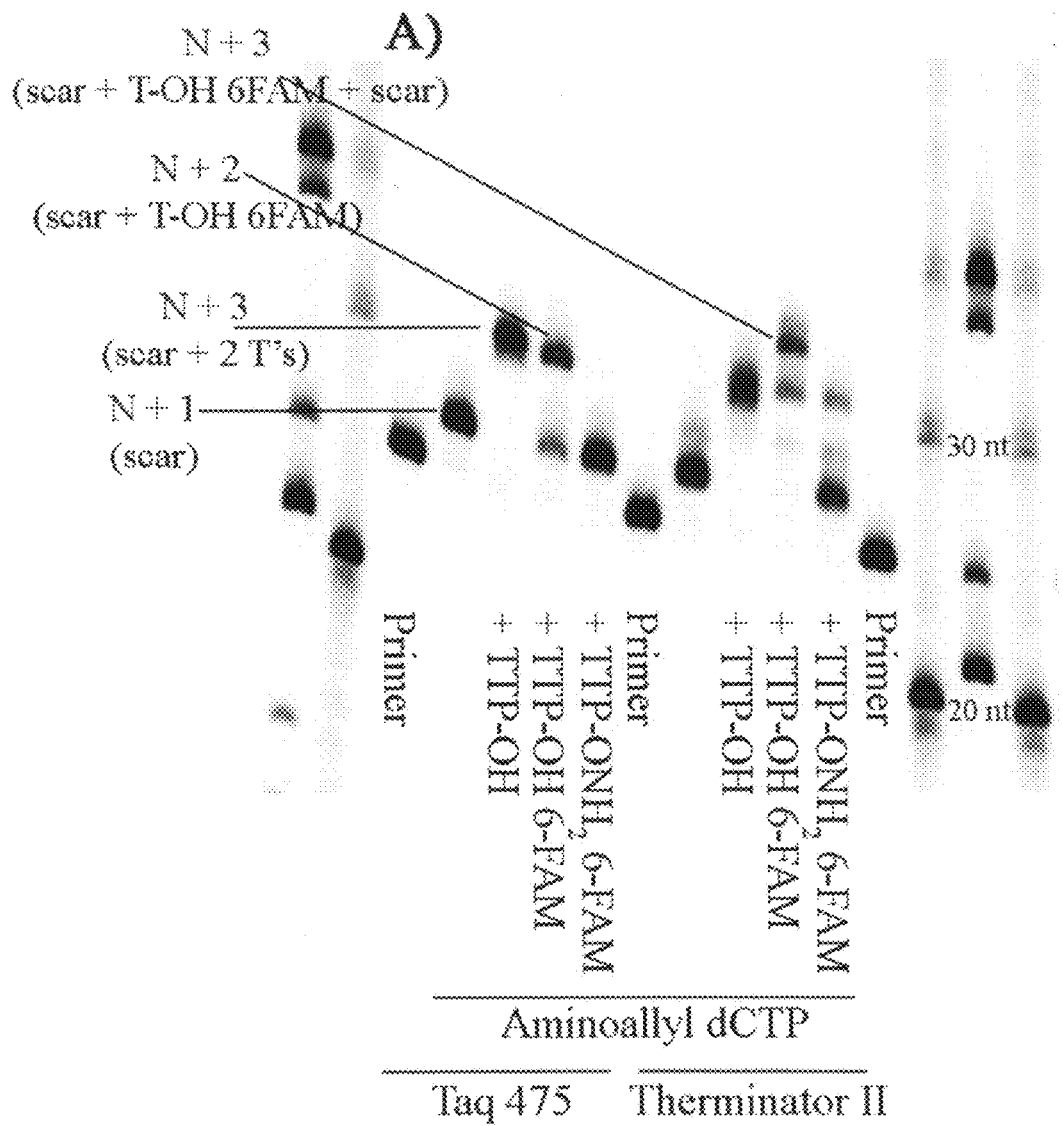

Incorporation of Tagged Terminated Triphosphate Following "Scar" (FIG. 19)

Figure 21:
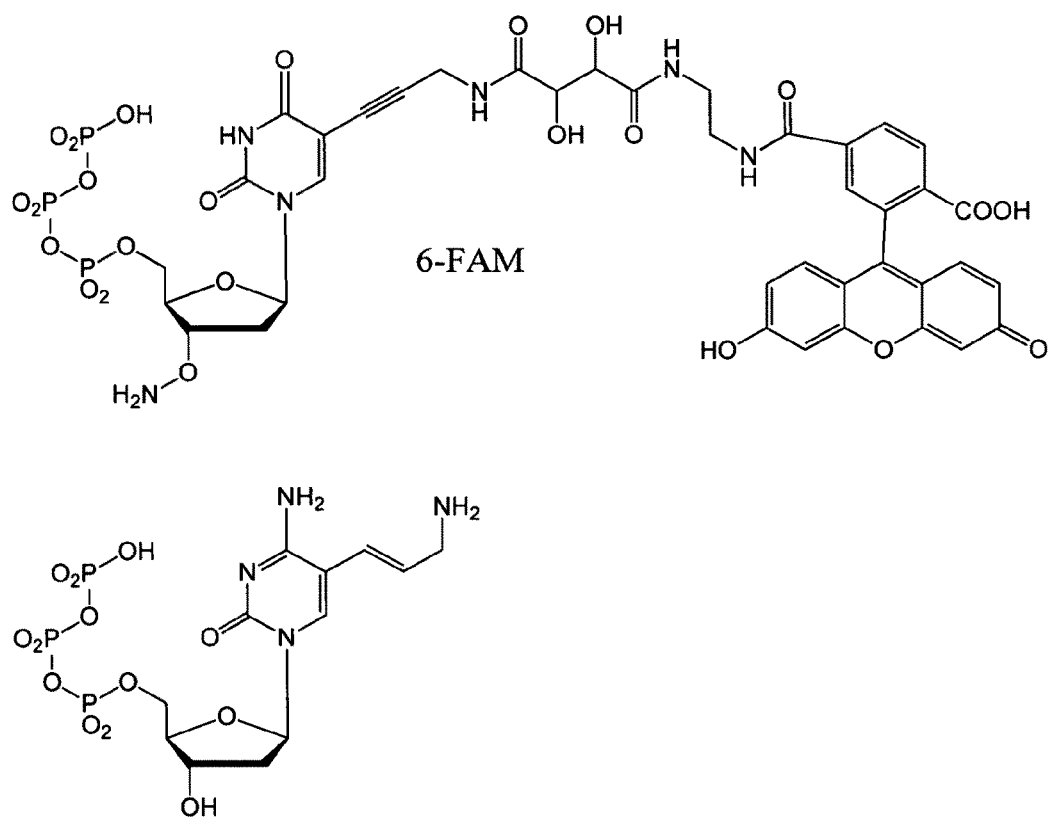

The scar was represented by an aminoallyl tagged nucleotide (FIG. 21). Two polymerases were examined: Taq Variant [E517G, K537I, L613A] and Therminator II.
Primer and Template:

```
                                               SEQ ID 1
32P 5'-GCG TAA TAC GAC TCA CTA TGG ACG-3'

SEQ ID 5
5'-GTC TTC GTG AAG CGT CCA TAG TGA GTC GTA TTA
CGC-3'
```

Triphosphates:
1) 5-Aminoyallyl-2'-deoxycytidine-5'-triphosphate ("scarred triphosphate")
2) TTP-OH 6-FAM (435-572-ionex-A)-Same as the TTP-ONH$_2$ 6-FAM except the —ONH$_2$ was removed by treatment with HONO and then the main product was isolated
3) TTP-OH
4) TTP-ONH$_2$ 6-FAM Extension Reaction:
In a 10 μL reaction volume γ$^{32}$P-labeled primer (SEQ ID 1) (1 pmol), cold primer (20 pmol) and template (SEQ ID 5) (30 pmol) were annealed by incubation at 96° C. for 5 min and cooled to room temperature. The indicated Taq variant (0.25 μg/μL) or Therminator II (2 U/rxn) were added to the mixtures. Assays contained 20 mM Tris-HCl pH 8.8, 10 mM KCl, 10 mM (NH$_4$)$_2$SO$_4$, 2 mM MgSO$_4$ and 0.1% Triton X-100. Assays were initiated by appropriate triphosphates (100 μM final) and incubated at 72° C. for the indicated time (typically 30 sec or 2 min). Mixtures were then either quenched with 20 μL of 10 mM quench buffer or presented with another appropriate triphosphate (100 μM) for 2 min. Samples (4 μL) were resolved on a 20% denaturing polyacrylamide gel and analyzed with a Molecular Imager.

As shown in FIG. 19, the Taq variant incorporates the aminoallyl base to give N+1 and a very small amount of N+2 product. The N+2 band could be due to either a mismatch of the scar opposite A, or a non-templated addition of the scar (Panel A). The Taq variant incorporates the standard TTP-OH after the scar giving N+3 product (scar+2 A's). This variant is also able to incorporate one TTP-OH 6-FAM after the scar and then terminate (N+2). A small amount of un-extended scar (N+1) remains. A combination of TTP-OH 6-FAM and Taq Variant is therefore useful sequencing reactions.

Example 14

Figure 20:
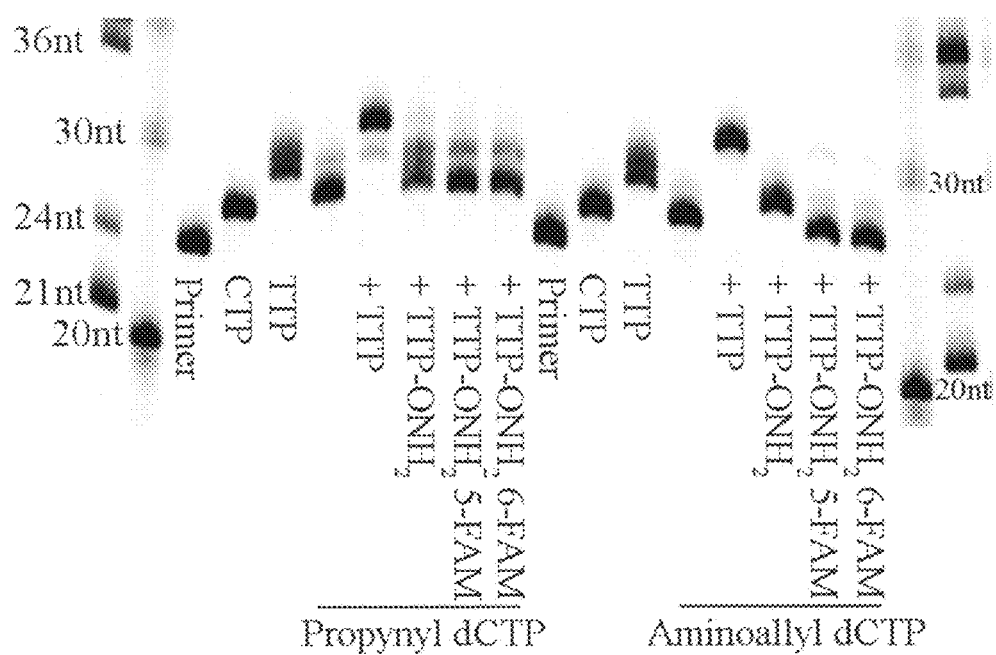

Taq Variants, Various Scars, and Tagged Terminated Triphosphates (FIG. 20)

Primer and Template:

```
                                               SEQ ID 1
32P 5'-GCG TAA TAC GAC TCA CTA TGG ACG-3'

SEQ ID 5
5'-GTC TTC GTG AAG CGT CCA TAG TGA GTC GTA TTA
CGC-3'
```

Figure 22:
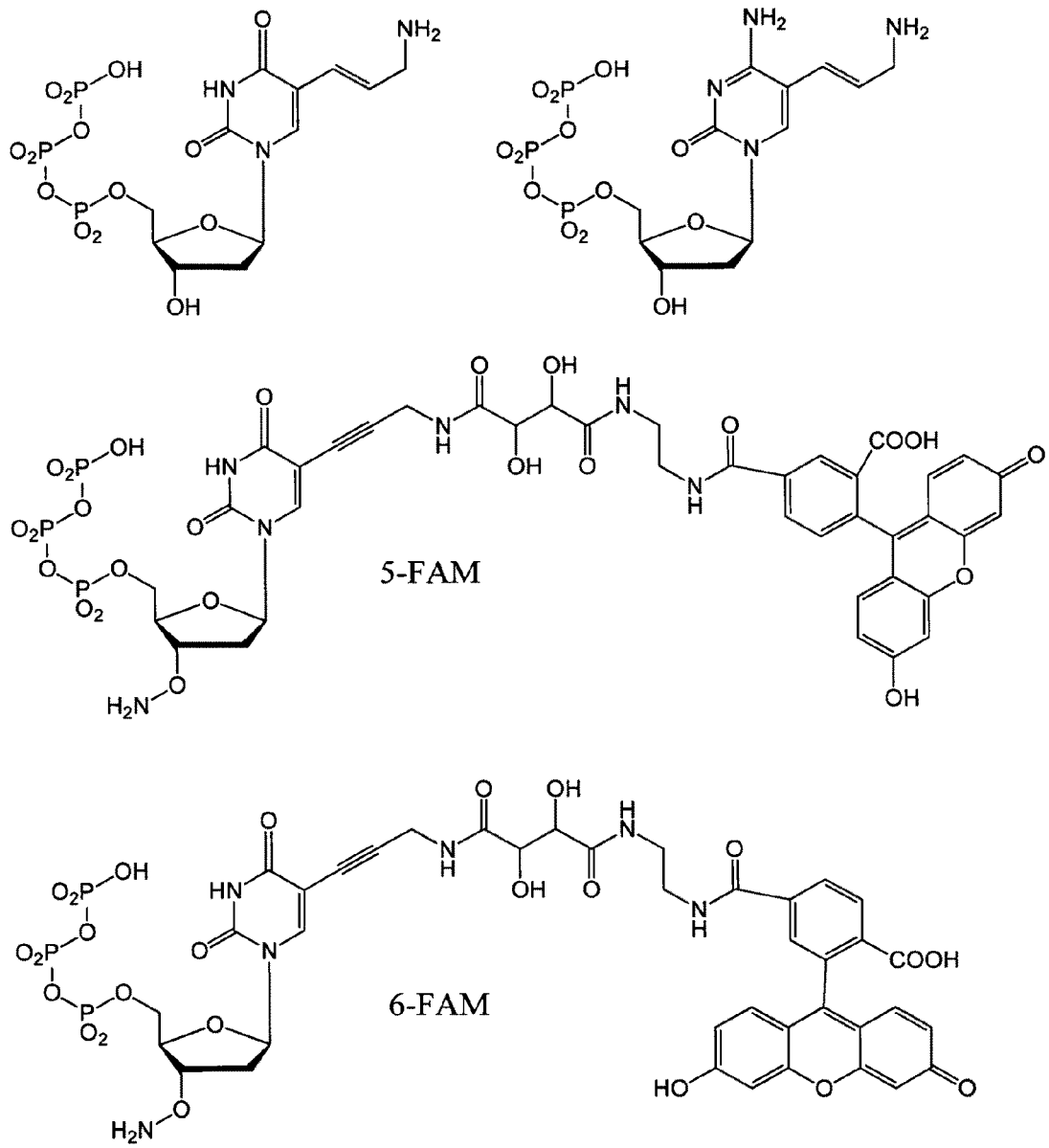
FIG. 22. Structures used in Example 14.

Triphosphates (FIG. 22)
1) 5-Propynyl-2'-deoxycytidine-5'-triphosphate ("scarred triphosphate")
2) 5-Aminoyallyl-2'-deoxycytidine-5'-triphosphate ("scarred triphosphate")
3) TTP-ONH$_2$ 5-FAM
4) TTP-ONH$_2$ 6-FAM
5) TTP-OH
6) CTP-OH
7) TTP-ONH$_2$ (1b)

In a 10 μL reaction volume, γ$^{32}$P-labeled primer (SEQ ID 1) (1 pmol), cold primer (20 pmol) and template (SEQ ID 5) (30 pmol) were annealed by incubation at 96° C. for 5 min followed by cooling to cooled to RT. Assays contained 20 mM Tris-HCl pH 8.8, 10 mM KCl, 10 mM (NH$_4$)$_2$SO$_4$, 2 mM MgSO$_4$ 0.1% Triton X-100, and Taq variant [A594T, L613A, F664Y, E742H] (0.25 μg/μL) Assays were initiated by appropriate triphosphates (100 μM final) and the mixture incubated at 72° C. for indicated times (typically 30 sec or 2 min). Reactions were either quenched with 20 μL of 10 mM quench buffer or presented with another appropriate triphosphate (100 μM) for 2 min. Samples (4 μL) were resolved on a 20% denaturing polyacrylamide gel and analyzed with a Molecular Imager.

As shown in FIG. 20, the Taq variant added the propynyl and the aminoallyl nucleotide to give N+1 product with some N+2 after the propynyl scar (FIG. 20). The Taq variant also incorporated the standard TTP-OH after both of the scarred products giving a product of N+4 (scar+3 T's). This polymerase incorporated TTP-ONH$_2$ after the aminoallyl scar. The Taq variant was unable to incorporate the fluor reversible terminator after either of the differently scarred products.

What is claimed is:

1. A composition of matter having the structure:

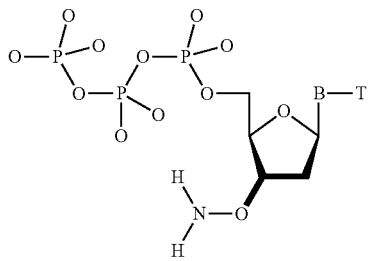

wherein B is a nucleobase capable of forming a Watson-Crick pair with a complementary adenine, guanine, cytosine, thymine or uracil in a complementary DNA or RNA strand, and T is a fluorescent tag attached via a linker that is cleavable by adding a reagent in aqueous solution near neutral pH.

2. The composition of claim 1 wherein said cleavable linker comprises a 1,2-dihydroxy moiety.

3. The composition of claim 2, wherein said composition is selected from the group consisting of

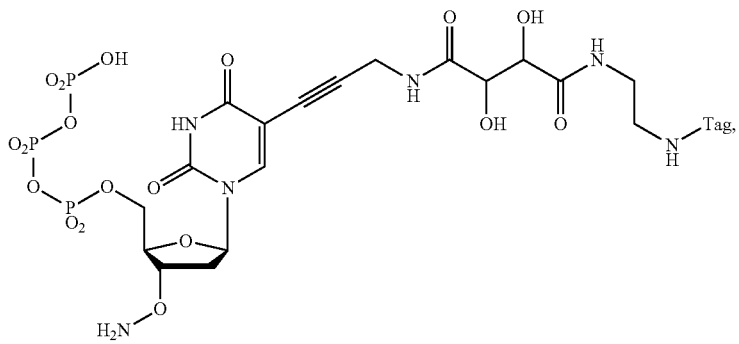

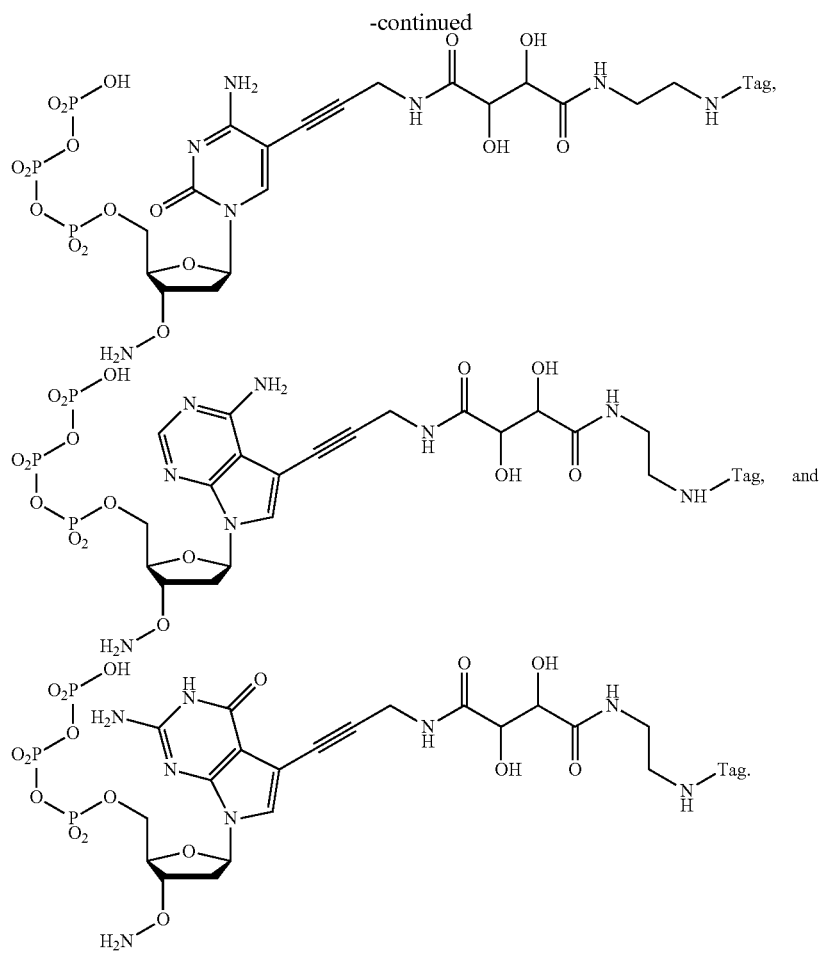

4. A composition of matter having the structure:

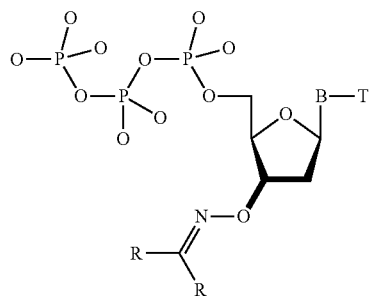

wherein B is a nucleobase capable of forming a Watson-Crick pair with a complementary adenine, guanine, cytosine, thymine or uracil in a complementary DNA or RNA strand, R is independently selected from the group consisting of hydrogen, alkyl, and aryl, and T is a fluorescent tag attached via a linker that is cleavable by adding a reagent in aqueous solution near neutral pH.

5. The composition of claim 4 wherein said cleavable linker comprises a 1,2-dihydroxy moiety.

6. The composition of claim 5, wherein said composition is selected from the group consisting of

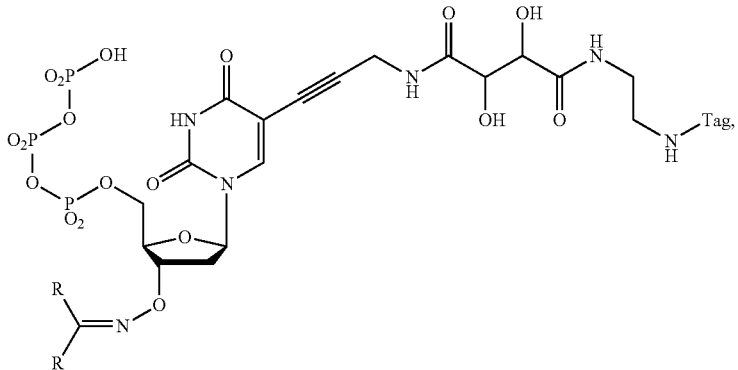

-continued

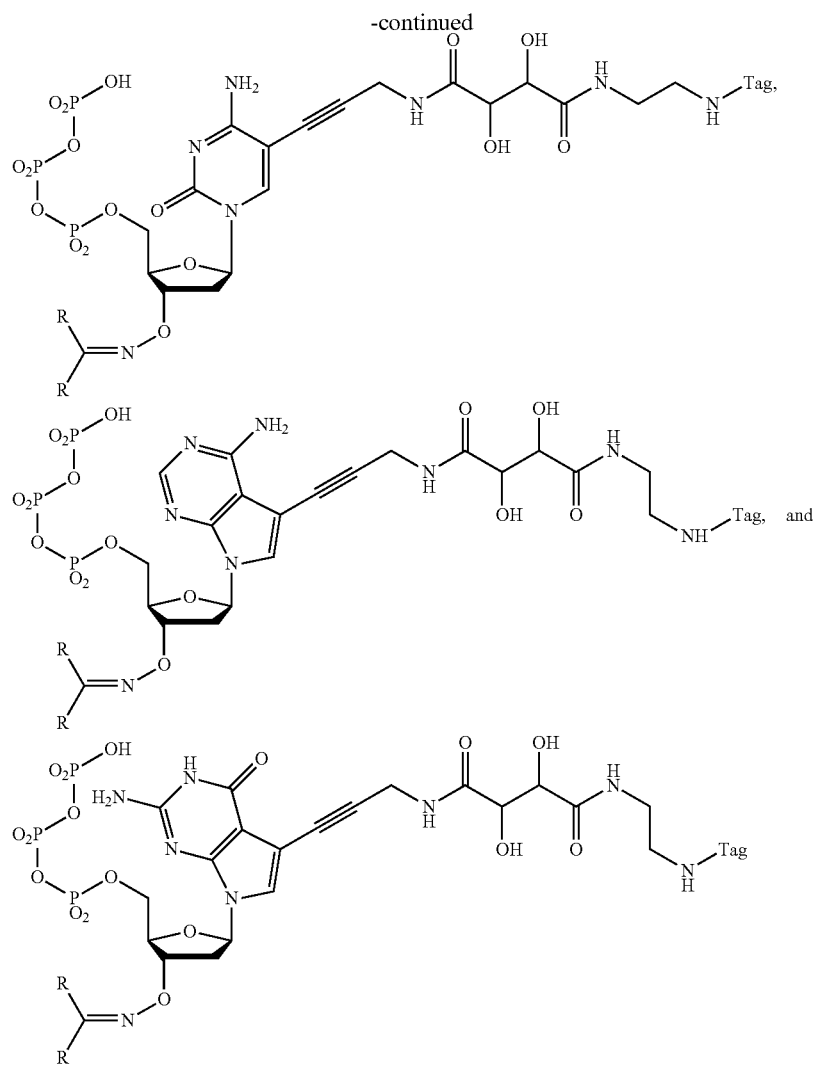

wherein B is a nucleobase capable of forming a Watson-Crick pair with a complementary adenine, guanine, cytosine, thymine or uracil in a complementary DNA or RNA strand, T is a fluorescent tag, and R is independently selected from the group consisting of hydrogen, alkyl, and aryl.

7. An improvement on the process of U.S. Pat. No. 6,664,079, which claims a method for sequencing a nucleic acid by detecting the identity of a nucleotide analogue after the nucleotide analogue is incorporated into a growing strand of DNA in a polymerase reaction, which comprises the following steps:

(i) attaching a 5' end of the nucleic acid to a soild surface;
(ii) attaching a primer to the nucleic acid attached to the solid surface;
(iii) adding a polymerase and one or more different nucleotide analogues to the nucleic acid to thereby incorporate a nucleotide analogue the growing strand of DNA, wherein the incorporated nucleotide analogue terminates the polymerase reaction and wherein each different nucleotide analogue comprises (a) a base selected from the group consisting of adenine, guanine, cytosine, thymine, and uracil, and their analogues; (b) a unique label attached through a cleavable linker to the base or to an analogue of the base; (c) a deoxyribose; and (d) a cleavable chemical group to cap an —OH group at a 3'-position of the deoxyribose;
(iv) washing the solid surface to remove unincorporated nucleotide analogues;
(v) detecting the unique label attached to the analogue that has been incorporated into the growing strand of DNA so as to thereby identify the incorporated nucleotide analogue;
(vi) adding one or more chemical compqunds to permanently cap any unreacted —OH group on the primer attached to the nucleic acid or on a primer extension strand formed by adding one or more nucleotides or nucleotide analogues to the primer;
(vii) cleaving the cleavable linker between the nucleotide analogue that was incorporated into the growing strand of DNA and the unique label;
(viii) cleaving the cleavable chemical group capping the —OH group at the 3'-position of the deoxyribose to uncap the —OH group, and washing the solid surface to remove cleaved compounds; and
(ix) repeating steps (iii) through (viii) so as to detect the identity of a newly incorporated nucleotide analogue into the grouwing strand of DNA;

wherein if the unique label is a mass tag, the order of steps (v) through (vii) is; (v), (vi), and (vii); and wherein if the unique label is a mass tag, the order of steps (v) through (vii) is; (vi), (vii), and (v), wherein said improvement comprises eliminating step (vi) and with step (iii) of said process, after the addition step, contacting a complex between a template and a primer in the presence of a DNA polymerase, and incubating said complex with one or more compounds, which correspond to the first named analogous in step (iii), having the structure:

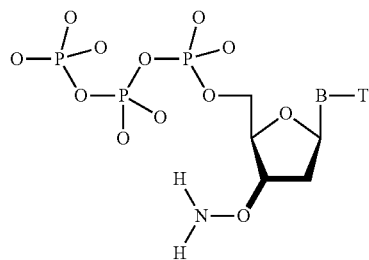

wherein B is a nucleobase capable of forming a Watson-Crick pair with a complementary adenine, guanine, cytosine, thymine or uracil in a complementary DNA or RNA strand, and T either a hydrogen atom, a methyl group, or a fluorescent tag attached via a linker that is cleavable by adding a reagent in aqueous solution near neutral pH.

8. The improvement of claim 7 wherein said cleavable linker comprises a 1,2-dihydroxy moiety.

9. The improvement of claim 8, wherein said improvement comprises molecules selected from the group consisting of

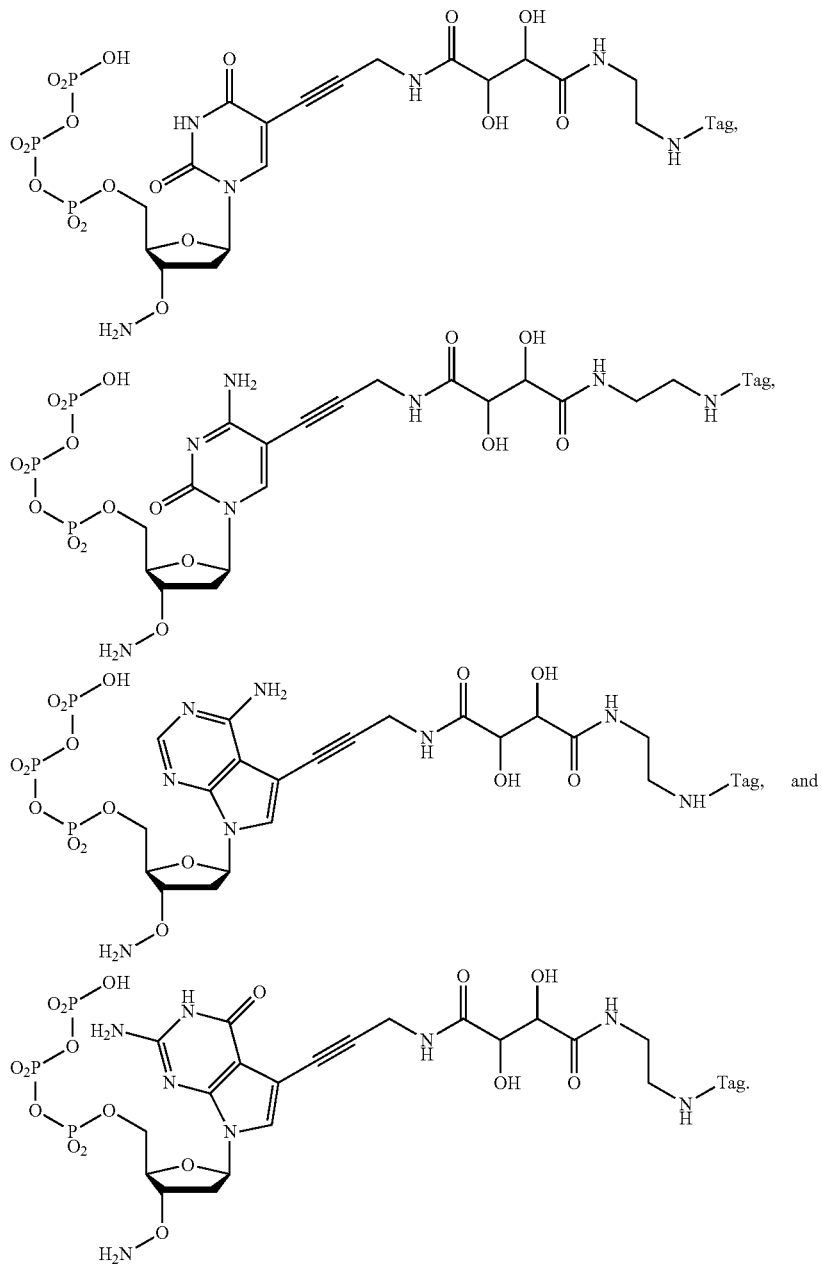

10. The composition of Claim 1 wherein said cleavable linker comprises a disulfide moiety.

11. The composition of claim 1, wherein said composition is selected from the group consisting of 12. The composition of claim 4 wherein said cleavable linker comprises a disulfide moiety.

13. The composition of claim 12, wherein said composition is selected from the group consisting of

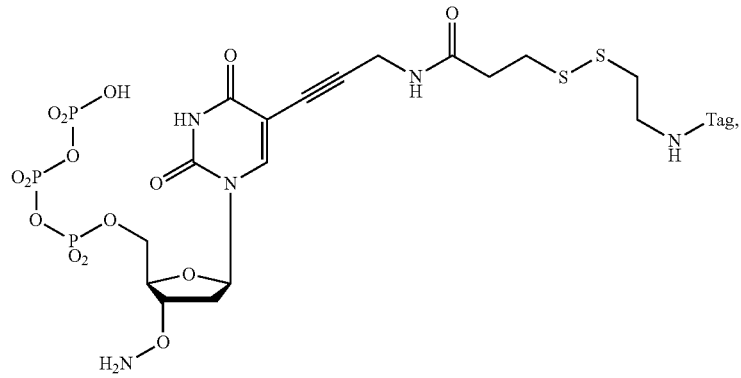

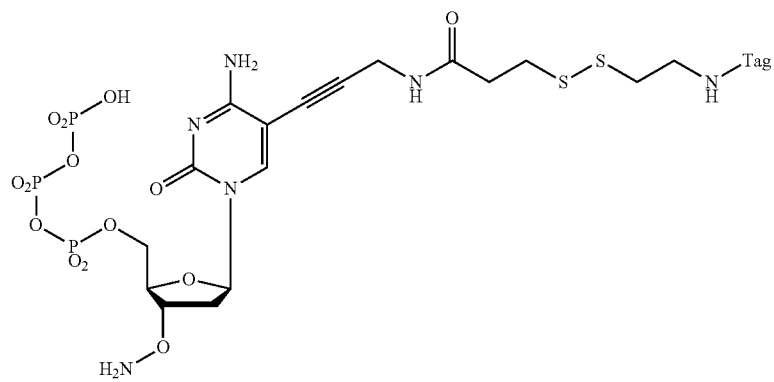

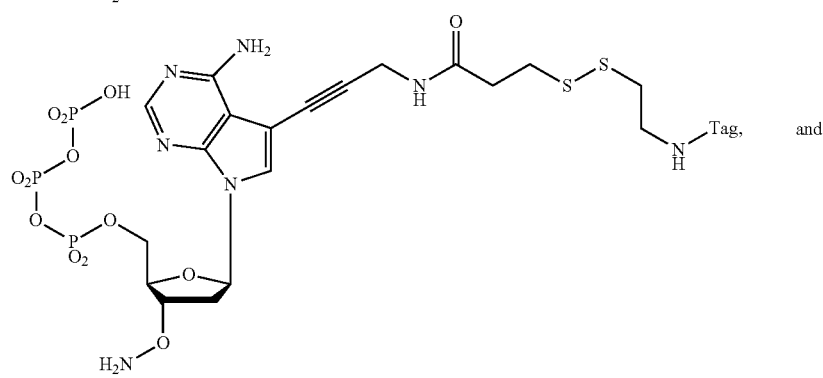

and

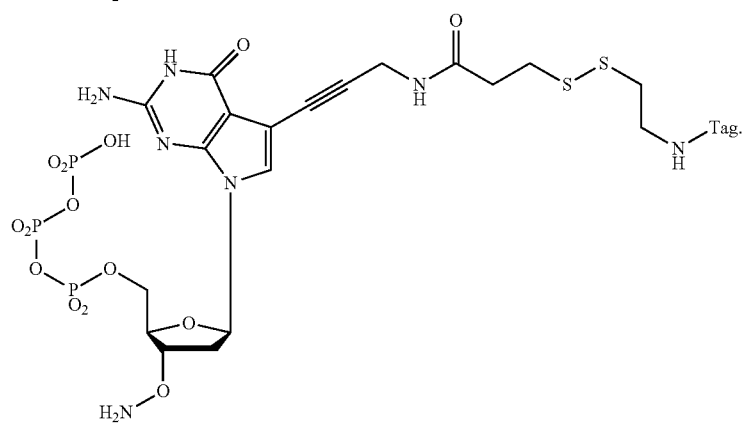

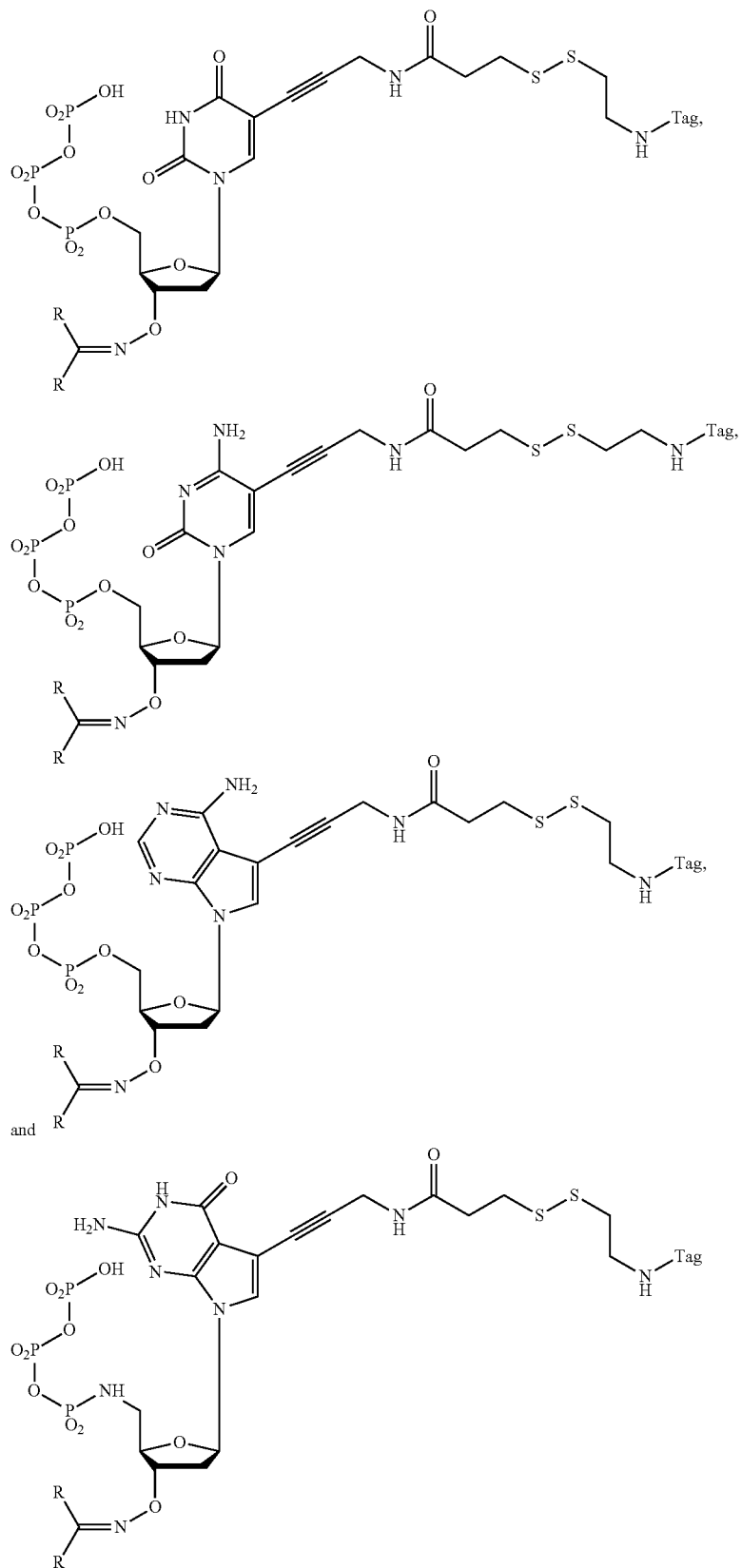
wherein B is a nucleobase capable of forming a Watson-Crick pair with a complementary adenine, guanine, cytosine, thymine or uracil in a complementary DNA or RNA strand, T is a fluorescent tag, and R is independently selected from the group consisting of hydrogen, alkyl, and aryl.
* * * * *

SEQUENCE LISTING

<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
gcgtaatacg actcactatg gacg                                      24

<210> SEQ ID NO 2
<211> LENGTH: 36
<212> TYPE: DNA
<213> ORGANISM: Artificial Sequence

```
<220> FEATURE:
<223> OTHER INFORMATION: Synthetic

<400> SEQUENCE: 2
aaaaaaaaaa aacgtccata gtgagtcgta ttacgc                               36

<210> SEQ ID NO 3
<211> LENGTH: 36
<212> TYPE: DNA
<213> ORGANISM: Artificial Sequence
<220> FEATURE:
<223> OTHER INFORMATION: Synthetic

<400> SEQUENCE: 3
gtcttcgtgt ttcgtccata gtgagtcgta ttacgc                               36

<210> SEQ ID NO 4
<211> LENGTH: 36
<212> TYPE: DNA
<213> ORGANISM: Artificial Sequence
<220> FEATURE:
<223> OTHER INFORMATION: Synthetic

<400> SEQUENCE: 4
gtcttcgtgt ggcgtccata gtgagtcgta ttacgc                               36

<210> SEQ ID NO 5
<211> LENGTH: 36
<212> TYPE: DNA
<213> ORGANISM: Artificial Sequence
<220> FEATURE:
<223> OTHER INFORMATION: Synthetic

<400> SEQUENCE: 5
gtcttcgtga agcgtccata gtgagtcgta ttacgc                               36
```